(12) United States Patent
Dudee

(10) Patent No.: US 11,672,650 B2
(45) Date of Patent: Jun. 13, 2023

(54) INTRAOCULAR OPTIC ASSEMBLY

(71) Applicant: Jitander Dudee, Lexington, KY (US)

(72) Inventor: Jitander Dudee, Lexington, KY (US)

( * ) Notice: Subject to any disclaimer, the term of this patent is extended or adjusted under 35 U.S.C. 154(b) by 429 days.

(21) Appl. No.: 16/865,699

(22) Filed: May 4, 2020

(65) Prior Publication Data

US 2020/0261217 A1 Aug. 20, 2020

Related U.S. Application Data

(60) Division of application No. 16/355,882, filed on Mar. 18, 2019, now Pat. No. 10,709,551, which is a continuation-in-part of application No. 14/979,449, filed on Dec. 27, 2015, now Pat. No. 10,265,163.

(60) Provisional application No. 62/645,297, filed on Mar. 20, 2018, provisional application No. 62/097,052, filed on Dec. 27, 2014.

(51) Int. Cl.
*A61F 2/16* (2006.01)
*A61F 9/00* (2006.01)

(52) U.S. Cl.
CPC .......... *A61F 2/1694* (2013.01); *A61F 2/1616* (2013.01); *A61F 2/1624* (2013.01); *A61F 2/1629* (2013.01); *A61F 2/1662* (2013.01); *A61F 2/161* (2015.04); *A61F 9/0008* (2013.01); *A61F 2002/1681* (2013.01); *A61F 2002/1682* (2015.04)

(58) Field of Classification Search
CPC .... A61F 2/1616; A61F 2/1624; A61F 2/1629; A61F 2002/1681; A61F 2002/1682
See application file for complete search history.

(56) References Cited

U.S. PATENT DOCUMENTS

| | | | | |
|---|---|---|---|---|
| 2004/0249455 A1* | 12/2004 | Tran | ...................... | A61F 2/1613 |
| | | | | 623/6.37 |
| 2005/0113914 A1* | 5/2005 | Miller | ................... | A61F 2/1629 |
| | | | | 623/6.37 |
| 2007/0106381 A1* | 5/2007 | Blake | .................... | A61F 2/1694 |
| | | | | 623/6.37 |

* cited by examiner

*Primary Examiner* — Javier G Blanco
(74) *Attorney, Agent, or Firm* — Black, McCuskey, Souers & Arbaugh, LPA

(57) ABSTRACT

An intraocular optic assembly can include a first lens, a first plurality of stanchions, a second lens, and a second plurality of stanchions. A central optic axis can extend through centers of the first and second lenses. The first plurality of stanchions can each extend a first distance between a first base end and a first distal end. The first lens can be connected with the first distal ends. The second plurality of stanchions can each extend a second distance between a second base end and a second distal end. The second lens can be connected with the second distal ends. Compression at the peripheries of the stanchions induces movement of the lenses apart from one other.

15 Claims, 37 Drawing Sheets

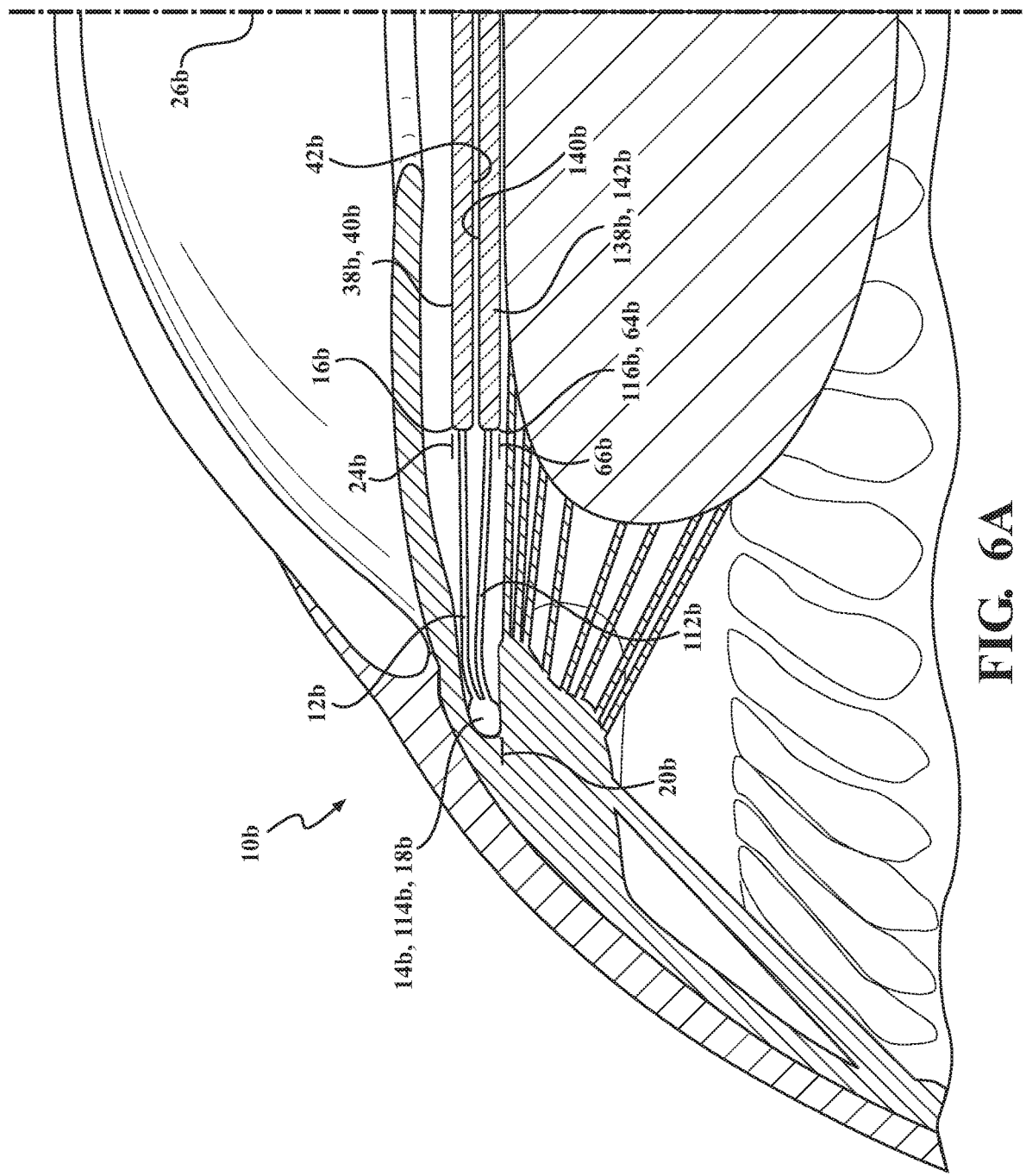

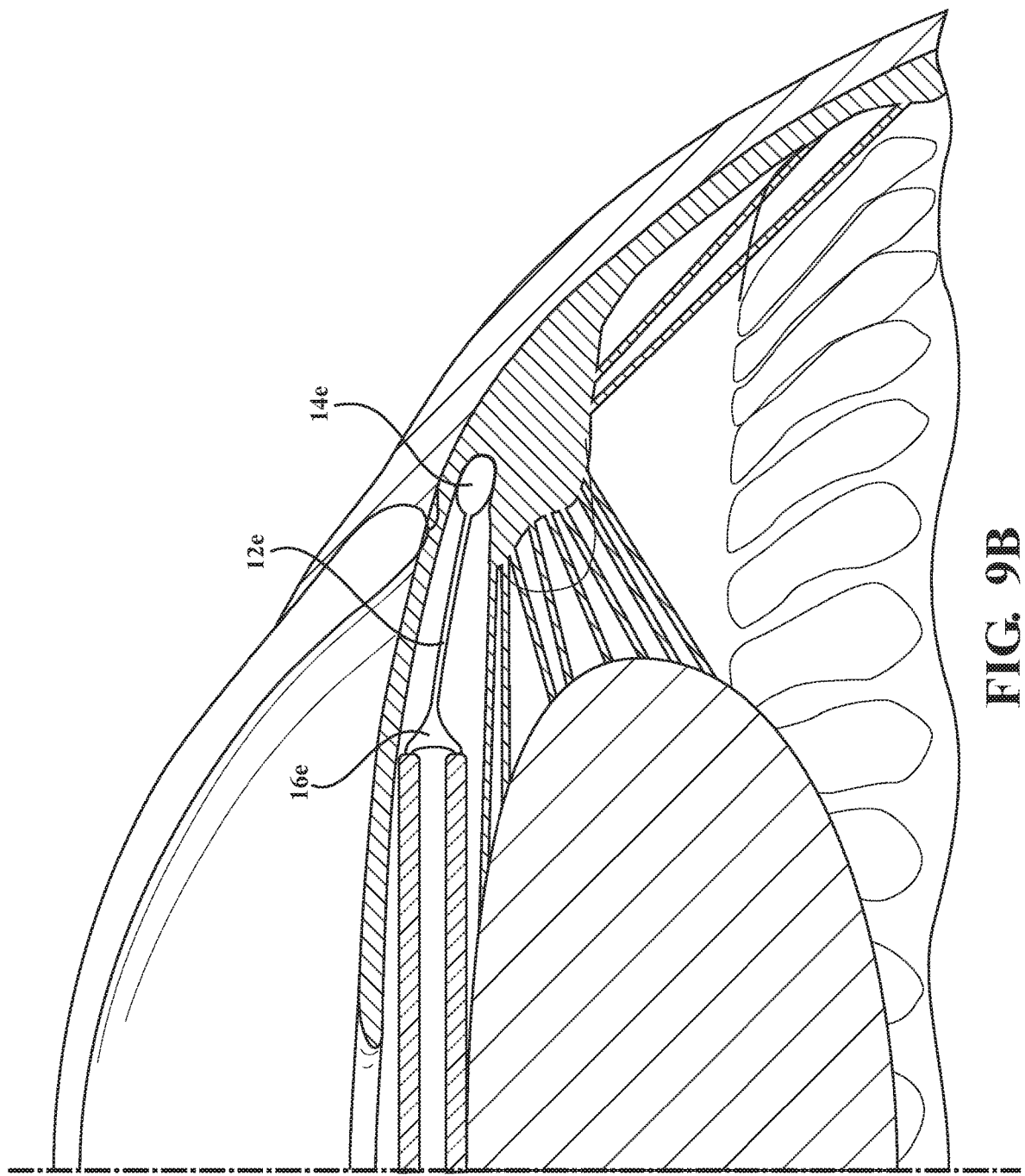

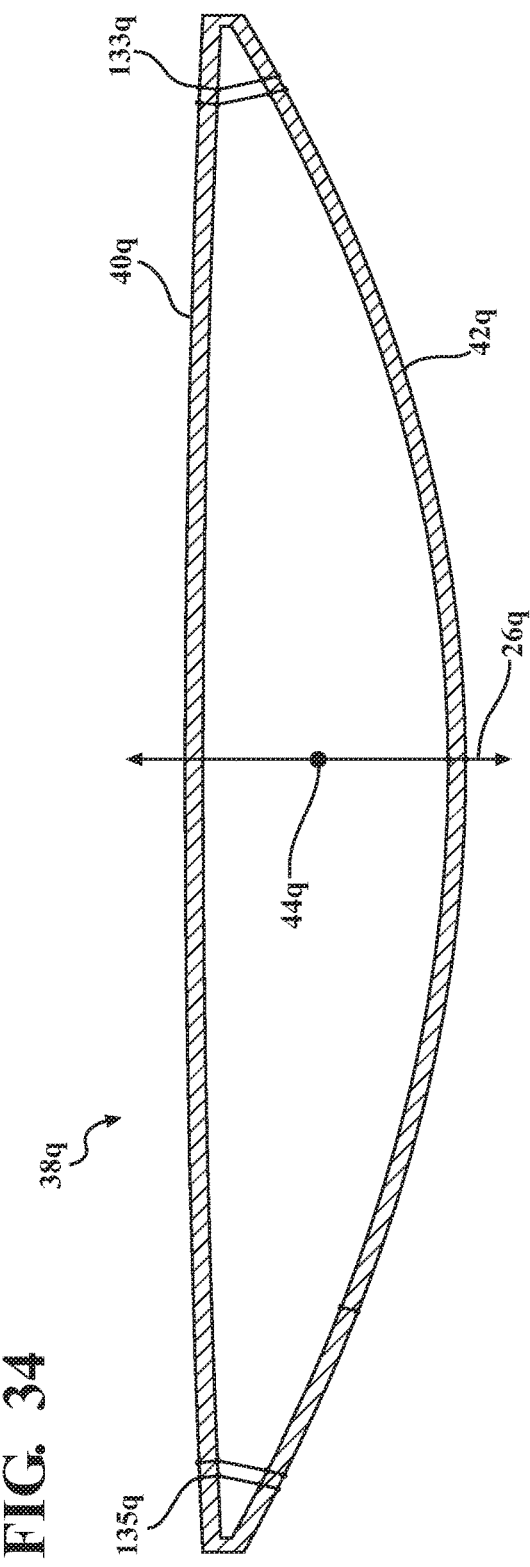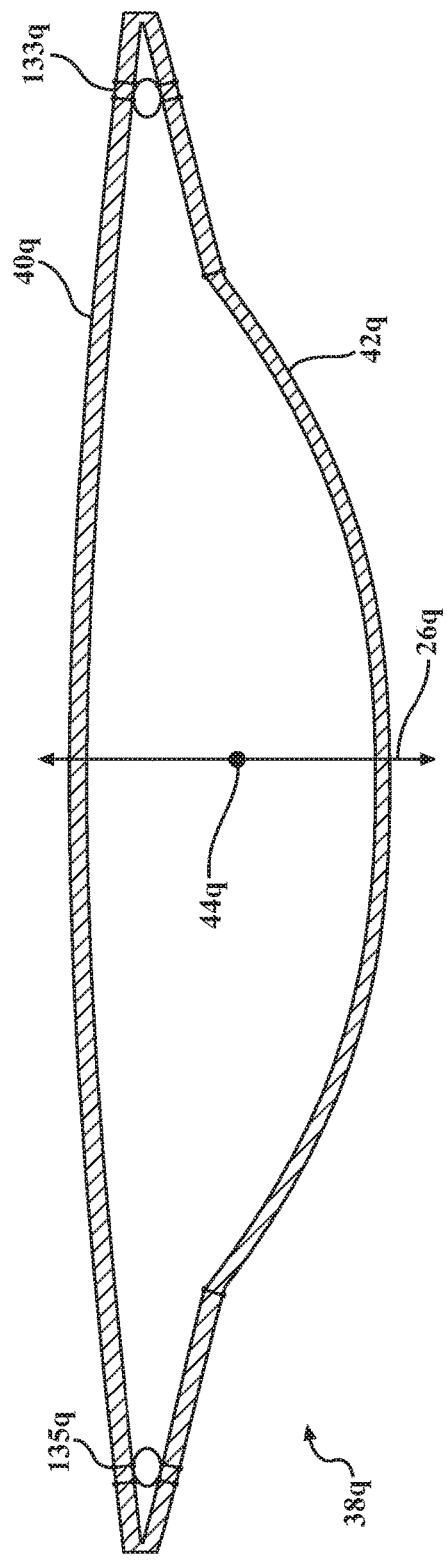

FIG. 36A
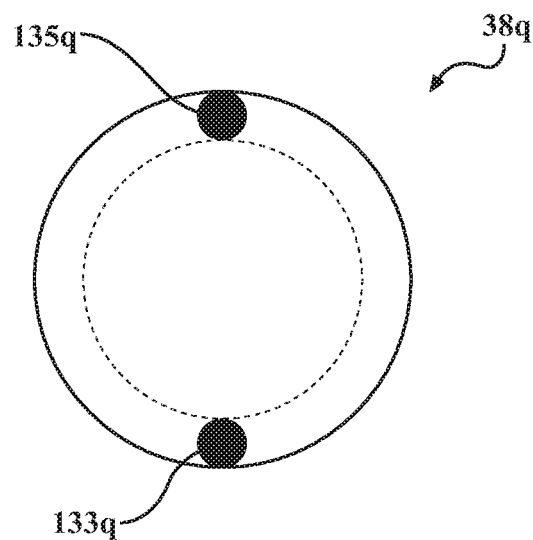
FIG. 36C
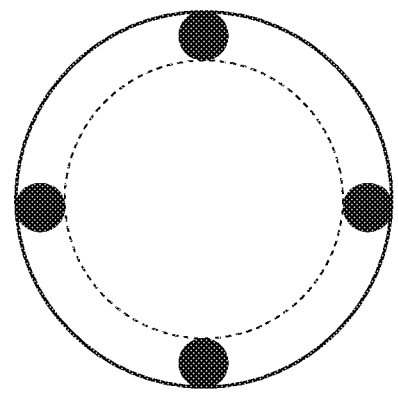
FIG. 36B
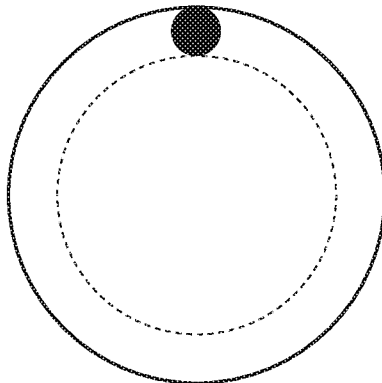
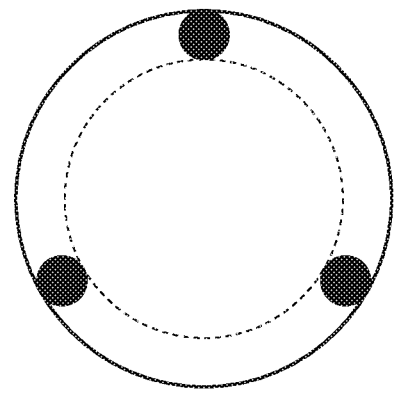
FIG. 36D

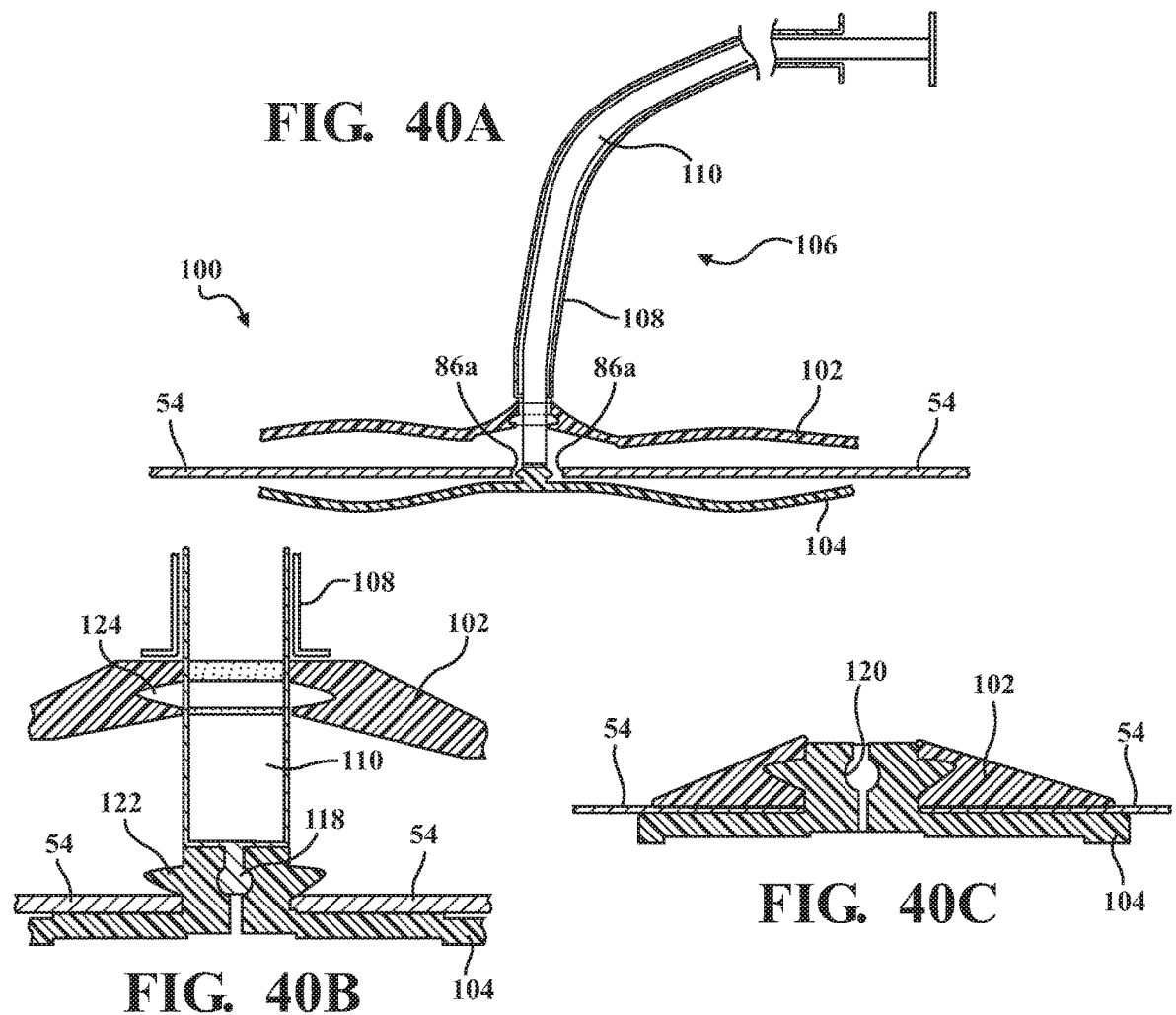
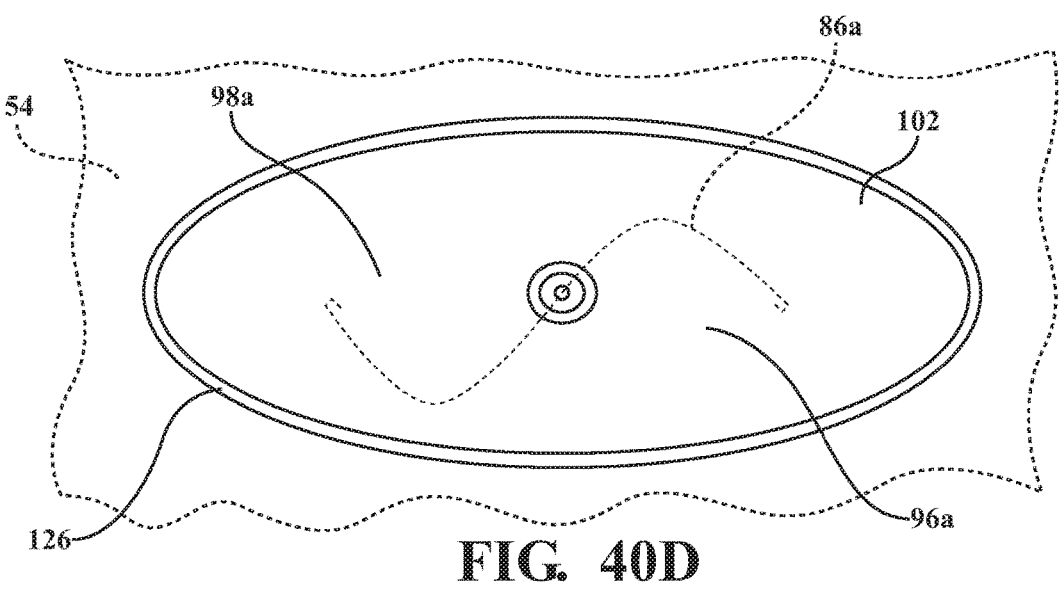

FIG. 43A
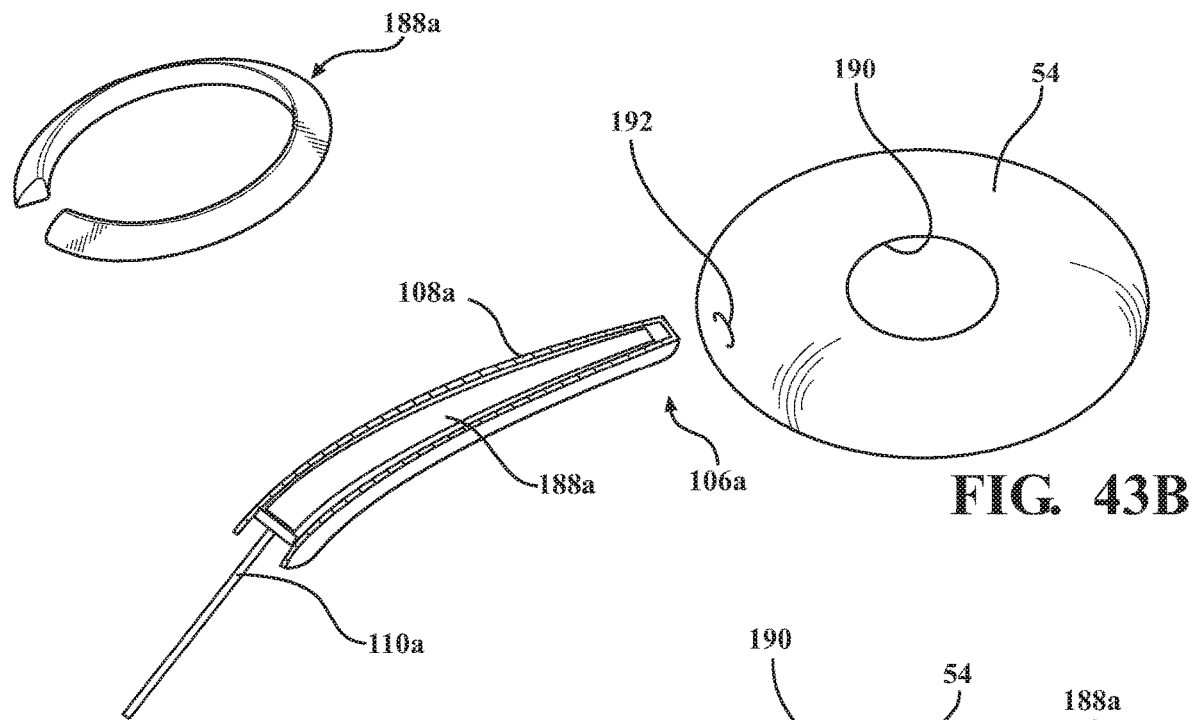
FIG. 43B
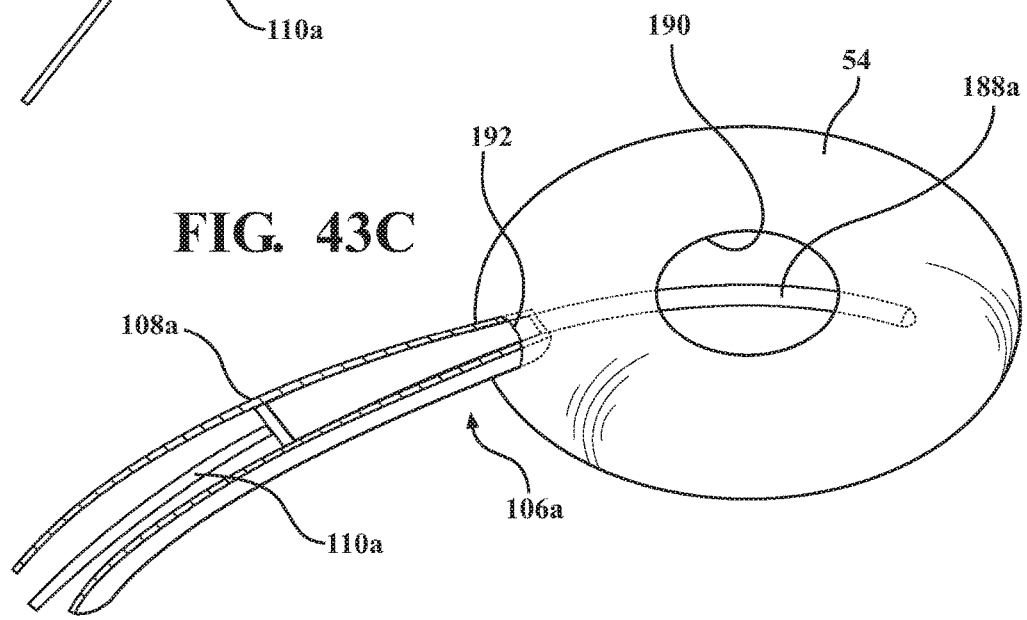
FIG. 43C
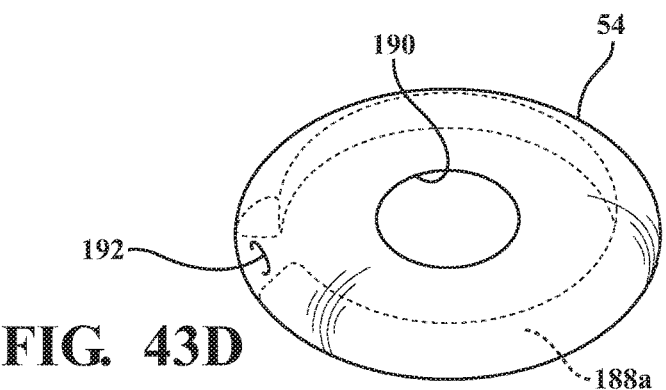
FIG. 43D

INTRAOCULAR OPTIC ASSEMBLY

CROSS-REFERENCE TO RELATED APPLICATIONS

This application is a divisional of U.S. patent application Ser. No. 16/355,882, for an ACCOMMODATING INTRAOCULAR LENS ASSEMBLY, filed on 18 Mar. 2019; which claimed the benefit of U.S. Provisional Patent Application Ser. No. 62/097,052 for an ACCOMMODATING INTRAOCULAR LENS ASSEMBLY, filed on 20 Mar. 201; which also was a continuation-in-part of U.S. patent application Ser. No. 14/979,449, for an ACCOMMODATING INTRAOCULAR LENS ASSEMBLY, filed on 27 Dec. 2015 (now U.S. Pat. No. 10,265,163, issued 23 Apr. 2019); U.S. patent application Ser. No. 14/979,449 also claimed the benefit of U.S. Provisional Patent Application Ser. No. 62/097,052 for a POST SURGERY MODIFIABLE DYNAMICALLY ACCOMMODATING INTRA-OCULAR LENS IMPLANT, filed on 27 Dec. 2014. All four applications are hereby incorporated by reference in their entireties.

BACKGROUND

1. Field

The present disclosure relates to structures positionable in a human eye such as intraocular lens arrangements, drug delivery systems, sensor holders, and glaucoma treatment devices.

2. Description of Related Prior Art

Prosthetic intra-ocular lenses (IOLs) are routinely implanted following cataract extraction in human eyes and have grown in sophistication in order to provide better functional visual acuity with fewer troublesome distortions, reflections and aberrations to images focused on the retina. However, the natural lens retains distinct advantages over currently available IOLs. One such quality is the ability to alter its optical power to allow clear focusing on near as well as distant objects through human volition in tandem with contraction of the ciliary muscle of the eye. The physiological mechanism whereby the human eye voluntarily alters its focal point from distance to near is termed "near-accommodation" and a prosthetic lens implant that seeks to perform this function is termed an Accommodating IOL or AIOL. Several designs have been proposed in the prior art for AIOLS that attempt to achieve the variable focus distance of the youthful natural lens but all have significant limitations.

U.S. Pat. Pub. No. 2005/0027354 discloses a PRIMARY AND SUPPLEMENTAL INTRAOCULAR LENS. The intraocular lens system includes a primary intraocular lens configured to correct vision in a patient, and a supplemental intraocular lens configured to modify the correction provided by the primary intraocular lens. The supplemental intraocular lens, which is substantially completely diffractive, is preferably ultrathin. The two lenses may be connected to, or separate from, one another. The supplemental intraocular lens may be implanted at the same time as the primary intraocular lens, or added later.

U.S. Pat. Pub. No. 2008/0288066 discloses a TORIC SULCUS LENS. There is disclosed therein a "piggyback" cylindrical (toric) intraocular lens for placement in front of an accommodating or standard intraocular lens that is already in the capsular bag of the eye. This additional lens is placed in the sulcus, which leaves a significant space between the two lenses, particularly if the lens in the capsular bag is vaulted backwards.

U.S. Pat. No. 8,425,597 discloses ACCOMMODATING INTRAOCULAR LENSES. Intraocular lenses for providing accommodation include an anterior optic, a posterior optic, and a lens structure. In one such lens, the lens structure comprises an anterior element coupled to the anterior optic and a posterior element coupled to the posterior optic. The anterior and posterior elements are coupled to one another at a peripheral region of the intraocular lens. The intraocular lens may also includes a projection extending anteriorly from the posterior element that limits posterior motion of the anterior optic so as to maintain a minimum separation between anterior optic and an anterior surface of the posterior optic.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

An AIOL can include a first lens, a first plurality of stanchions, a second lens, and a second plurality of stanchions. The first lens can have a first anterior side and a first posterior side and a first center disposed between the first anterior side and the first posterior side. A central optic axis can extend through the first center. The first plurality of stanchions can each respectively extend a first distance between a first base end and a first distal end. The plurality of first base ends can be disposed in spaced relation to one another about a first arcuate periphery extending in a first plane. The first distal ends can be disposed about a second arcuate periphery extending in a second plane. The first plane can be spaced from the second plane in a posterior direction along the central optic axis. The first arcuate periphery can have a greater radius than the second arcuate periphery. The first lens can be connected with each of the plurality of first distal ends. The second lens can have a second anterior side and a second posterior side and a second center disposed between the second anterior side and the second posterior side. The second anterior side can confront the posterior side of the first lens. The central optic axis can pass through the second center. The second plurality of stanchions can each respectively extend a second distance between a second base end and a second distal end. Each of the plurality of second base ends can be disposed in spaced relation to one another about a third arcuate periphery extending in a third plane. The second distal ends can be disposed about a fourth arcuate periphery extending in a fourth plane. The third plane can be spaced from the fourth plane along the central optic axis. The third arcuate periphery can have a greater radius than the fourth arcuate periphery. The second lens can be connected with each of the plurality of second distal ends. Each of the first plurality of stanchions can be fixed with one of the second plurality of stanchions at the respective first base end and the respective second base end to define a plurality of stanchion pairs. Compression at the first arcuate periphery and the third arcuate periphery can induce movement of the first lens and the second lens apart from one other. The compression can be transmitted through the first plurality of stanchions and the second plurality of stanchions.

According to other features, each of the first plurality of stanchions can be straight over at least most of the first distance and each of the second plurality of stanchions is straight over at least most of the second distance. For at least one of the stanchion pairs, a length between the first distal end of the stanchion of the first plurality of stanchions and the second distal end of the stanchion of the second plurality of stanchions may not be greater than an outside diameter of at least one of the first lens and the second lens. The length may not be greater than the outside diameters of both of the first lens and the second lens.

In other features, for at least one of the stanchion pairs, a length between the first distal end of the stanchion of the first plurality of stanchions and the second distal end of the stanchion of the second plurality of stanchions may be greater than an outside diameter of at least one of the first lens and the second lens. The length may be greater than a perimeter of the at least one of the first lens and the second lens.

According to additional features, each of the first plurality of stanchions can be straight over at least most of the first distance and each of the second plurality of stanchions is straight over at least most of the second distance. For at least one of the stanchion pairs, the straight portion of the stanchion of the first plurality of stanchions and the straight portion of the stanchion of the second plurality of stanchions can be interconnected at an intersection of the respective first base end and the respective second base end. A thickness of the intersection can be greater than a combination of a thickness of the straight portion of the stanchion of the first plurality of stanchions and a thickness of the straight portion of the stanchion of the second plurality of stanchions. The intersection can be bulbous and spherical.

According to other features, for at least one of the stanchion pairs, a length is defined between the first distal end of the stanchion of the first plurality of stanchions and the second distal end of the stanchion of the second plurality of stanchions and wherein a cross-sectional area of the at least one of the stanchion pairs can be substantially constant along the length. The stanchion of the first plurality of stanchions and the stanchion of the second plurality of stanchions can cross-over one another in a plane normal to the central optic axis. The stanchion of the first plurality of stanchions and the stanchion of the second plurality of stanchions can cross-over one another at a point in the plane that is further from the central optic axis than respective outside diameters of both of the first lens and the second lens.

In other features, the first lens can have a first outside diameter and the second lens can have a second outside diameter. The first outside diameter can be greater than the second outside diameter. The first plurality of stanchions and the second plurality of stanchions can be elastically wrappable around the second outside diameter prior to insertion of the AIOL in an eye.

A method of elastically deforming the AIOL described above, prior to insertion of the AIOL in an eye, can include rotating the first lens and the second lens relative to one another about the central optic axis and thereby drawing the first plurality of stanchions and the second plurality of stanchions in between the first lens and the second lens. The method can also include folding, after the rotating, the AIOL in half while retaining the first plurality of stanchions and the second plurality of stanchions in between the first lens and the second lens.

A method of elastically deforming the AIOL described above, prior to insertion of the AIOL in an eye, can include rotating the first lens and the second lens relative to one another about the central optic axis and thereby wrapping the first plurality of stanchions and the second plurality of stanchions around one of the first lens and the second lens. The method can also include folding, after the rotating, the AIOL in half while retaining the first plurality of stanchions and the second plurality of stanchions wrapped around the one of the first lens and the second lens.

A method of modifying a capsular bag of an eye can include initiating a continuous meandering incision in the capsular bag at a starting point. The method can also include completing the continuous meandering incision, after the initiating, from the starting point and over a tortuous path to an end point. The method can also include retaining, after the completing, at least one flap in the capsular bag, an edge of the at least one flap defined by the continuous meandering incision.

According to additional features, the completing action of the method of modifying a capsular bag can be further defined as completing the continuous meandering incision, after the initiating, from the starting point and over the tortuous path to the end point, wherein the starting point and end point are the same point, whereby the continuous meandering incision is endless. Alternatively, the completing action of the method of modifying a capsular bag can be further defined as completing the continuous meandering incision, after the initiating, from the starting point and over the tortuous path to the end point, wherein the starting point and end point are different points, whereby the continuous meandering incision is not endless. Alternatively, the completing action of the method of modifying a capsular bag can be further defined as completing the continuous meandering incision, after the initiating, from the starting point and over the tortuous path to the end point, wherein the starting point and end point are the same point, whereby the continuous meandering incision includes bends in opposite directions.

According to other features, the method of modifying a capsular bag can also include folding the at least one flap over a first portion of the capsular bag and mounting, after the completing, a seal to the capsular bag to inhibit leakage from the capsular bag through the incision, wherein at least a portion of a perimeter of the seal seals against a folding edge defined between the at least one flap and the first portion of the capsular bag. Alternatively, the method of modifying a capsular bag can further include mounting, after the completing, a seal to the capsular bag to inhibit leakage from the capsular bag through the incision, wherein a perimeter of the seal extends around the incision and the seal pinches adjacent edges of the incision. Alternatively, the method of modifying a capsular bag can further include implanting, in the capsular bag, against an equator of the capsular bag, a body that is elastically deformable into a toroid shape, wherein the body forms a toroid shape within the capsular bag and asserts a radially outward biasing force against the equator.

BRIEF DESCRIPTION OF THE DRAWINGS

The detailed description set forth below references the following drawings:

FIGS. 5A and 5B define split cross-sectional views showing the AIOL according to a second exemplary embodiment of the present disclosure position in an eye, wherein FIG. 5A shows the ciliary muscle in the relaxed condition and FIG. 5B shows the ciliary muscle in the contracted condition;

FIGS. 6A and 6B define split cross-sectional views showing the AIOL according to a third exemplary embodiment of the present disclosure position in an eye, wherein FIG. 6A shows the ciliary muscle in the relaxed condition and FIG. 6B shows the ciliary muscle in the contracted condition;

FIGS. 7A and 7B define split cross-sectional views showing the AIOL according to a fourth exemplary embodiment of the present disclosure position in an eye, wherein FIG. 7A shows the ciliary muscle in the relaxed condition and FIG. 7B shows the ciliary muscle in the contracted condition;

FIGS. 9A and 9B define split cross-sectional views showing the AIOL according to another exemplary embodiment of the present disclosure position in an eye, wherein FIG. 9A shows the ciliary muscle in the relaxed condition and FIG. 9B shows the ciliary muscle in the contracted condition;

FIG. 34 is a cross-sectional view taken through section lines 34-34 in FIG. 33;

FIG. 35 is a cross-sectional view analogous to the view of FIG. 34, but after the application of energy to portions of the lens to change the shape of the lens;

FIGS. 36A-36D are various patterns for the application of energy to portions of a lens to change the shape of the lens;

FIG. 40A is a side and partially cross-sectional view of the placement of a seal in a curvilinear incision;

FIG. 40B is a magnified portion of FIG. 40A;

FIG. 40C is a view analogous to FIG. 40B, but differs by showing portions of the seal when placement is complete;

FIG. 40D is a front view of a portion of capsular bag sealed with the seal shown in FIGS. 40A-40C;

FIG. 43A is a perspective view of an exemplary space-occupying element according to an embodiment of the present disclosure;

FIG. 43B is a first schematic view of insertion of the exemplary space-occupying element shown in FIG. 43A into a capsular bag;

FIG. 43C is a second schematic view of insertion of the exemplary space-occupying element shown in FIG. 43A into the capsular bag;

FIG. 43D is a front view of the exemplary space-occupying element shown in FIG. 43A positioned in the capsular bag;

DETAILED DESCRIPTION

Figure 1:
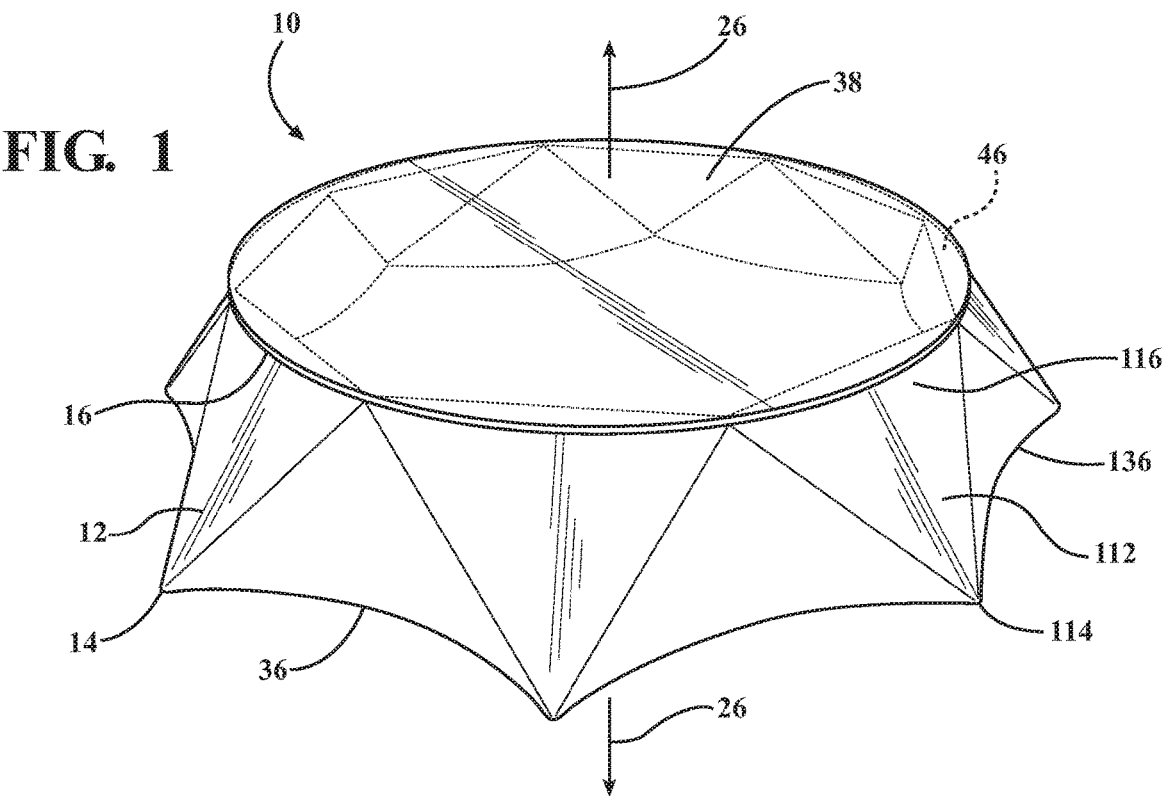
FIG. 1 is a perspective view of an AIOL according to an exemplary embodiment of the present disclosure.

A plurality of different embodiments of the present disclosure is shown in the Figures of the application. Similar features are shown in the various embodiments of the present disclosure. Generally, similar features across different embodiments have been numbered with a common reference numeral and have been differentiated by an alphabetic suffix. Also, generally, similar features in a particular embodiment have been numbered with a common two-digit, base reference numeral and have been differentiated by a different leading numeral. Also, to enhance consistency, the structures in any particular drawing share the same alphabetic suffix even if a particular feature is shown in less than all embodiments. Similar features are structured similarly, operate similarly, and/or have the same function unless otherwise indicated by the drawings or this specification. Furthermore, particular features of one embodiment can replace corresponding features in another embodiment or can supplement other embodiments unless otherwise indicated by the drawings or this specification.

The following terms are useful in the defining the operating environment of one or more embodiments of the present disclosure:

Intraocular Lens or "IOL" or intraocular optic or IOL optic refers to a prosthetic optical lens placed within the eye to allow better visual functioning of the eye;

"Conventional IOL" refers to an IOL that has a single fixed focal point (also known as a monofocal IOL);

"Near Accommodation" or "Accommodation" refers to a change in the focal point of the optical system of the human eye from fixation on distant objects (those further away than about 6 meters from the eye) to near objects (those closer than about 0.5 meters from the eye), the term "accommodation" also includes the act of focusing on objects in the intermediate range of 6 to 0.5;

"Ciliary Body" or "CB" refers to the Ciliary Body of the eye including the various neuromuscular elements comprising the structure commonly referred to as the Ciliary Muscle, as well as the connective tissue joining the muscular elements and forming attachments of the ciliary muscle to the sclera and to the zonules or suspensory ligaments of the lens capsule. The muscular tissue within the CB is generally of the type known as "smooth muscle". Many microscopic muscle cells are connected to each other via elastic connective tissue forming bundles or rings of muscle that contract and stretch as a result of the combined contraction of the constituent muscle fibers;

"Ciliary Body accommodation" or "CBA" refers to the anatomical and physiological changes initiated by the act of voluntary human accommodation, during CB accommodation, impulses from the brain are transmitted to the nerves supplying the ocular tissues so that at least one eye is directed to align its optic axis towards the object of visual fixation, when at least one eye fixates on an object of visual interest, subconscious cues create an approximate estimate of the distance of the object from the eye and CB accommodation is triggered to the appropriate approximate extent required for the image from the object to be sharply focused on the retina, a process of reiterative biofeedback occurs so that the degree of CB accommodation is matched to the required working distance for sharp focus of the image from the object that is being viewed, other physiological actions are also linked to CB accommodation such as convergence (inwards rotation of eyes to triangulate and focus on a near object) and miosis (constriction of pupils to increase visual depth of field);

"Lenticular accommodation" refers to the alteration in optical power of the youthful or pre-presbyopic human eye in response to CB accommodation, the natural human lens is also known as the crystalline lens. It is enclosed within the lens capsule which in turn is connected to the ciliary body via many zonules (also known as suspensory ligaments) that attach close to the peripheral equator of the lens capsule on its posterior and anterior surfaces and extend in a radial fashion, suspending the crystalline lens from the CB. CB accommodation results in increased relative curvature of the front and rear lens capsule surfaces (also known collectively as the capsular bag), and a forward shift in the optical center of the crystalline lens, lenticular accommodation occurs as a result of decreased radial tension in the zonules because CB accommodation causes a relative anterior shift of the ring formed by the center of radial suspension the zonules, the cross sectional diameter of the eyeball is less at the relatively anterior location of the CB ring during CB accommodation, therefore the tension in the zonules is decreased allowing the elastic crystalline lens to revert to a shape that is more rounded in its anterior and posterior curvatures;

"Ciliary Sulcus" Refers to the ring like space bounded posteriorly by the ciliary process and suspensory ligaments of the lens (zonules) and bounded anteriorly by the posterior surface of the iris, the ciliary sulcus is bounded peripherally by the soft tissues overlying the ciliary body, these soft tissues separate the ciliary sulcus from the muscular components of the ciliary body, specifically the circular or annular portions of the ciliary muscle, the meridional portions of the ciliary muscle lie more peripherally and are anchored at the scleral spur, the ciliary sulcus extends for 360 degrees at the base of the iris, is vertically oval in humans and decreases in diameter during CBA;

"UBM" or "Ultrasound biomicroscopy" refers to imaging studies of the eye which show characteristic biometric changes that occur during ciliary body contraction, for understanding of the intended working of embodiments of this present disclosure, it is necessary to define some biometric features that change during CBA:

SSD (sulcus-to-sulcus diameter)—distance between opposite points in the ciliary sulcus, this will vary between individuals due to normal anatomic differences depending on the axial location of the opposite points because the ciliary sulcus is oval instead of circular in the near accommodated state in comparison to the relaxed state as CBA reduces SSD, ICPA (Iris-ciliary process angle)—the angle between the plane of the iris and the direction of the ciliary process from between which the lens zonules extend to the equator of the capsular bag, ACA (anterior chamber angle)—the angle between the plane of the peripheral iris and the inner layer of the cornea where they meet close to the iris root;

"Annular muscle contraction" or "AMC" refers to the morphological changes occurring during the contraction and relaxation of an annular or sphincteric muscle, specifically, it relates to the shape changes of the round portion of the ciliary muscle during CBA, the ring shaped "round" portion of the ciliary muscle encloses a central opening known as a lumen, which forms the external boundary of the ciliary sulcus, when an annular muscle contracts its total volume remains essentially unchanged but the circle surrounding the lumen in the plane of the lumen constricts, each point lining the lumen moves in relation to its neighbor during contraction and relaxation so that there are no two points that remain stationary relative to each other;

"Elastic biological surface" or "EBS" refers to a flexible membrane that forms the outside enclosure of an annular muscle or other elastic biological surface such as the capsule (or capsular bag) of the crystalline lens;

"Point-to-point contraction linking" or "PPCL" refers to the ability of a device to remain in contact with an elastic biological surface during the entire cycle of contraction and expansion without slipping at its contact points and without offering sufficient resistance to impede movement or cause damage by abrasion or penetration, for a device to be usefully coupled to an annular muscle (such as that found in the CB) it is essential for the device to offer in a predictable manner only as much resistance to movement as is necessary to convert the contraction of the muscle (in this case the contraction associated with CBA) into useful work (in this case IOL accommodation or "IOLA"), effective PPCL depends on critical design elements related to the points of contact of the device to the elastic biological surface, the features in point of contact design to achieve effective PPCL include:

distribution and location—Points of contact should be located around a center of movement that is also the center of movement of the elastic biological surface, number—The points of contact should be numerous enough to maintain stable attachment during motion and distribute resistance evenly across biological surface, at least eight contact points can be desirable for PPCL to a device within the lumen of an annular muscle, too many points of contact if large will limit movement by causing crowding and if small, may impede biological function by causing scarring, size—large contact points in contact with elastic biological surfaces such as the ciliary sulcus or capsular bag will present resistance against contraction or expansion of those surfaces, the continuous expansion and contraction of an annular muscle (even with its surrounding connective tissue) against an inelastic surface is likely to cause damage to biological tissues by abrasion and deposition of eroded tissues, contact points that are too small are likely to cause damage by perforation or penetration into biological tissue, profile—curved contact points offer a variable surface area and some degree of "rocking" during expansion and contraction which protects biological tissue and reduces scarring, multiple protrusions are vulnerable to becoming entangled during implantation, becoming damaged or causing damage to biological tissue;

"Haptic Vaulting" when used in relation to IOLs refers to forward or backward movement of IOL optic in the direction of the visual axis relative to the distal ends of its haptics, in prior art Haptic vaulting is envisioned as a mechanism for achieving IOLA in capsular bag fixated IOLs in response to decreasing diameter of the capsular bag which may vertically compress the haptic ends, Haptic Vaulting may occur surreptitiously in even prior art conventional or monofocal IOLs, depending on nature and placement of the haptics within a fibrosed or contracted capsular bag;

"Rigid Vaulting" when used in relation to IOLs refers to forward or backward movement of IOL optic in the direction of the visual axis relative to the optical nodal point of the eye in response to mechanical forces within the eye, specifically, this relates to movement of an IOL fixed within a capsular bag (IOL-capsule diaphragm) in response to movements of the entire capsular bag caused by:

contraction or relaxation of the zonules attached to the capsular bag secondary to ciliary muscle contraction, variations in fluid pressure (from aqueous humor or vitreous humor) between the anterior and posterior surfaces of the IOL-capsule diaphragm, gravitational shifting of IOL in response to changes in eye position (Rigid Vaulting is widely believed to occur surreptitiously in prior art conventional or monofocal IOLs, but to a variable and unpredictable extent and therefore cannot be relied on to provide useful degree of IOLA);

"Pseudo-accommodation" refers to the retention of some functional unaided near vision in combination with good distance vision following cataract extraction in patients who do not have IOLA, in patients who have a fixed focal length IOL implanted, whose power is set for clear distant vision, it is the ability of such patients to have better than expected (although still limited) near vision (without reading glasses), its existence is due to the following factors or fortuitous conditions:

Pinhole effect—increased depth of field caused by decreasing aperture of the pupil during CBA and in conditions of high illumination, this effect may be enhanced in some lenses whose central curvature is higher than peripheral so that when the peripheral cornea is curtained off by the constricting pupil, the overall focus of the lens because closer, relying on the pinhole effect has the disadvantage of reducing amount of light available to the eye and hence compromising the overall quality of vision, Aspheric optic property of the IOL (Lens has more than one major focal point). This may be intentional or serendipitous: Multifocal IOL design including pupil independent (diffractive lenses, aspheric curvatures) and pupil assisted (linked to pupillary constriction like the pinhole effect but accentuated by the IOL deliberately having a higher power in its central curvature, and Fortuitous/serendipitous optical effects presenting a secondary near image due to lens tilt (induced lenticular astigmatism) and corneal myopic astigmatism (Asymmetry of corneal curvature or tilting of the IOL can cause astigmatism, for example in which vertical lines far away, are seen better than horizontal lines, with the reverse holding try for near, since writing tends be composed of vertical and horizontal lines, people with just the right degree of astigmatism learn to decode the otherwise blurred near vision), and Limited accommodation due to IOL forward movement during CBA which may occur with any IOL implanted in elastic capsular bag with intact zonular attachments where the IOL-capsular bag complex moves forward during CBA increasing the effective power of the IOL and causing its focal point to move from distance to near, younger post cataract patients are often seen to have less need for reading glasses than expected when their (non-accommodating) IOLs have been selected for distant focus in both eyes, it is thought that the combination of a vigorous scarring response (causing the posterior capsule to bind firmly around the edge of the lens, and still strong ciliary muscles, allows the IOL to move forward in a way similar to the natural lens, this effect is usually not of sufficient extent to obviate the need for reading glasses;

"Monovision" refers to the illusion of good near and far vision obtained by implanting a monofocal IOL in one eye whose focal point is for distance and another monofocal IOL in the fellow eye whose focal point is for near. Monovision can also achieve a form of pseudo-accommodation so that when both eyes are used together, one provides good monocular distance vision and the other provides acceptable monocular near vision if the brain is able to adapt to this method of correction, this technique is often not well tolerated and causes reduction in stereoscopic vision, the patient is able to use each eye for its working distance (distance or near) although this does not represent true accommodation;

"IOL accommodation" or "IOLA" refers to a change in the optical focal point of an intraocular lens (hereafter IOL) from a sharp distant focus to a sharp near focus (and intermediate distances when the object of visual attention is in between) in an attempt to simulate is lenticular accommodation in response to CB accommodation, IOL accommodation is not equivalent to the IOL multifocality achieved by multifocal IOLs described immediately below;

"Multifocal IOL" or "MFIOL" refers to an IOL designed to have multiple simultaneous focal point, MFIOLs offer a degree of pseudo accommodation by having multiple focal powers or curvatures molded into a single IOL resulting in images of objects at more than one working distance becoming focused simultaneously on the retina, however, the simultaneous presentation of more than one image by the IOL causes degradation and compromise of each of the images as well as troublesome visual symptoms of halos, glare, ghost images collectively known as dysphotopsia, the providential persistence of pupillary miosis associated with CB accommodation can be utilized to preferentially select the central portion of the IOL curvature for near focusing and allow input from the peripheral lens curvature when CB accommodation is relaxed, and the pupil becomes relatively dilated, however, this type of "pinhole effect" also compromises overall quality of the images and multifocal IOLs in general have limited utility because CB accommodation does not result in true IOL accommodation, the increased range of focus depth of field presented by a static multifocal IOL is offset by lower image quality and visual aberrations, the eye and brain have to learn to ignore the images that are not useful for the current working distance and therefore there is compromise in overall vision quality and comfort;

"Haptic" refers to an arrangement of structural elements whose primary purpose is to hold, support, maintain and fixate one or more other distinct elements or device within the eye, where the device serves a biologically important function;

"Haptic Passenger" refers to a functionally important device supported by the haptic, examples of Haptic Passengers and their associated functions include an optical lens system, a reservoir, depot or container for a therapeutic substance or drug, a diagnostic instrument or sensor;

"IOL haptic" or refers to a structural element of an IOL designed to hold an IOL in place within the eye, such as a haptic whose haptic passenger is a lens;

"IOL optic" refers to the optically active component of the IOL having light transmitting refractive power, such as the haptic passenger for an IOL haptic;

"Capsular bag" or "bag" refers to the partially elastic biological membrane which normally contains the lentil shaped crystalline lens of the eye between a front surface (anterior capsule) and a back surface (posterior capsule) which join at the equator of the capsular bag from which equator the lens is suspended from and connected to the processes of the ciliary body by zonules (or suspensory ligaments of the lens), the capsular bag is opened during cataract surgery to remove the cataractous lens by making a roughly circular opening in its anterior capsule, the capsular bag has traditionally been the desired location in which to place an IOL after cataract extraction, the IOL is normally placed through the anterior capsular opening or "rhexis" so that its spring like supporting haptics rest in or close to the equator of the bag, suspending the optic of the IOL within and perpendicular to the visual axis;

"Capsulorhexis" or "rhexis" refers to the surgical opening made in the capsular bag and is a vital step in modern cataract surgery, it is necessary to access the cataract for removal and to insert an IOL if it is to be placed in the capsular bag, and the terms "rhexis" and "incision" are used interchangeably herein;

"Posterior capsular fibrosis" or "Posterior capsular opacification" (PCO) refers to the migration and proliferation of fibroblast inside and around the remnants of the capsular bag following cataract surgery, in addition to reducing vision, the scar tissue formed by these fibroblasts causes scarring and contracture of the capsular bag resulting in loss of its elastic properties, posterior capsular fibrosis occurs to at least some extent in the majority of patients following cataract despite various precautions commonly taken to reduce it, contracture of the capsular bag can cause tilt or displacement of an IOL in contact with the bag and will limit post-operative capsular bag movement in response to CBA, the severity of posterior capsular fibrosis is unpredictable but often warrants YAG laser capsulotomy after surgery to break open the capsule when it interferes with vision, the behavior of the capsular remnants following YAG laser capsulotomy is even more unpredictable, this means that any AIOL that relies on capsular bag contraction for functioning is unlikely to be successful because CBA cannot be reliably translated into IOLA by the post-surgical capsular bag;

"Accommodating IOL" or "AIOL" refers to a prosthetic lens or IOL that seeks to restore the function of lenticular accommodation (other than by pseudo-accommodation or monovision) in a patient whose crystalline lens has been removed;

"Simple lens" refers to the concave and convex cross sections depicted in optical drawings and ray diagrams shown commonly in physics textbooks, wherein the convex or concave surfaces enclose a medium whose refractive index is different to that of the media in front and behind the lens, although its front and rear surfaces are separated such a lens has a point (which can actually lie outside the body of the lens) known as the optical center of the lens whose location and optical properties can be described in an idealized fashion by "Thin Lens Theory", and in a more complex, and potentially more accurate fashion by "Thick Lens Theory", the power of such a lens is normally fixed and does not change because the lens is solid and static, the power of a particular simple lens can be made different to that of another by altering one or both of the front and rear curvatures or the refractive index of the medium behind and/or in front of the lens;

"Compound lens" refers to a lens composed of two or more simple lenses whose overall optical parameters can be varied by varying the power of each component lens, varying the separation between the optical centers of the component lenses, and varying other spatial relationship (such as tilt and alignment) between the optical centers or surfaces of the component lenses;

"Flexible lens" refers to a lens composed of an optical medium which is fluid or gel like in mechanical property, and of essentially constant volume, and whose volume is contained and bounded across at least part of its surface by an elastic or flexible membrane, the power of a flexible lens can be varied by shape change of the fluid or gel like medium when such shape changes result in variations in curvature of the flexible membrane when the membrane lies across the visual axis, variation in separation of the front and back surfaces, and variation in location of optical center of lens;

"Biological lens" refers to a lens with front and back surfaces whose body is composed of regions of varying refractive index without clear demarcation or interface between the zones, the regions may be distributed so that the gradient in refractive index varies perpendicular to its optic axis (refractive index changing from center to periphery in a concentric radial fashion) and/or varies in the line of the optic axis so that the refractive index is maximum at the front surface, back surface or center of the lens, variations of the power of a biological lens can be achieved by a spatial redistribution of the regions of high and low refractive indices and may be achieved by overall change in the shape of the lens when it is contained within a flexible membrane or redistribution of the optical centers of the regions of different refractive index without overall shape change of the external boundaries of the lens capsule, resulting in a shifting of the optical center of the lens;

"Neo-biological lens" refers to a lens composed of material whose refractive index can be varied be electronic or photo-chemical means either across the entire material of the lens, or selectively in certain regions; and "Higher Order Aberrations" or "HOA" relates to imperfections of focusing of a nature more complex than lower order optical aberrations such as spherical error and astigmatism, clinically important examples of HOA include spherical aberration, coma and trefoil, correction of HOA can improve visual quality and satisfaction following ocular surgery.

The exact nature and relative importance of various physiological mechanisms active in the human eye during the act of accommodation is controversial. The theory of Helmholtz appears to be the most favored. It is agreed that contractions of the ciliary body/muscle occur in response to neural signals from the brain when accommodation is voluntarily or reflexly initiated. It is also agreed that in the youthful eye, this contraction causes several mechanical changes that result in the optical dioptric power of the lens system becoming more positive and so shifting the focal point of the lens closer to the person. The optical power change is thought to result from an anterior shift of the overall optical center of the lens closer to the cornea and an increase in curvature of the anterior and/or posterior refracting surfaces of the lens (necessitated by the requirement to maintain constant volume within the enclosing capsular bag) when the lentil shaped lens decreases in circumference at its attachment points (zonular fibers) in the plane roughly perpendicular to the visual axis.

In practice, other subtle changes may also contribute to a lesser extent such as constriction of the pupil to induce a pin-hole effect to increase depth of field—pseudo accommodation, shift of the constricted pupillary center away from the relaxed pupillary center to preferentially select a new optical line of site within the eye of different refractive power, and change in lens shape may cause shifting of relative position within the lens, of areas of differing pliability, elasticity and refractive index to cause a change in overall power.

For AIOL design a clear understanding of the anatomical changes occurring in the eye during CBA is desirable. In some species, CBA results in muscular activity that alters the curvature of the cornea or the length of the eyeball amongst other changes, but in humans, alterations of the shape and location of the crystalline lens appear to be the main mediators of accommodation.

When CBA is initiated in humans, at least three muscular sub systems within the ciliary body are activated. First, there is an annular or circular component—a sphincter muscle in the shape of a toroid in a plane approximately perpendicular to the visual axis, located internally to the scleral coat of the eye within the partially elastic parenchyma or connective tissue of the CB. This annular component contracts on accommodation so that the toroid becomes smaller in diameter and thicker in its cross section while the plane of the toroid moves closer to the front of the eye in the line of the visual axis. This contraction releases tension on the lens zonules and capsular bag, thereby causing forward movement of the optical center of the lens and a reduction in the equatorial diameter of the lens capsule.

Second, meridional or longitudinal components that run in approximately parallel to each other slight curve under the sclera connection their relatively stationary attachment on the sclera at one end to the pars plana of the ciliary body at the other end. The effect of contraction of these fibers is to pull the area of attachment of lens zonules anteriorly along the interior surface of the eyeball as it approaches the cornea. The anatomy of the anterior eyeball is such so that this movement results in release in tension of the lens zonules, especially those connecting to the front surface of the lens capsule so that the lens returns to a more rounded shape and its optical center moves forward. The annular fibers of the ciliary muscle lie in a ring separated from the sclera and eyeball by the longitudinal fibers so that the contraction of the longitudinal fibers mechanically facilitates the contraction of the annular components by occupying and increasing the space between the outer aspect of the ring muscles and the sclera.

Third, oblique fibers that run a semi-spiral course under the sclera of the eyeball. They likely act as slings to reduce forces that might inwardly detach the pars plana of the ciliary body and prevent wrinkling of the pars plana of the ciliary body during CBA.

Although the ciliary muscle is usually depicted in cross section, it is actually a complex 3-D structure that is fixed at its outside margin to the sclera of the eyeball and whose inside margin suspends the zonules which connect to the capsular bag. Different species have at least three types of muscle fibers within the ciliary muscle. The exact contribution of the various mechanisms linked to accommodation are not fully known but for the purpose of at least some embodiments of the present disclosure the important points are that when contracted during accommodation the ciliary muscle concentrates into a toroid which decreases in inside diameter, increases in cross sectional area, and moves forward in the plane perpendicular to visual axis with regards to the location of its center of volume.

Contraction of the ciliary muscle leads to changes in the three dimensional shape of the lens capsule as well as displacement of the optical center of the lens in relation to the overall optical center of the eye itself. This displacement alters the overall focal point of the eye allowing variability of focus from distance to near objects.

When accommodation is relaxed in the human eye, outward radial pull via tension in the suspensory ligaments (zonules) of the lens leads to an increase in the circular diameter of the space contained within the lens capsule in the plane approximately perpendicular to the visual axis and path of light from distant objects to the central retina of the eye. The act of accommodation causes the ciliary muscle of the eye to contract which releases tension in the suspensory lens ligaments resulting in reduced diameter of the lens in the visual plane and changes in the anterior and posterior surface curvatures of the lens as well as shifting of the optical center of the lens which result in increased convex diopteric power of the lens and consequently of the whole optical system of the eye allowing near objects to be focused on the retina.

The crystalline lens of the eye is normally flexible and is suspended within an elastic capsule. This capsule has to be penetrated to remove the cataractous lens.

The shape of the lens capsule and enclosed lens in its natural state depends on the interaction between the elastic nature of the capsule and also (a) the tension in the supporting zonules whose force and direction is varied by contraction of the ciliary muscle, (b) resistance and pressure from the vitreous humor against the posterior capsule surface, (c) forces on the anterior surface of the lens capsule from aqueous humor and iris, (d) gravity, and (e) resistance to deformity of the contents of the lens capsule, normally the crystalline lens.

One or more embodiments of the present disclosure utilize biometric changes occurring during CBA. The primary biometric changes utilized are reductions in the sulcus-to-sulcus diameter (SSD), the anterior chamber depth (ACD), the iris-ciliary process angle (ICPA), and the iris-zonula distance (IZD, or posterior chamber depth). Indirect or secondary biometric changes occurring during CBA that can be utilized in one or more embodiments of the present disclosure include reductions in the ciliary process-capsular bag distance (CP-CBD) decreases and the ciliary ring diameter (CRD).

Although there is considerable variability in the exact measured mean values for the various anatomical distance and angles compared in the relaxed and near accommodated state, this is not surprising given the normal anatomical variations between studied individuals as well as the variety of instruments and techniques used in different studies. Additionally, the resolution of the current technology is still sub optimal, as are agreements in precise location of landmarks. Because of the above-mentioned factors, comparison of the various studies shows a wide variability of the mean measured values in both the relaxed and near accommodated state, as well as large standard deviations in the mean difference values. This results in low confidence in the statistical significance of the mean differences in many of the studies. However, at least some embodiments of the present disclosure assume that there are some consistent and predictable variations in measured anatomical parameters during near accommodation including (a) a decrease in the SSD (sulcus-to-sulcus diameter) from approximately 11 mm to approximately 10.5 mm, (b) a decrease in the ICPA (Iris-ciliary process angle) from approximately 40 degrees to approximately 22 degrees, (c) a decrease in the ACA (anterior chamber angle) from approximately 32 degrees to approximately 28 degrees, (d) a decrease in the distance from the ciliary sulcus to the apex of the cornea caused by movement of the plane of the ciliary sulcus anteriorly along the visual axis, and (e) an increase in the diameter of the circular portion of the ciliary muscle. One or more embodiments of the present disclosure can use the above anatomical changes to mechanically link CBA to IOLA in a manner superior to the prior art.

Figure 2:
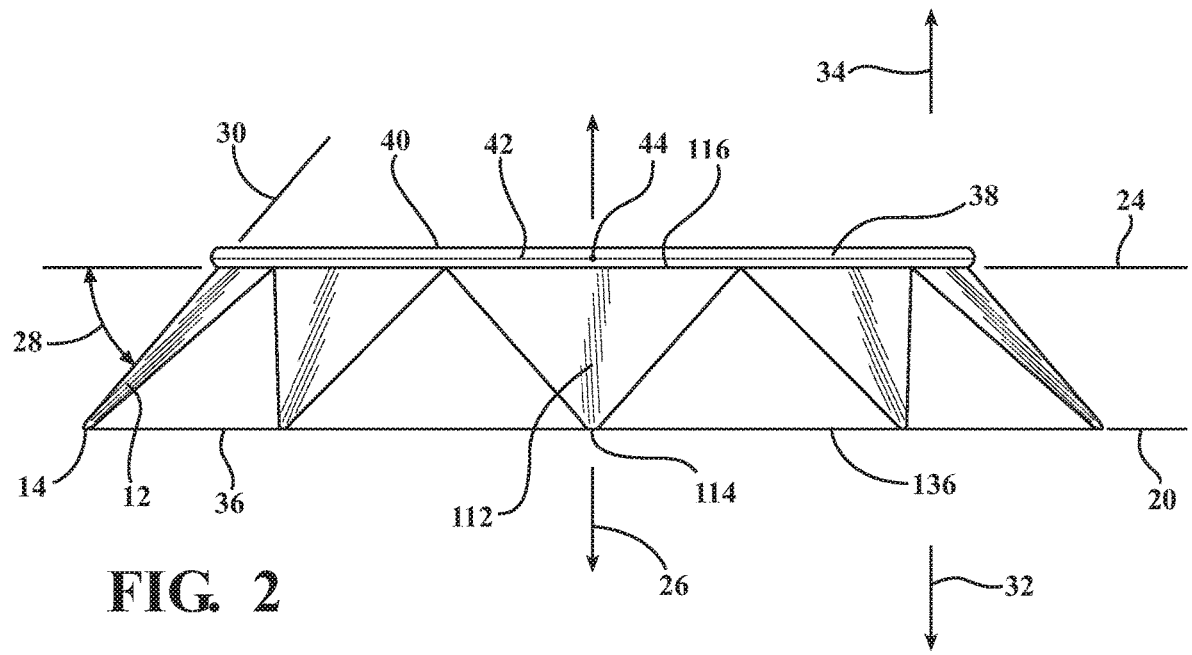
FIG. 2 is a side view of the exemplary embodiment of the present disclosure.
Figure 3:
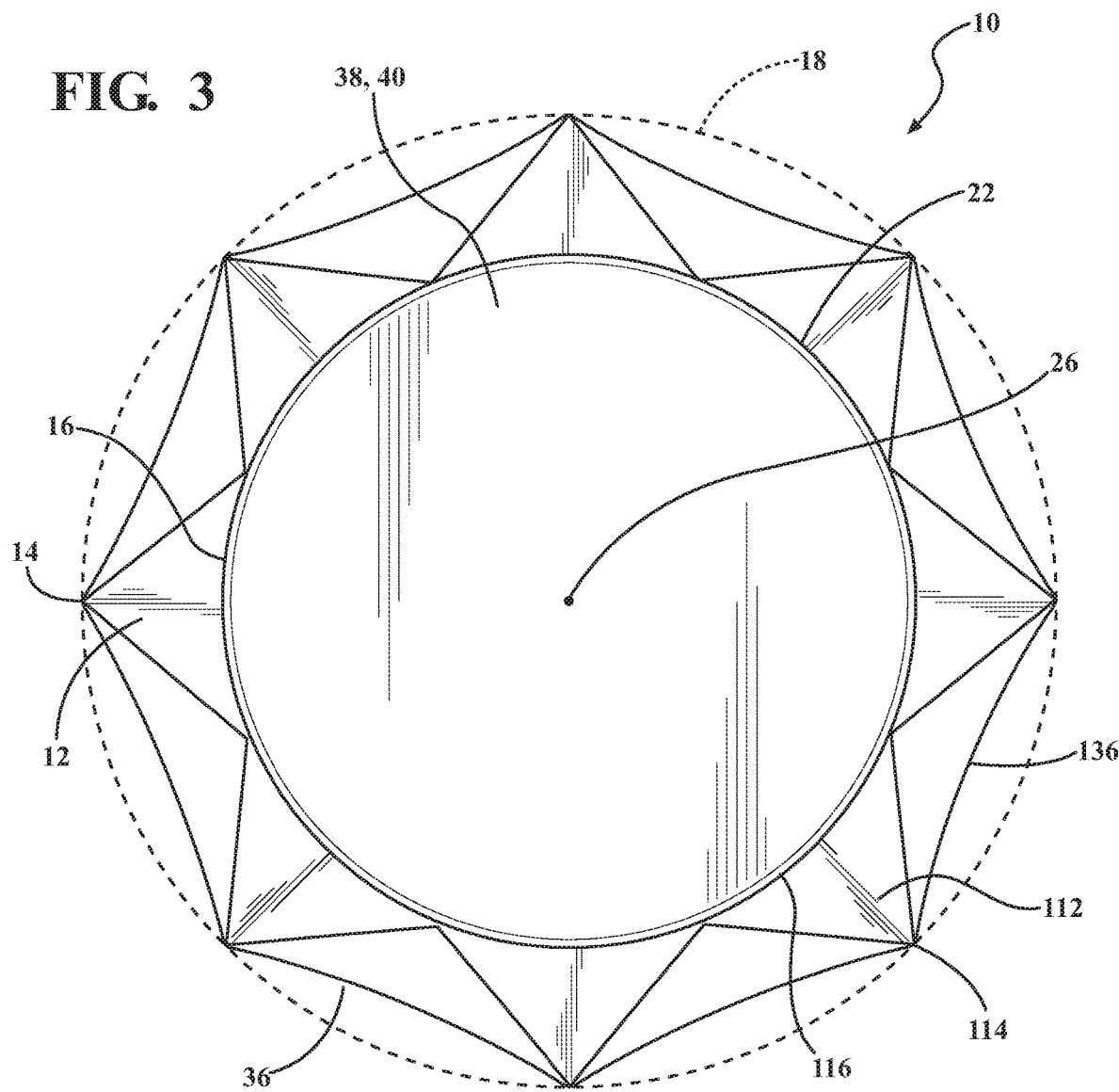
FIG. 3 is a top view of the exemplary embodiment of the present disclosure.

The present disclosure, as demonstrated by the exemplary embodiments described below, can provide an AIOL positionable in the ciliary sulcus. In a first embodiment, shown in FIGS. 1-3, an AIOL 10 can include a plurality of stanchions, such as stanchions 12, 112. Each of the plurality of stanchions can extend between a base end and a distal end. The stanchion 12 extends from a base end 14 and a distal end 16. The stanchion 112 extends from a base end 114 and a distal end 116. The plurality of base ends can be disposed in spaced relation to one another about a first arcuate periphery 18 extending in a first plane. The first plane is referenced at 20 in FIG. 2. The distal ends can be disposed about a second arcuate periphery 22 extending in a second plane. The second plane is referenced at 24 in FIG. 2. The first plane 22 can be spaced from the second plane in a posterior direction along a central optic axis 26. The first arcuate periphery 18 can have a greater radius than the second arcuate periphery 22. The first arcuate periphery 18 and the second arcuate periphery 22 can both be centered on the optic axis 26.

The first arcuate periphery 18 can be positioned in the ciliary sulcus. The base ends can be bulbous and/or at least partially spherical. The plurality of stanchions can extend away from the base ends and the first arcuate periphery 18 toward the second arcuate periphery 22. In the exemplary embodiment, the plurality of stanchions can be wider at the distal end than at the base end. Each of the plurality of stanchions can progressively increase between a first width at the base end to a second width at the distal end in a third plane transverse to the central optic axis 26. The third plane is referenced at 30. Each of the plurality of stanchions can maintain a substantially constant second width (or thickness) in a fourth plane containing the central optic axis 26. The fourth plane is the plane of view of FIG. 2. Narrowing the stanchions proximate to the base ends can minimize the contact area between the assembly 10 and the ciliary sulcus. Also, maintaining a relatively thin cross-section in the fourth plane can be desirable as the space defined by the ciliary sulcus (between the iris and the ciliary muscle) can shrink during contraction of the ciliary muscle and the stanchions can be pinched during contraction of the ciliary muscle.

Each of the plurality of stanchions can extend away from the plane 24 in the posterior direction at an acute angle greater than twenty degrees and less than ninety degrees. The exemplary angle is referenced at 28 in FIG. 2. The posterior direction is referenced at 32 in FIG. 2. The anterior direction is referenced at 34 in FIG. 2.

The AIOL 10 can also include arcuate linking members extending along the first arcuate periphery 18, such as linking members 36, 136. The linking members are not required for all embodiments of the present disclosure but can be desirable for modulating the graph of CBA against IOLA. Duane's graph of accommodation with age is a well-established reference. The amplitude of accommodation is the increase in optical power that an eye can achieve in adjusting its focus. The "amplitude" is defined by a range of object distances for which the retinal image can be sharply. The larger the range of object distances, the larger the amplitude. The amplitude of accommodation is measured during an eye-examination. The closest that a normal eye can focus is typically about 10 cm for a child or young adult. Accommodation then decreases gradually with age, effectively finishing just after age fifty.

Duane's Curve shows that a pre-presbyopic individual (around age 40 or less) has a range or amplitude of accommodation of about 6 diopters or more. A diopter (us) is the unit of measurement of the optical power of a lens and is equal to the reciprocal of the focal length measured in meters (1/meters). It is thus a unit of reciprocal length. For example, a 2 diopter lens brings parallel rays of light to focus at ½ meter$^{-1}$.

Figure 23:
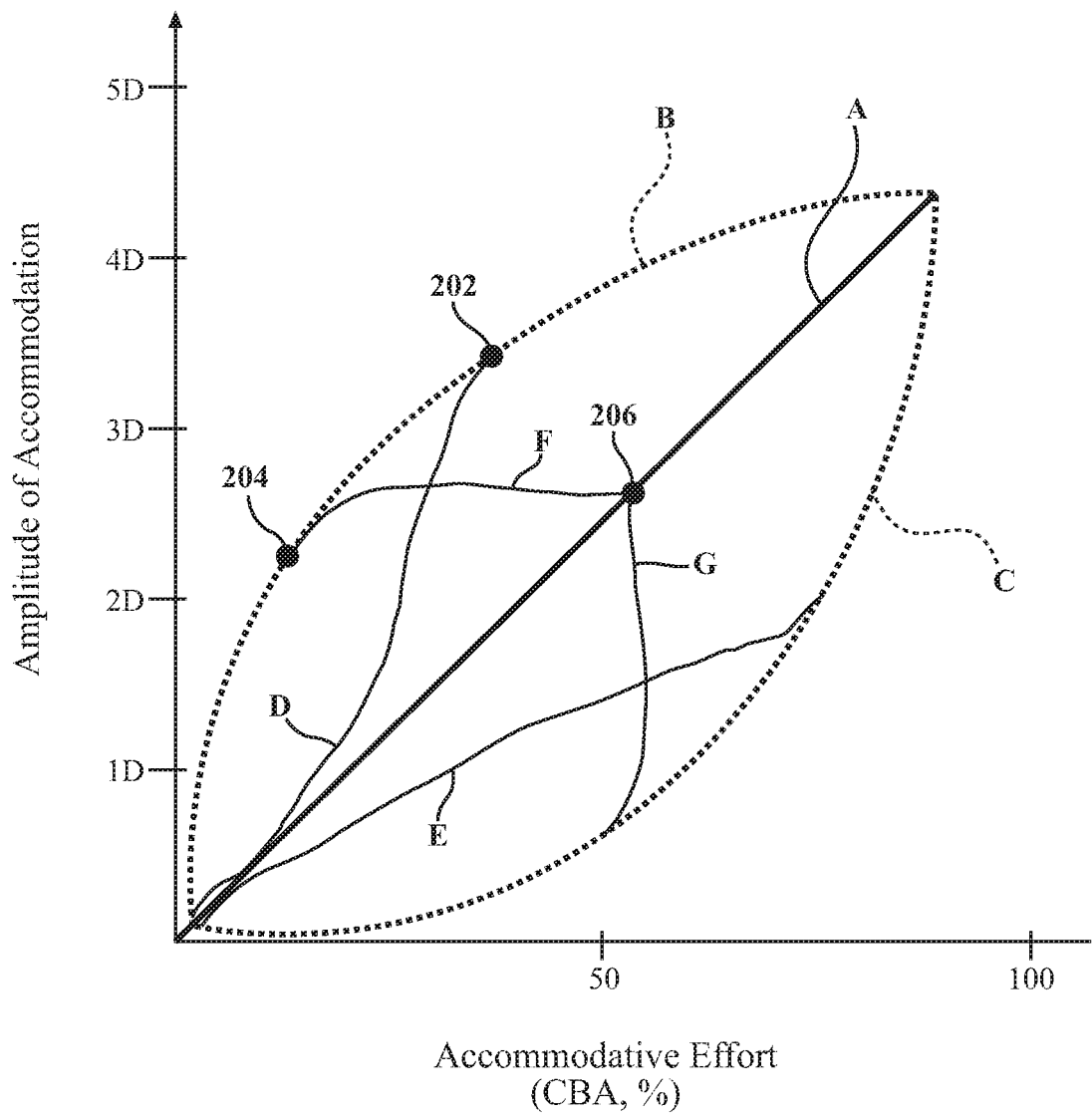
FIG. 23 is a graph correlating an amplitude of accommodation with a percentage of accommodative effort.

An amplitude of 3 to 6 diopters is considered enough to be able to read comfortably if distance vision is perfect. Therefore, a range of 6 D is a useful target for an AIOL. The amplitude of IOLA should have a predictable relationship to accommodative effort (as exerted during CBA by voluntary human effort) as shown in the graph of FIG. 23 as the curve labelled A. The curves labeled B and C are possible curves of AIOLs that can be modified by varying the design of stanchions or by post-operative adjustment (such as with laser energy). The curves labeled D, E, F, and G are also possible curves of AIOLs that can be modified by varying the design of stanchions or by post-operative adjustment. Curve D generally extends between curves A and B from the origin to a point referenced at 202 and then merges with curve B. Curve E is a mirror image of curve D across the curve A. Curve F overlies curve B from the origin to a point referenced at 204 and then merges with curve A at a point referenced at 206. Curve G is a mirror image of curve F across the curve A.

Therefore, an AIOL that merely produces the required degree of accommodation (IOLA) at maximal CBA for near work, has limited utility unless it also provides a smooth transition of accommodative power similar to that achieved by the pre-presbyopic crystalline lens. In fact having a high accommodative power may be a disadvantage if that power is invoked at low levels of CBA or is only available at the extreme accommodative effort because such variations of power may result in disorientating visual fluctuations. The stanchion designs set forth herein (width, flare, curvature, shape, variations in mechanical properties of composite material, etc.) assist in modulating the IOLA to CBA curve. This curve can also be adjusted post-operatively if necessary by application of energy such as laser.

The linking members can also assist with biocompatibility by preventing snagging and also help to minimize deviations from the desired final positions of the stanchions by linking and spacing them apart. The arcuate linking members can interconnect adjacent pairs of base ends. The arcuate linking members do not prevent adjacent base ends from moving relative to each other. The arcuate linking members can be a desirable feature during implantation of the assembly 10, to generally maintain the positions of the base ends. By permitting relative movement of the base ends, the arcuate linking members substantially do not hinder each stanchion from at least some relative movement. The arcuate linking members can be convex relative to the axis 26. When the assembly 10 is implanted, the arcuate linking members can be positioned against the surface of the ciliary muscle. The convex shape allows the arcuate linking members to bias the base ends anteriorly, especially when the ciliary muscle contracts. The linking members can be spaced from both of the base ends 14 and the distal ends 16 along the axis 26. A possible embodiment of such a linking member is shown in phantom in FIG. 1 and referenced at 36'.

The AIOL 10 can also include a positive-power lens 38. The lens 38 can have an anterior side 40 and a posterior side 42 and a center 44 disposed between the anterior side 40 and the posterior side 42. The positive-power lens 38 can be connected with each of the plurality of distal ends whereby the center 44 of the positive power lens 38 is moved along the central optic axis 26 in response to contraction of the first arcuate periphery 18 by contraction of the ciliary muscle.

Figure 8:
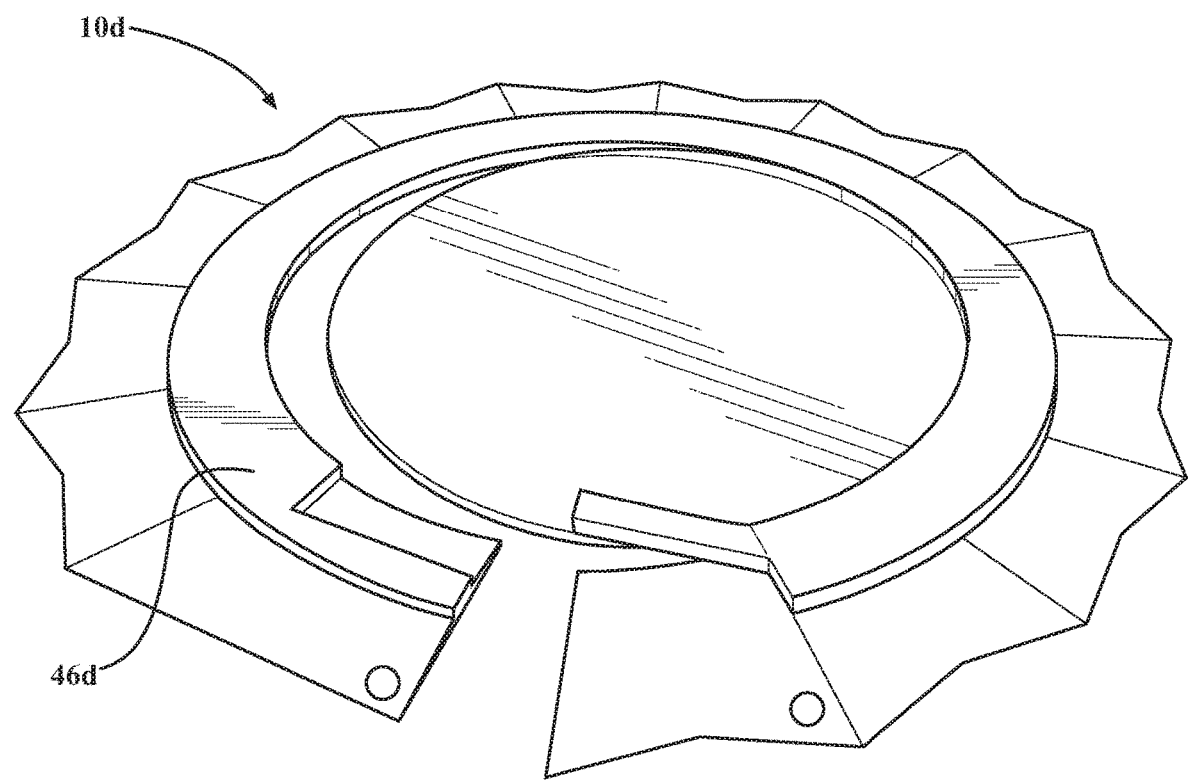
FIG. 8 is a perspective view of an AIOL according to another exemplary embodiment of the present disclosure.

In one or more embodiments of the present disclosure, the lens 38 can be directly connected to the stanchions or can be indirectly connected to the stanchions. In the first exemplary embodiment, the lens 38 can be indirectly connected to the stanchions through a ring member 46. The ring member 46 can be interposed between the positive power lens 38 and each of the plurality of distal ends. The ring member 46 can be a relatively thin, disc structure. The lens 38 can be mounted on the ring member 46 after the ring member 46 and the stanchions have been implanted in the eye, or before. FIG. 8 shows an alternative embodiment of the assembly 10*d* in which a ring member 46*d* is discontinuous to ease insertion in the eye. One end of ring member 46*d* can be moved into an incision in the eye 48 and the remainder of the assembly 10*d* can be drawn into the eye 48. An exemplary lens 38*d* can be mounted in the ring member 46*d* after insertion in the eye. The ring member 46*d* can extend between opposite circumferential ends that interlock. Apertures can be formed in the ring member 46*d* that align when the ends are interlocked. Another structure can be inserted in the aligned apertures to lock the ends together.

Figure 4:
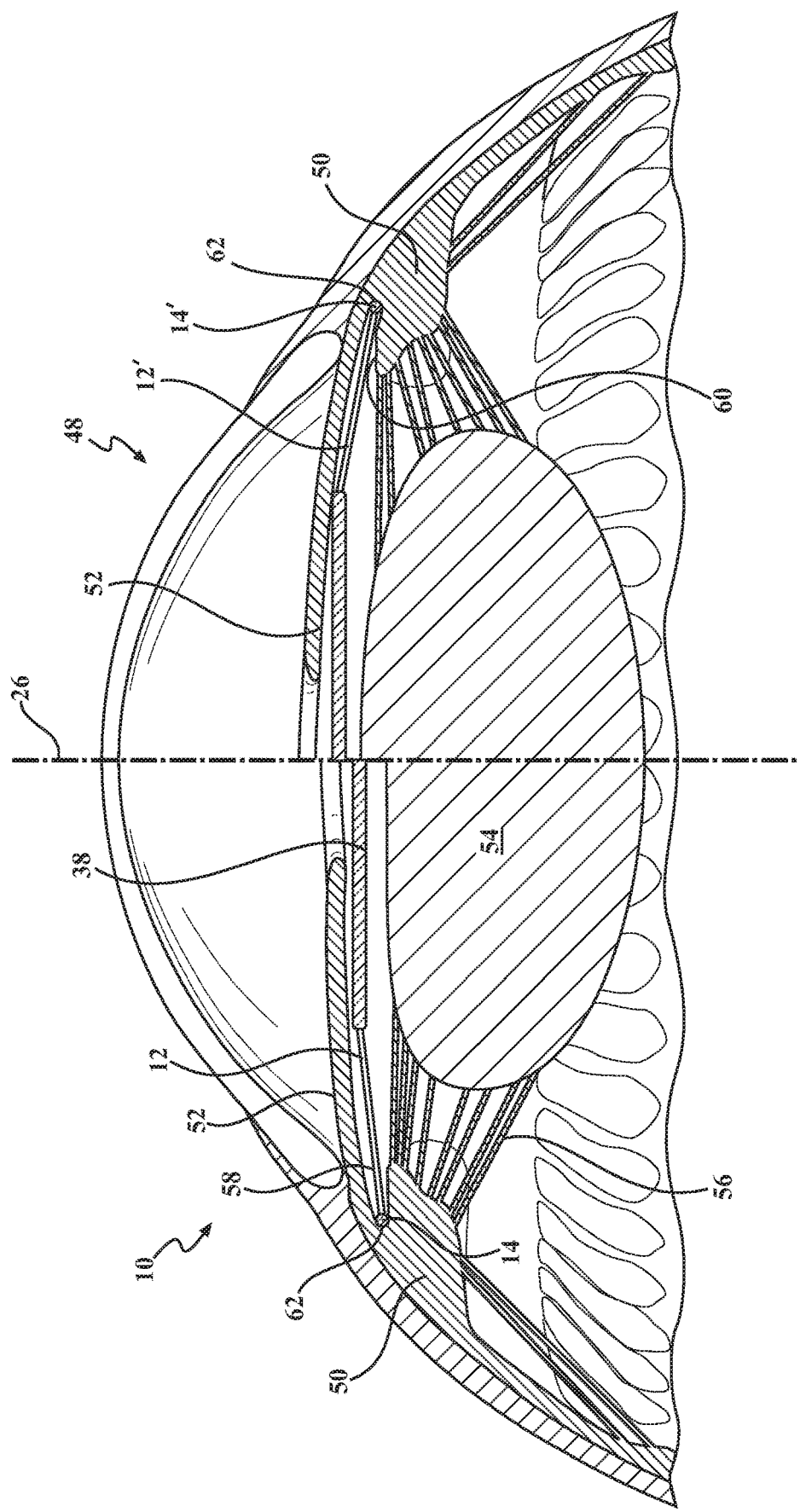
FIG. 4 is a split cross-sectional view showing the AIOL according to the first exemplary embodiment of the present disclosure position in an eye, wherein the left side of the view shows the ciliary muscle in the relaxed condition and the right side of the view shows the ciliary muscle in the contracted condition.

FIG. 4 is a split cross-sectional view showing the AIOL 10 according to the first exemplary embodiment of the present disclosure position in an eye 48. The eye 48 includes a ciliary muscle 50, an iris 52, a capsular bag 54, zonules 56, and a ciliary sulcus 58. The capsular bag 54 is suspended from the ciliary muscle 50 by the zonules 56. The ciliary sulcus 58 is an annular gap or pocket defined between the iris 52 and an anterior side 60 of the ciliary muscle 50. The shape defined by the ciliary sulcus 58 changes when the ciliary muscle 50 contracts. Generally, a "bottom" of the ciliary sulcus 58 (referenced at 62) shifts toward the axis 26 and also shifts anteriorly when the ciliary muscle 50 changes from a relaxed condition to a contracted condition. The base ends of the assembly 10 can ride along the surface of the ciliary sulcus 58 as the ciliary muscle 50 contracts and relaxes.

The left side of the view of FIG. 4 shows the ciliary muscle 50 in the relaxed condition and the right side of the view shows the ciliary muscle 50 in the contracted condition. In an exemplary operation of the first exemplary embodiment, when the ciliary muscle 50 is relaxed, the lens 38 is disposed at a first position within the eye 48 and the stanchion 12 is disposed at a first angle relative to the lens 38. When the ciliary muscle 50 contracts, the lens 38 is moved to a second position in the eye 48, the second position being anterior to the first position. The lens is referenced at 38' when in the second position. Also, the stanchion 12 is shifted to a second angle relative to the lens 38, the second angle being greater than the first angle. The stanchion is referenced at 12' when disposed at the second angle. The base end 14 is shifted toward the axis 26 and anteriorly when the ciliary muscle 50 contracts. The base end is referenced at 14' when the ciliary muscle 50 is contracted.

Figure 5A:
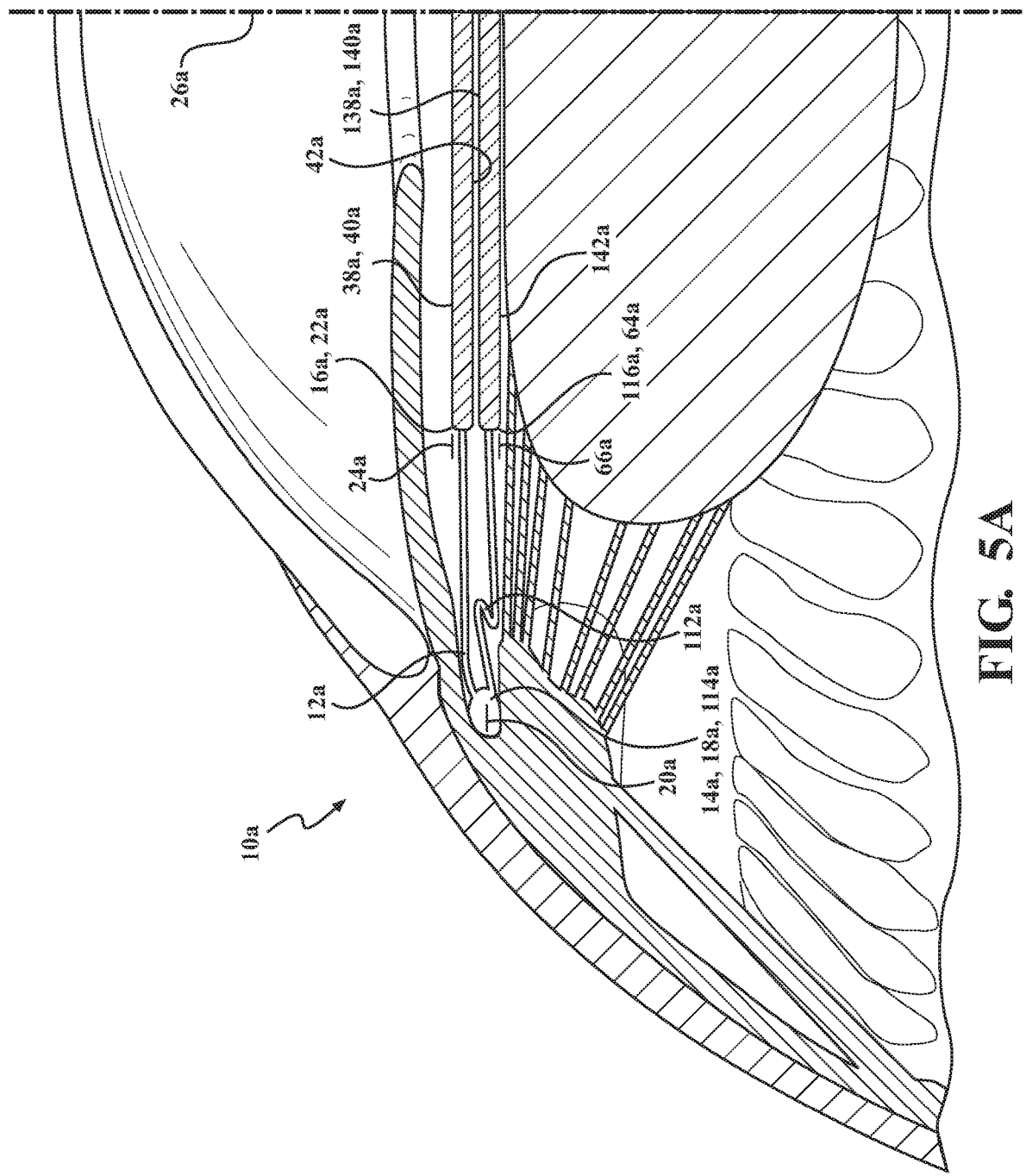
Figure 5B:
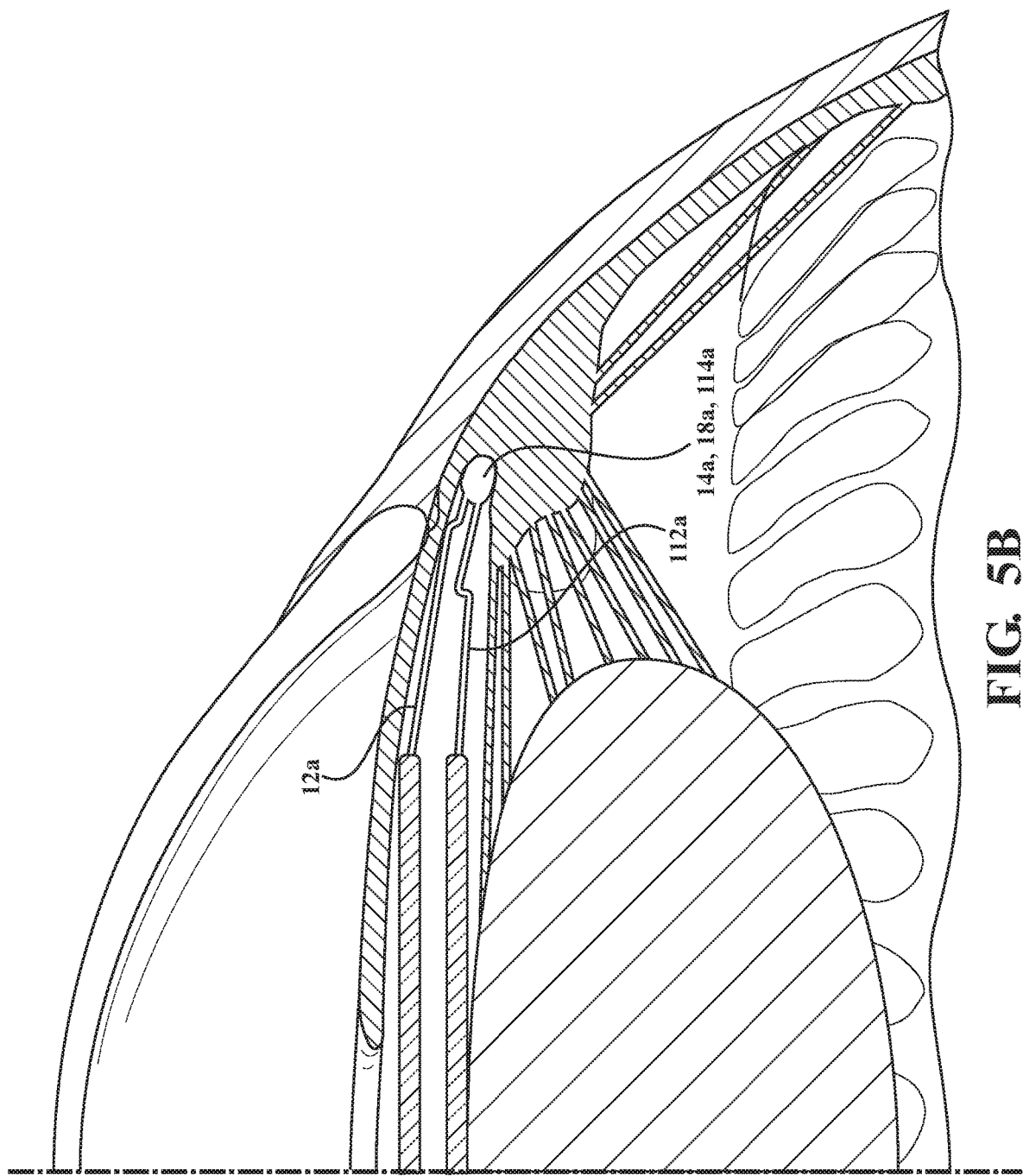

In one or more embodiments of the present disclosure, a plurality of lens can be supported. In a first alternative embodiment, as shown in FIGS. 5A and 5B, an AIOL 10*a* can include a plurality of stanchions each extending between a base end and a distal end, such as stanchion 12*a* with base end 14a and distal end 16a. The base ends can be disposed in spaced relation to one another about a first arcuate periphery 18a extending in a first plane 20a. The distal ends can be disposed about a second arcuate periphery 22a extending in a second plane 24a. The first plane 20a can be spaced from the second plane 24a in a posterior direction along a central optic axis 26a. The first arcuate periphery 18a can have a greater radius than the second arcuate periphery 22a.

The AIOL 10a can also have a positive-power lens 38a. The positive-power lens 38a can have an anterior 40a side and a posterior side 42a and a center disposed between the anterior side 40a and the posterior side 42a. The positive-power lens 38a connected with each of the plurality of distal ends whereby the center of the positive power lens 38a is moved along the central optic axis 26a in response to contraction of the first arcuate periphery 18a.

The AIOL 10a can also include a second plurality of stanchions each respectively extending between a second base end and a second distal end, such as stanchion 112a having base end 114a and distal end 116a. Each of the base ends of the second plurality of stanchions can be interconnected with one of the base ends of the first plurality of stanchions at intersections and thus be spaced from one another about the first arcuate periphery 18a. The second distal ends can be disposed about an arcuate periphery 64a extending in a plane 66a. The plane 20a can be spaced from the plane 66a along the central optic axis 26a and parallel to the plane 66a. The first arcuate periphery 18a can have a greater radius than the arcuate periphery 64a.

The AIOL 10a can also include a secondary lens 138a having a second anterior side 140a and a second posterior side 142a and a second center disposed between the second anterior side 140a and the second posterior side 142a. The secondary lens 138a may or may not be a positive power lens. The second anterior side 140a can confront the posterior side 42a. The secondary lens 138a can be connected with each of the plurality of second distal ends whereby the second center of the secondary lens 138a is moved along the central optic axis 26a in response to contraction of the third arcuate periphery.

In the first alternative embodiment, both of the stanchions 12a and 112a extend along respective arcuate profiles in a plane containing the central optic axis 26. The views of FIGS. 5A and 5B are in such a plane. The arcuate profile for each stanchion 12a, 112a is defined by at least one radius and at least one center of curvature. The arcuate profile of the stanchion 112a is defined by more than one radius and more than one center of curvature. The arcuate profiles of both stanchions 12a, 112a extend away from the interconnected base ends 14a, 114a in the same direction along the central optic axis 26a.

FIG. 5A shows the ciliary muscle 50a in the relaxed condition and FIG. 5B shows the ciliary muscle 50a in the contracted condition. In an exemplary operation of the first alternative embodiment, when the ciliary muscle 50a is relaxed, the lens 38a is disposed at a first position within the eye 48a and the stanchion 12a is disposed in a first configuration relative to the lens 38a. When the ciliary muscle 50a contracts, the lens 38a is moved to a second position in the eye 48a, the second position being anterior to the first position. The lens is referenced at 38a' when in the second position. Also, the stanchion 12a is elastically deformed into a second configuration relative to the lens 38a. The stanchion is referenced at 12a' when disposed in the second configuration. Further, when the ciliary muscle 50a is relaxed, the lens 138a is disposed at a first position within the eye 48a and the stanchion 112a is disposed in a first configuration relative to the lens 138a. When the ciliary muscle 50a contracts, the lens 138a is moved to a second position in the eye 48a, the second position being posterior to the first position. The secondary lens is referenced at 138a' when in the second position. Also, the stanchion 112a is elastically deformed into a second configuration relative to the lens 138a. The stanchion is referenced at 112a' when disposed in the second configuration. A distance between the lenses 38a and 138a increases when the ciliary muscle 50a contracts.

FIG. 5A shows that the stanchion 12a includes a first portion extending substantially straight from the positive-power lens 38a toward the base end 14a in a third plane containing the central optic axis 26a and also includes a second portion extending along an arcuate profile in the third plane. The arcuate profile is defined by at least one radius and at least one center of curvature. FIG. 5A also shows the stanchion 112a extends along a plurality of arcuate profiles in the plane containing the central optic axis 26a. The arcuate profiles are defined by more than one radius and more than one center of curvature in the plane and are separated by a straight section of the stanchion 112a. FIG. 5A also shows an acute angle is defined between the stanchion 12a and the stanchion 112a extending away from one of the intersection of the base end and the second base end. FIG. 5A also shows that the stanchion 12a and the stanchion 112a extend away from the base end 14a and second base end 114a in the same direction along the central optic axis 26a. FIG. 5A also shows the center of curvature of the curved portion of stanchion 12a is posterior of the base end 14a along the central optic axis 26a. FIG. 5A also shows the at least one center of curvature is between the base end 14a and the distal end 16a relative to a direction perpendicular to the central optic axis 26a. FIG. 5A also shows the at least one center of curvature is closer to the base end 14a than the distal end 16a along the direction. FIG. 5A also shows that the AIOL 10a is configured such that the at least one center of curvature is within zonules 56 of the eye 48 when the AIOL 10a is positioned in the eye 48 and the ciliary muscle 50 is relaxed. FIG. 5A also shows that the AIOL 10a is further configured such that the at least one center of curvature is outside of a capsular bag 54 of the eye 48 when the AIOL 10a is positioned in the eye 48 and the ciliary muscle 50 is relaxed. FIG. 5A also shows that the second base end 114a is interconnected to the base end 14a at respective intersections positioned along the first arcuate periphery 18a such that the first arcuate periphery 18a and the third arcuate periphery are coplanar and wherein a thickness of the intersection of the base end 14a and the second base end 114a is greater than a combination of a thickness of the stanchion 12a extending from the intersection and a thickness of the stanchion 112a extending from the intersection. FIG. 5A also shows the stanchion 112a extends along a plurality of arcuate profiles in the plane containing the central optic axis 26a, the arcuate profiles defined by more than one radius or more than one center of curvature in the plane, and wherein a first of the centers of curvature is positioned on an anterior side of the stanchion 112a and a second of the centers of curvature is positioned on a posterior side of the stanchion 112a.

Figure 6B:
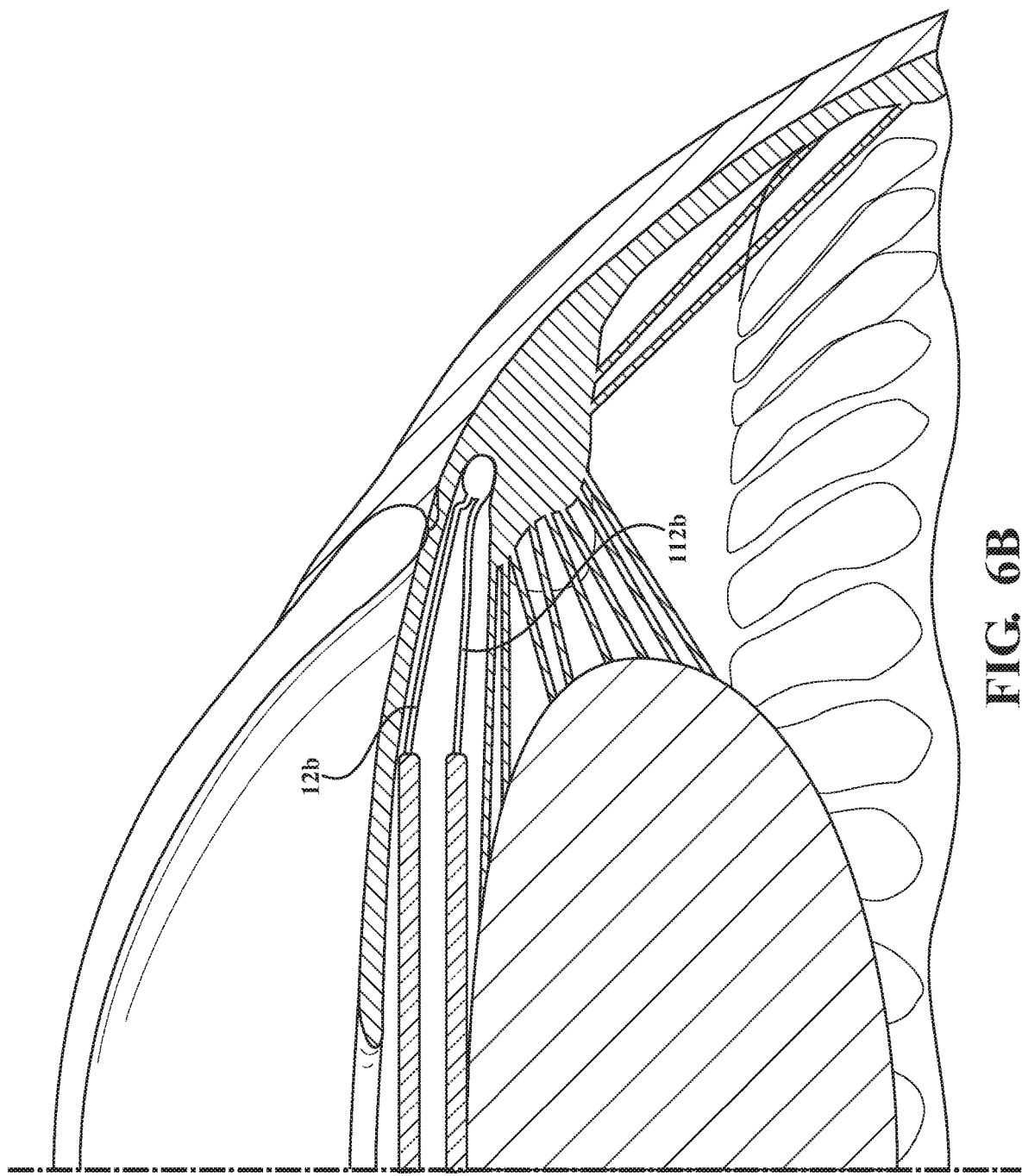

In a second alternative embodiment, as shown in FIGS. 6A and 6B, an AIOL 10b can include a plurality of stanchions each extending between a base end and a distal end, such as stanchion 12b with base end 14b and distal end 16b. The base ends can be disposed in spaced relation to one another about a first arcuate periphery 18b extending in a first plane 20b. The distal ends can be disposed about a second arcuate periphery 22b extending in a second plane 24b. The first plane 20b can be spaced from the second plane 24b in a posterior direction along a central optic axis 26b. The first arcuate periphery 18b can have a greater radius than the second arcuate periphery 22b.

The AIOL 10b can also have a positive-power lens 38b. The positive-power lens 38b can have an anterior 40b side and a posterior side 42b and a center disposed between the anterior side 40b and the posterior side 42b. The positive-power lens 38b connected with each of the plurality of distal ends whereby the center of the positive power lens 38b is moved along the central optic axis 26b in response to contraction of the first arcuate periphery 18b.

The AIOL 10b can also include a second plurality of stanchions each respectively extending between a second base end and a second distal end, such as stanchion 112b having base end 114b and distal end 116b. Each of the base ends of the second plurality of stanchions can be interconnected with one of the base ends of the first plurality of stanchions at intersections and thus be spaced from one another about the first arcuate periphery 18b. The second distal ends can be disposed about an arcuate periphery 64b extending in a plane 66b. The plane 20b can be spaced from the plane 66b along the central optic axis 26b and parallel to the plane 66b. The first arcuate periphery 18b can have a greater radius than the arcuate periphery 64b.

The AIOL 10b can also include a secondary lens 138b having a second anterior side 140b and a second posterior side 142b and a second center disposed between the second anterior side 140b and the second posterior side 142b. The secondary lens 138b may or may not be a positive power lens. The second anterior side 140b can confront the posterior side 42b. The secondary lens 138b can be connected with each of the plurality of second ends whereby the second center of the secondary lens 138b is moved along the central optic axis 26b in response to contraction of the third arcuate periphery.

In the second alternative embodiment, both of the stanchions 12b and 112b extend along respective arcuate profiles in a plane containing the central optic axis 26. The views of FIGS. 6A and 6B are taken is such a plane. The exemplary arcuate profiles for each stanchion 12b, 112b are defined by one radius and one center of curvature. The arcuate profiles of both stanchions 12b, 112b extend away from the interconnected base ends 14b, 114b in the same direction along the central optic axis 26b.

FIG. 6A shows the ciliary muscle 50b in the relaxed condition and FIG. 6B shows the ciliary muscle 50b in the contracted condition. In an exemplary operation of the first alternative embodiment, when the ciliary muscle 50b is relaxed, the lens 38b is disposed at a first position within the eye 48b and the stanchion 12b is disposed in a first configuration relative to the lens 38b. When the ciliary muscle 50b contracts, the lens 38b is moved to a second position in the eye 48b, the second position being anterior to the first position. The lens is referenced at 38b' when in the second position. Also, the stanchion 12b is elastically deformed into a second configuration relative to the lens 38b. The stanchion is referenced at 12b' when disposed in the second configuration. Further, when the ciliary muscle 50b is relaxed, the lens 138b is disposed at a first position within the eye 48b and the stanchion 112b is disposed in a first configuration relative to the lens 138b. When the ciliary muscle 50b contracts, the lens 138b is moved to a second position in the eye 48b, the second position being anterior to the first position. The secondary lens is referenced at 138b' when in the second position. Also, the stanchion 112b is elastically deformed into a second configuration relative to the lens 138b. The stanchion is referenced at 112b' when disposed in the second configuration. A distance between the lenses 38b and 138b increases when the ciliary muscle 50b contracts.

Figure 7A:
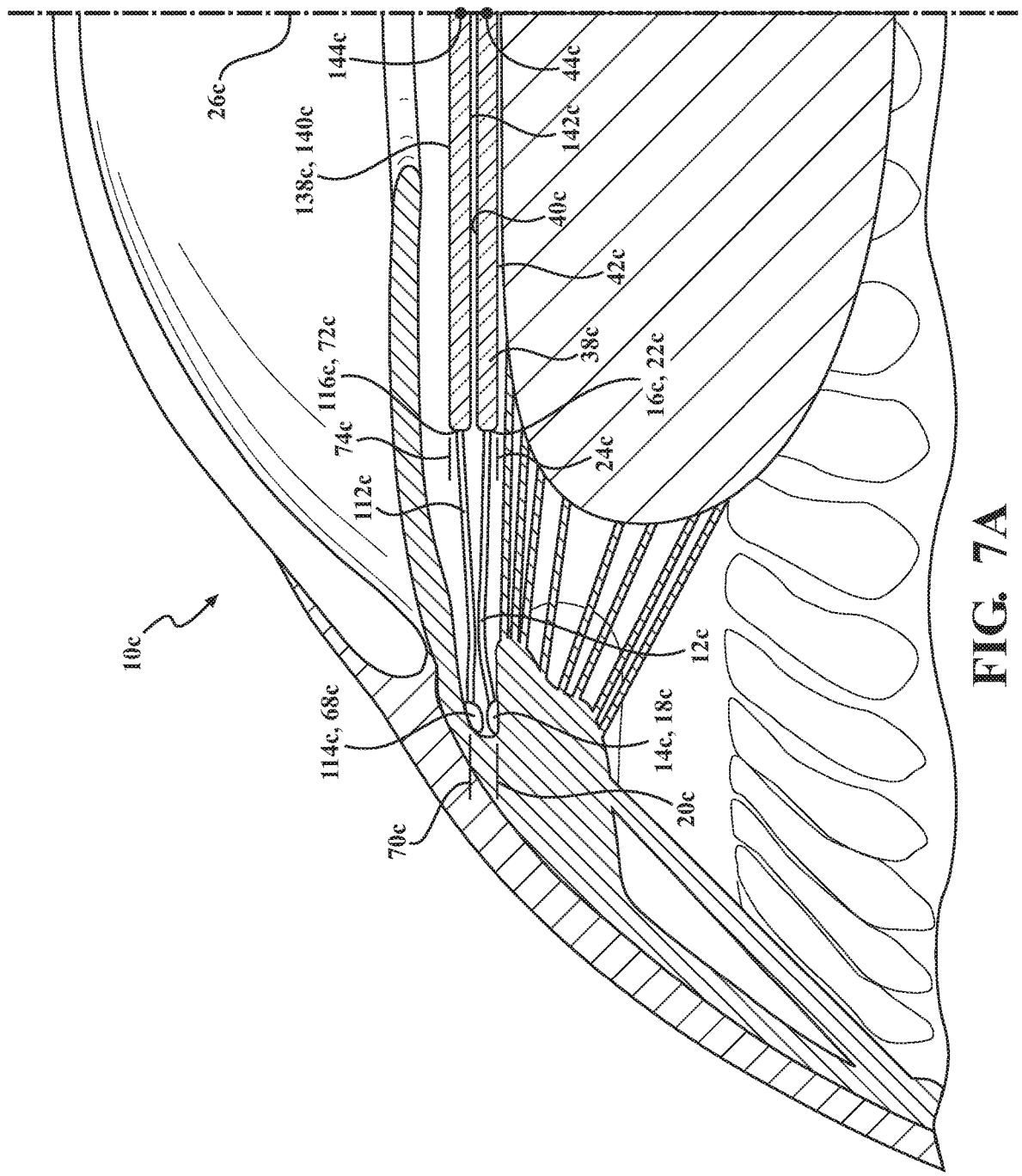
Figure 7B:
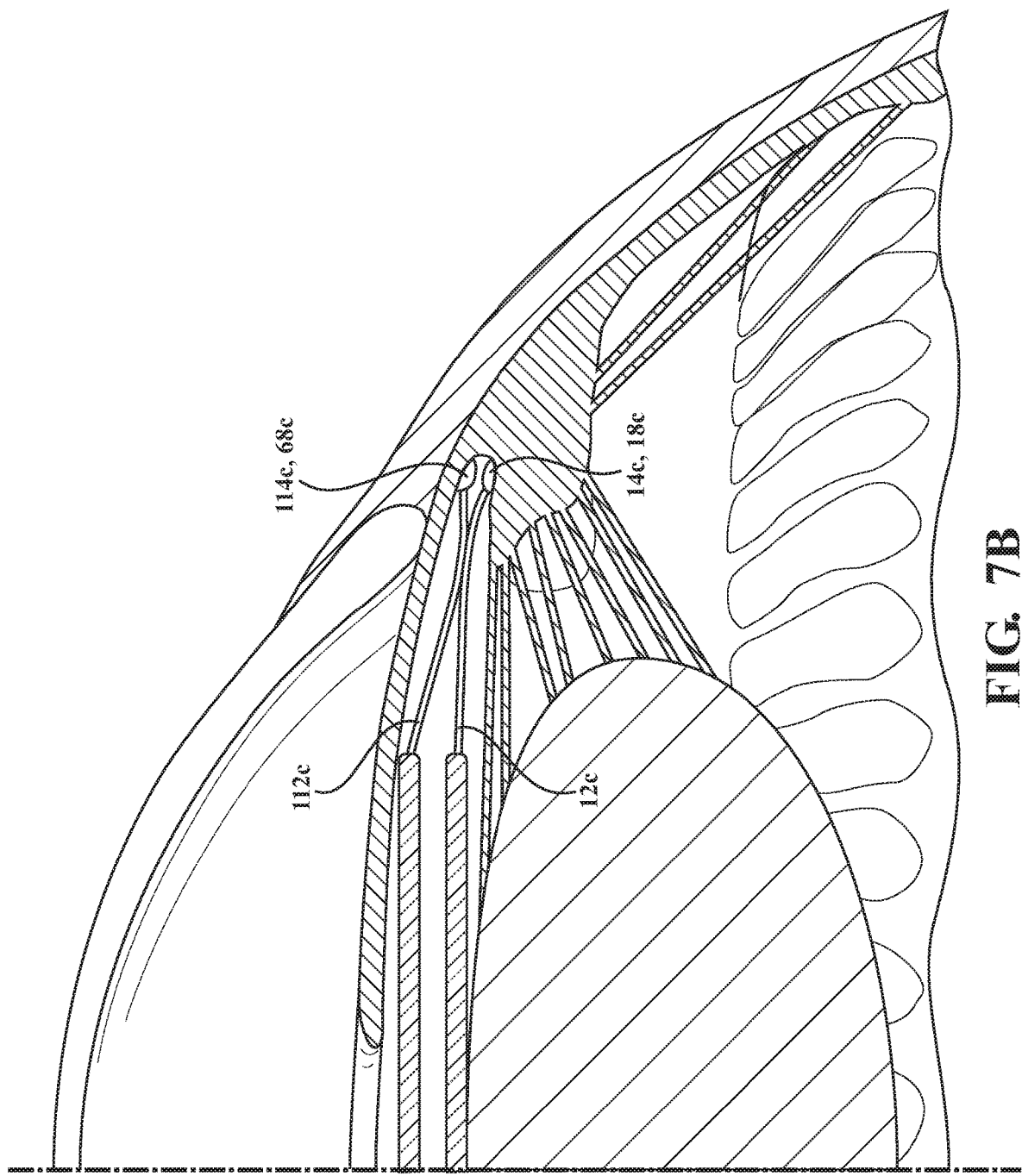

In a third alternative embodiment, as shown in FIGS. 7A and 7B, an AIOL 10c can include a plurality of stanchions each extending between a base end and a distal end, such as stanchion 12c with base end 14c and distal end 16c. The base ends can be disposed in spaced relation to one another about a first arcuate periphery 18c extending in a first plane 20c. The distal ends can be disposed about a second arcuate periphery 22c extending in a second plane 24c. The first plane 20c can be spaced from the second plane 24c in an anterior direction along a central optic axis 26c. The first arcuate periphery 18c can have a greater radius than the second arcuate periphery 22c.

The AIOL 10c can also have a positive-power lens 38c. The positive-power lens 38c can have an anterior 40c side and a posterior side 42c and a center 44c disposed between the anterior side 40c and the posterior side 42c. The positive-power lens 38c connected with each of the plurality of distal ends whereby the center 44c of the positive power lens 38c is moved along the central optic axis 26c in response to contraction of the first arcuate periphery 18c.

The AIOL 10c can also include a second plurality of stanchions each respectively extending between a second base end and a second distal end, such as stanchion 112c having base end 114c and distal end 116c. The base ends 114c can be spaced from one another about an arcuate periphery 68c extending in a plane 70c. The second distal ends can be disposed about an arcuate periphery 72c extending in a plane 74c. The planes 70c and 74c can be spaced from one another and from the planes 20c and 24c along the central optic axis 26c. The arcuate periphery 68c can have a greater radius than the arcuate periphery 72c.

The AIOL 10c can also include a secondary lens 138c having a second anterior side 140c and a second posterior side 142c and a second center 144c disposed between the second anterior side 140c and the second posterior side 142c. The secondary lens 138c may or may not be a positive power lens. The second posterior side 142c can confront the anterior side 40c. The secondary lens 138c can be connected with each of the plurality of second ends whereby the second center 144c of the secondary lens 138c is moved along the central optic axis 26c in response to contraction of the third arcuate periphery.

In the second alternative embodiment, both of the stanchions 12c and 112c extend along respective arcuate profiles in a plane containing the central optic axis 26c. The views of FIGS. 7A and 7B are taken in such a plane. The exemplary arcuate profiles for each stanchion 12c, 112c are defined by a plurality of radii and centers of curvature. The arcuate profiles of both stanchions 12c, 112c extend away from the respective base ends 14c, 114c toward one another along the central optic axis 26c.

FIG. 7A shows the ciliary muscle 50c in the relaxed condition and FIG. 7B shows the ciliary muscle 50c in the contracted condition. In an exemplary operation of the first alternative embodiment, when the ciliary muscle 50c is relaxed, the lens 38c is disposed at a first position within the eye 48c and the stanchion 12c is disposed in a first configuration relative to the lens 38c. When the ciliary muscle 50c contracts, the lens 38c is moved to a second position in the eye 48c, the second position being posterior to the first position. The lens is referenced at 38c' when in the second position. Also, the stanchion 12c is elastically deformed into a second configuration relative to the lens 38c. The stanchion is referenced at 12c' when disposed in the second configuration. Further, when the ciliary muscle 50c is relaxed, the lens 138c is disposed at a first position within the eye 48c and the stanchion 112c is disposed in a first configuration relative to the lens 138c. When the ciliary muscle 50c contracts, the lens 138c is moved to a second position in the eye 48c, the second position being anterior to the first position. The secondary lens is referenced at 138c' when in the second position. Also, the stanchion 112c is elastically deformed into a second configuration relative to the lens 138c. The stanchion is referenced at 112c' when disposed in the second configuration. A distance between the lenses 38c and 138c increases when the ciliary muscle 50c contracts.

Although the cross sections of FIGS. 7A and 7B show non-connected stanchions that may respond better to pinching in the ciliary sulcus, it can be desirable that some of the intervening stanchion pairs should be connected to each other to increase the likelihood that the anterior and posterior ring members/lens remain in apposition relative to each other. Otherwise, the anterior and posterior ring members/lens may not stay together during implantation.

Figure 9A:
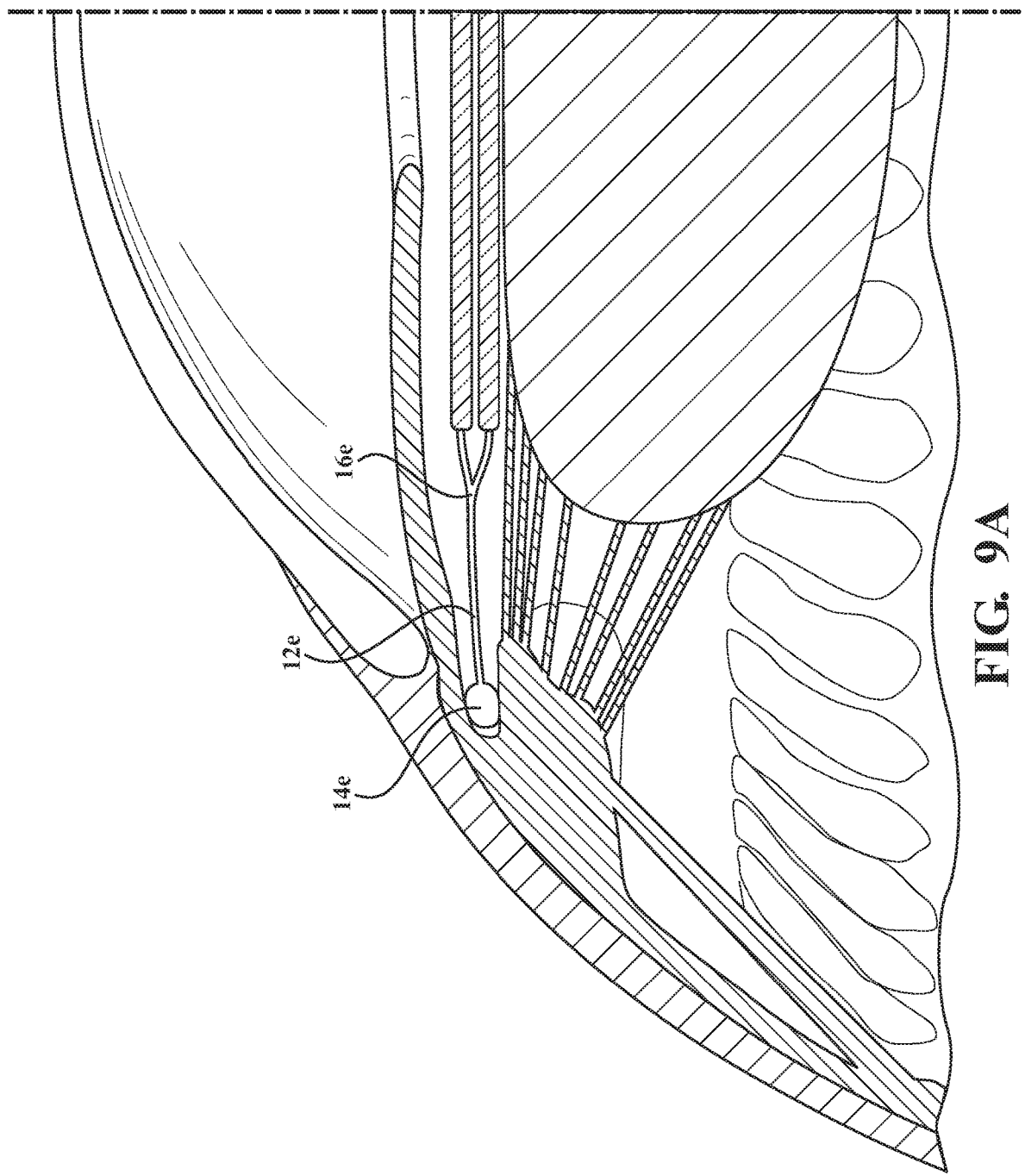

In one or more embodiments of the present disclosure, at least one of the plurality of stanchions can contain fluid. The stanchion can be filled with fluid prior to implantation in the eye or after being implanted. For example, as shown in FIGS. 9A and 9B, a stanchion 12e can extend between a base end 14e and a distal end 16e. The stanchion 12e can be elastically deformable so that the bulbous base end 14e is compressed during contraction of the ciliary sulcus and thereby expand a bellows-like distal end 16e. The distal end 16e can elastically expand when the ciliary muscle contracts. First and second lenses 38e and 138e can be engaged with the distal end 16e and spaced locations on the distal end 16e. When the stanchion 12e is compressed, fluid is directable out of the base end 14e to expand the distal end 16e. Elastic deformation of the distal end 16e can cause the lenses 38e, 138e to change position relative to one another. FIG. 9A shows the arrangement when the ciliary sulcus is relaxed and FIG. 9B shows the arrangement when the ciliary sulcus is contracted. The lenses 38e, 138e are further apart from one another in FIG. 9B.

Figure 10:
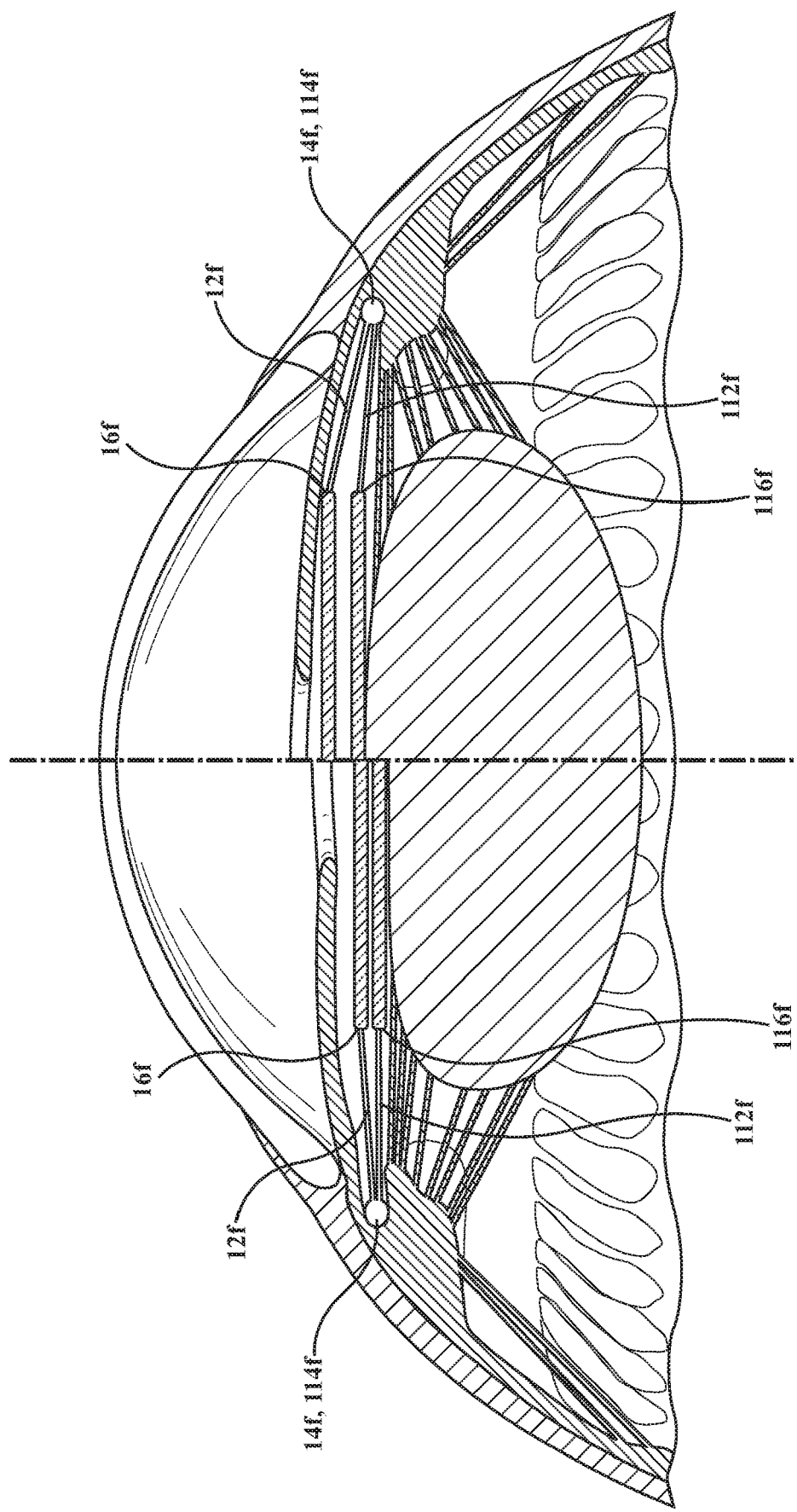
FIG. 10 is a split cross-sectional view showing the AIOL according to another exemplary embodiment of the present disclosure position in an eye, wherein the left side of the view shows the ciliary muscle in the relaxed condition and the right side of the view shows the ciliary muscle in the contracted condition.

FIG. 10 shows a third alternative embodiment wherein a first plurality of stanchions 12f extends along a first substantially straight profile in a plane containing the central optic axis 26f and a second plurality of stanchions 112f extends along a second substantially straight profile in the plane containing the central optic axis 26f. The first substantially straight profile and the second substantially straight profile extend away from the respective base end 14f and second base end 114f in the opposite directions along the central optic axis 26f. The stanchions 12f extend anteriorly and the stanchions 112f extend posteriorly.

Figure 11:
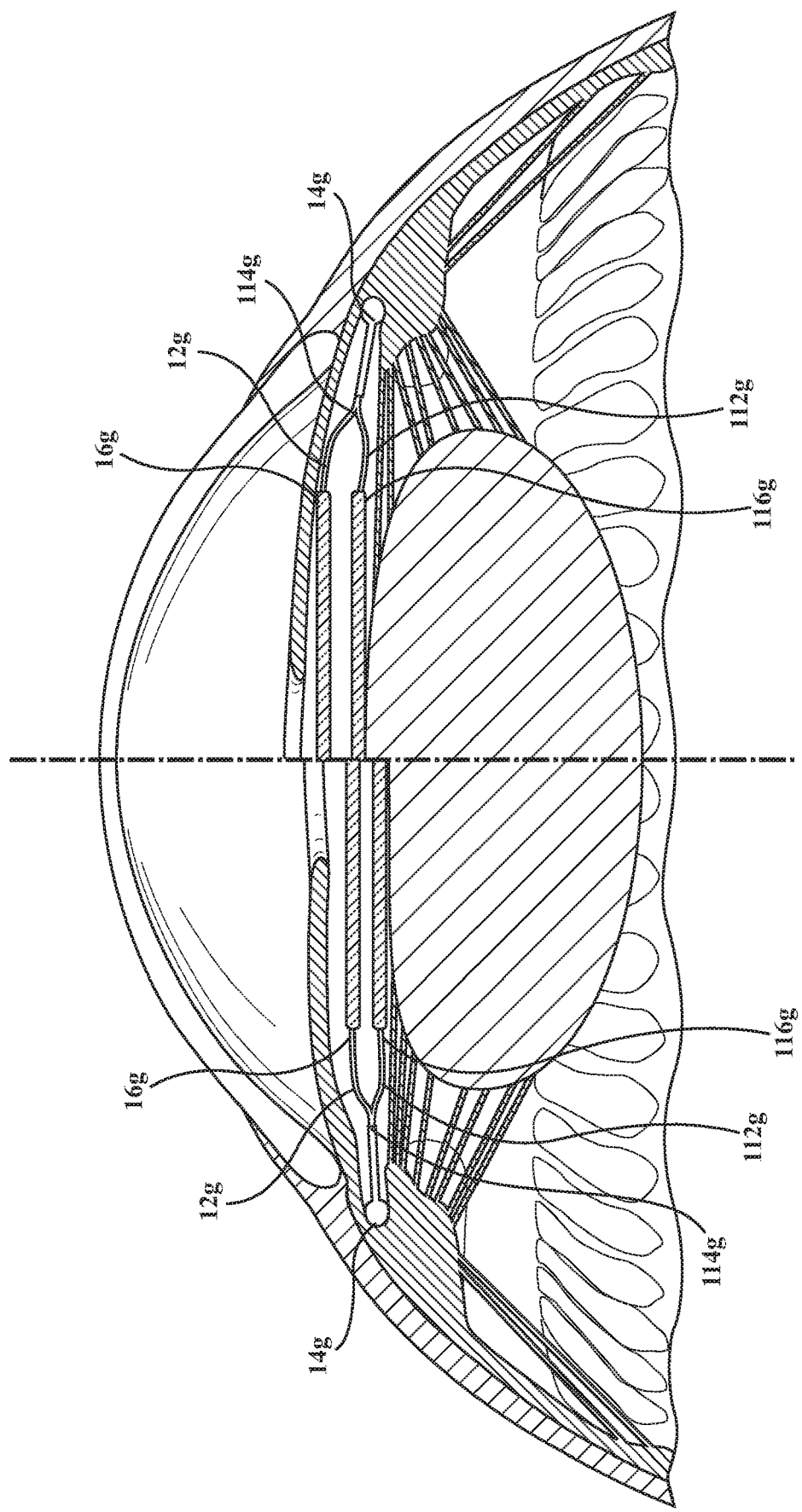
FIG. 11 is a split cross-sectional view showing the AIOL according to another exemplary embodiment of the present disclosure position in an eye, wherein the left side of the view shows the ciliary muscle in the relaxed condition and the right side of the view shows the ciliary muscle in the contracted condition.

FIG. 11 shows a fourth alternative embodiment wherein each of a first plurality of stanchions 12g extends between a base end 14g and a distal end 16g. Each of a second plurality of stanchions 112g extends between a base end 114g and a distal end 116g. Each of the second base ends 114g is mounted on one of said plurality of stanchions 12g.

Figure 12:
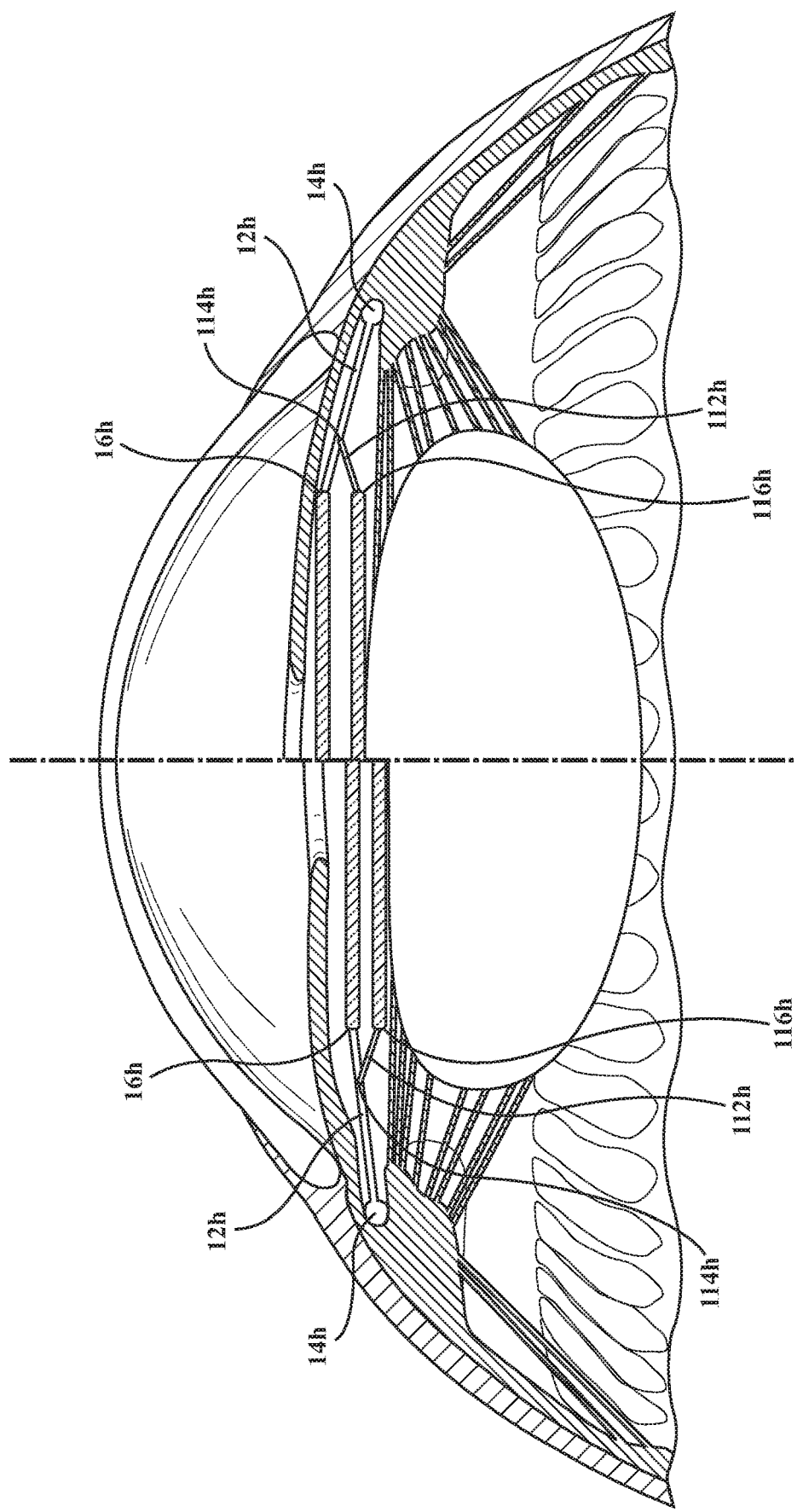
FIG. 12 is a split cross-sectional view showing the AIOL according to another exemplary embodiment of the present disclosure position in an eye, wherein the left side of the view shows the ciliary muscle in the relaxed condition and the right side of the view shows the ciliary muscle in the contracted condition.

FIG. 12 shows another alternative embodiment wherein each of a first plurality of stanchions 12h extends between a base end 14h and a distal end 16h. Each of a second plurality of stanchions 112h extends between a base end 114h and a distal end 116h. Each of the second base ends 114h is mounted on one of said plurality of stanchions 12h. It is noted that in FIG. 12 the capsular bag is illustrated as empty and devoid of a crystalline lens to confirm that an AIOL according to one or more embodiments of the present disclosure is an alternative to the natural lens and that the function of an AIOL according to one or more embodiments of the present disclosure can occur independent of any capsular bag changes.

Figure 13:
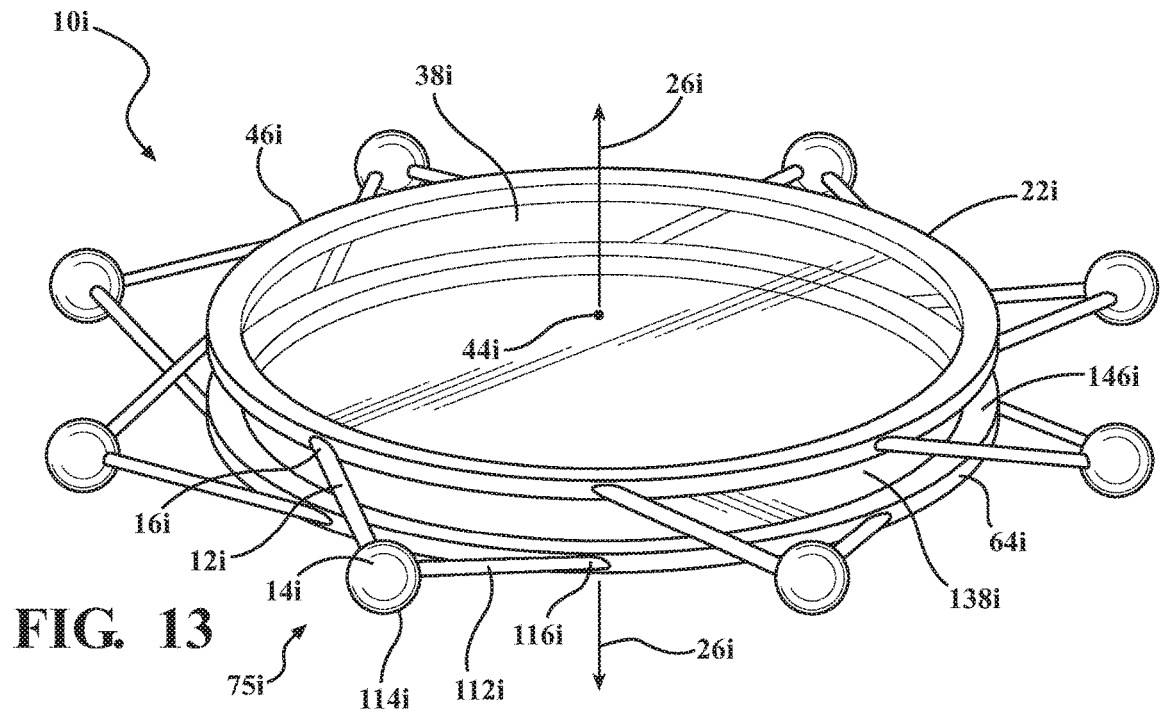
FIG. 13 is a perspective view of an AIOL according to another exemplary embodiment of the present disclosure.
Figure 15:
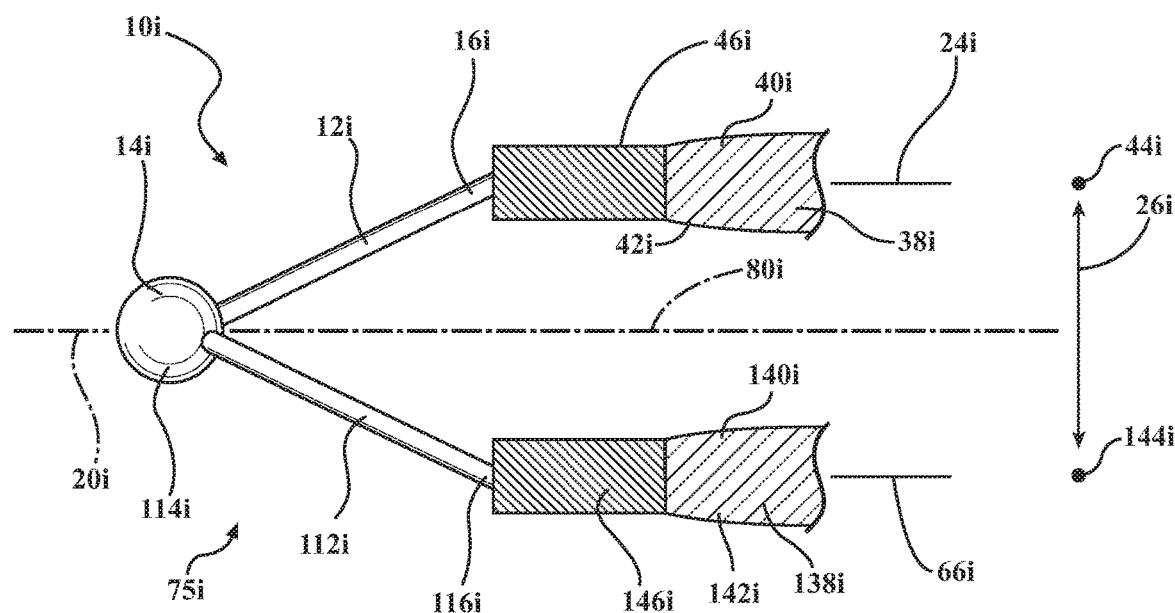
FIG. 15 is a side view of the exemplary embodiment shown in FIG. 13.
Figure 14:
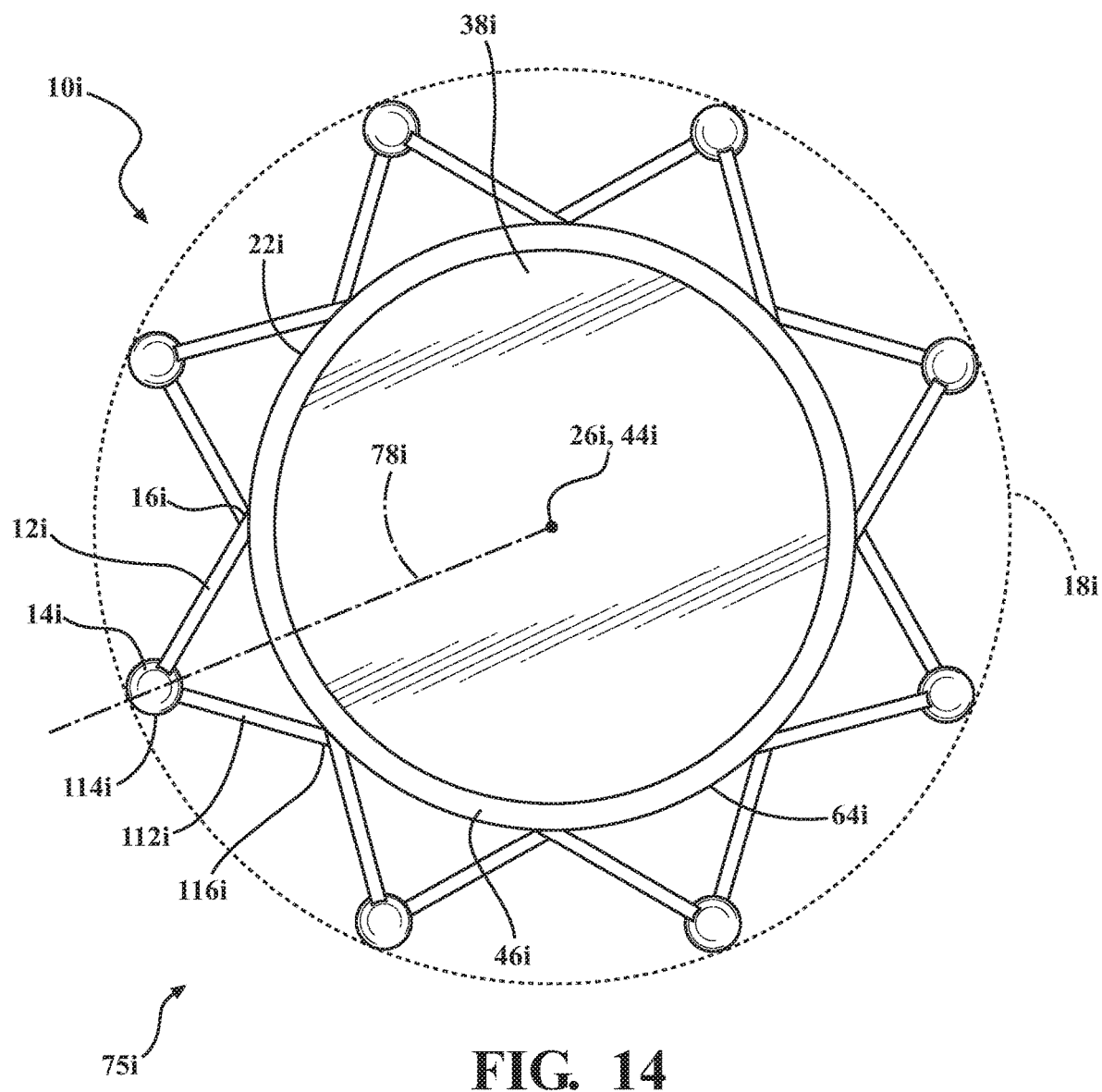
FIG. 14 is a top view of the exemplary embodiment shown in FIG. 13.

In another alternative embodiment, as shown in FIGS. 13-15, an AIOL 10i can include a plurality of stanchions each extending a first distance between a base end and a distal end, such as stanchion 12i with base end 14i and distal end 16i. Each of the first plurality of stanchions 12i can be straight over at least most of the first distance. Each of the exemplary first plurality of stanchions 12i is straight over the first distance, as shown by FIGS. 13-15. The base ends 14i can be disposed in spaced relation to one another about a first arcuate periphery 18i extending in a first plane 20i. The distal ends 16i can be disposed about a second arcuate periphery 22i extending in a second plane 24i. The first plane 20i can be spaced from the second plane 24i in a posterior direction along a central optic axis 26i. The first arcuate periphery 18i can have a greater radius than the second arcuate periphery 22i.

The AIOL 10i can also include a ring member 46i. The ring member 46i can be interconnected with each of the plurality of distal ends 16i. The ring member 46i can be a relatively thin, disc structure. A haptic passenger such as lens 38i can be mounted on the ring member 46i after the ring member 46i and the stanchions 12i have been implanted in the eye, or before. The exemplary first lens 38i has a first anterior side 40i and a first posterior side 42i and a first center 44i disposed between the first anterior side 40i and the first posterior side 42i. The central optic axis 26i extends through the first center 44i. The exemplary first lens 38i is connected with each of the plurality of first distal ends 16i through the ring 46i. In other embodiments, the first lens 38i can be directly connected with the plurality of first distal ends 16i.

The AIOL 10i can also include a second plurality of stanchions each respectively extending a second distance between a second base end and a second distal end, such as stanchion 112i having base end 114i and distal end 116i. Each of the second plurality of stanchions 112i can be straight over at least most of the second distance. Each of the exemplary second plurality of stanchions 112i is straight over the second distance, as shown by FIGS. 13-15. Each of the second base ends 114i of the second plurality of stanchions 112i can be interconnected with one of the first base ends 14i of the first plurality of stanchions 12i at intersections and thus be spaced from one another about the first arcuate periphery 18i, in the first plane 20i, as the first base ends 14i are spaced from one another. The plane of the second base ends 114i is the same plane as the first base ends 14i, the plane 20i. The second distal ends 116i can be disposed about a third arcuate periphery 64i extending in a third plane 66i. The plane 20i can be spaced from the plane 66i along the central optic axis 26i and be parallel to the plane 66i. The arcuate periphery 18i can have a greater radius than the arcuate periphery 64i.

The AIOL 10i can also include a ring member 146i. The ring member 146i can be interconnected with each of the plurality of distal ends 116i. The ring member 146i can be a relatively thin, disc structure. A haptic passenger such as lens 138i can be mounted on the ring member 146i after the ring member 146i and the stanchions 112i have been implanted in the eye, or before. The exemplary second lens 138i has a second anterior side 140i and a second posterior side 142*i* and a second center 144*i* disposed between the second anterior side 140*i* and the second posterior side 142*i*. The central optic axis 26*i* extends through the second center 144*i*. The exemplary second anterior side 140*i* confronts the first posterior side 42*i* of the first lens 38*i*. The exemplary second lens 138*i* is connected with each of the plurality of second distal ends 116*i* through the ring 146*i*. In other embodiments, the second lens 138*i* can be directly connected with the plurality of second distal ends 116*i*.

The stanchions 12*i* each extend along a first path transverse to and spaced from the central optic axis 26*i* in a first plane transverse the central optic axis 26*i*. FIG. 14 is a view of such a plane. Each of the second plurality of stanchions 112*i* extends along a second path that is transverse to and spaced from the central optic axis 26*i* in the first plane. The first path and the second path are mirrored with respect one another in the first plane about a first axis 78*i* extending between the base end 14*i*, 114*i* and the central optic axis 26*i* in the first plane. This is shown in FIG. 14. The first path and the second path are mirrored with respect one another in a second plane containing the central optic axis 26*i* about a second axis 80*i* extending between the base end 14*i*, 114*i* and the central optic axis 26*i* in the second plane 20*i*. This second plane is shown in FIG. 15.

Each of the exemplary first plurality of stanchions 12*i* is fixed with one of the second plurality of stanchions 112*i* at the respective first base end 14*i* and the respective second base end 114*i* to define a plurality of stanchion pairs, such as stanchion pair 75*i*. Exemplary stanchion pair 75*i* is thus defined by exemplary first stanchion 12*i* and exemplary second stanchion 112*i*. The exemplary stanchions 12*i*, 112*i* are interconnected at the common base ends 14*i*, 114*i*. Compression at the first arcuate periphery 18*i*, through the common base ends 14*i*, 114*i*, induces movement of the first lens 38*i* and the second lens 138*i* apart from one other. The compression is transmitted through the first plurality of stanchions 12*i* and the second plurality of stanchions 112*i*. By forming the stanchions 12*i*, 112*i* to be mostly straight, unpredictable buckling of the stanchions 12*i*, 112*i* is inhibited.

The straight portions of the stanchions 12*i*, 112*i* are interconnected at the intersection of the respective first base end 14*i* and the respective second base end 114*i*. The exemplary intersection defined by the common base ends 14*i*, 114*i* is bulbous and spherical, as shown in FIGS. 13-15. Thus, a thickness of the exemplary intersection is greater than a combination of the thickness of the straight portion of the first stanchion 12*i* and the thickness of the straight portion of the second stanchion 112*i*. The thickness of each stanchion 12*i*, 112*i* can be defined in a plane that is normal to a central longitudinal axis of each stanchion 12*i*, 112*i*.

A method of elastically deforming the AIOL 10*i*, prior to insertion of the AIOL 10*i* in an eye, can include rotating the first lens 38*i* and the second lens 138*i* relative to one another about the central optic axis 26*i* and thereby wrapping the first plurality of stanchions 12*i* and the second plurality of stanchions 112*i* around one or both of the first lens 38*i* and the second lens 138*i*. Because the stanchions 12*i*, 112*i* are connected to both rings 46*i*, 146*i*, the exemplary stanchions 12*i*, 112*i* will be wrapped in a generally helical path about the central optic axis 26*i*. For the stanchion pair 75*i* and other stanchion pairs of the assembly 10*i*, a length between the first distal end 16*i* of the stanchion of the first plurality of stanchions 12*i* and the second distal end 116*i* of the stanchion of the second plurality of stanchions 112*i* is not greater than outside diameters of both of the first lens 38*i* and the second lens 138*i*, so the stanchion pair 75*i* will extend around a portion of the peripheries of the rings 46*i*, 146*i*, rather than fully around the peripheries of the rings 46*i*, 146*i*.

After rotating, the AIOL 10*i* can be folded in half, such as in a taco shell shape, while retaining the first plurality of stanchions 12*i* and the second plurality of stanchions 112*i* wrapped around the lenses 38*i*, 138*i*. At least one benefit of the coiled stanchions 12*i*, 112*i* is the ability to include multiple stanchions of smaller diameter and greater length than the current art. These stanchions 12*i*, 112*i* therefore can be constructed to be precise and delicate and yet withstand the forces they experience when the lens is coiled, folded and injected into the eye. Two positive power lenses can be separated by a clear fluid medium when in situ and this allows for the design of optics of reduced thickness while maintaining the same refractive power. The savings in cross-sectional volume will also allow for the inclusion of multiple coiled stanchions that remain well protected. In practice, it can be desirable to coil the stanchions and fold the coiled assembly just prior to insertion because long-term storage in a coiled state may limit the desired elastic properties and possibly result in an unpredictable uncoiling unless a temperature-dependent change in mechanical properties was incorporated. For example, slow unfolding of IOLs can warm in the eye after having been kept in a cooled state.

The embodiment of the present disclosure illustrated in FIGS. 13-15 can be viewed as a coiled, double ring embodiment. The embodiment can be configured and sized for placement in the anterior chamber, the ciliary sulcus, or the capsular bag. The embodiment can be configured to support and hold (1) a biometric intraocular sensor to measure and transmit/display data such as intra-ocular pressure, (2) a drug delivery system to release medication within eye, (3) a mechanical supporting device particularly useful for the treatment of glaucoma by opening drainage channels for aqueous humor within the eye and/or for supporting and stabilizing ocular structures such as the iris or lens capsule to facilitate intraocular surgery, and/or (4) supporting an IOL especially an AIOL located either in the sulcus or the capsular bag being dual or single optic and modular or one-piece.

Embodiments of the present disclosure, including a ring member, stanchions, and the haptic passenger, should be made from biocompatible materials that fulfil necessary requirement so strength, flexibility and elastic memory, such requirements varying depending on the ring member morphology. Morphology options can include ring members empty in the center. The ring members may be empty centrally for purposes of modular attachment of haptic passengers so that their circumferences can be made oblate to allow insertion through an incision considerably smaller than their largest diameter in the relaxed state. Uniformly flexible ring members empty in the center can be squeezed into an oval shape or twisted into a figure-of-eight shape. Ring members can have varying flexibility, empty in the center with or without hinges arranged around their periphery. These ring members fold at specified junctions to deform into a heart shape or a double loop. Morphology options can also include ring members that are a solid disc shape. In such case they may be folded into a spiral cylindrical roll, a roughly semicircular (taco) shape along its diameter, concertina fashion through an injector, or a combination of these options to allow insertion through an incision considerably smaller than their largest diameter in the relaxed state.

An array of flexible stanchions can connect the two partly deformable ring members so that the structure can exist in three states. In a vivo state or relaxed state, pairs of stanchions are attached by their distal ends near the periphery of opposite ring members with each stanchion radiating away from the center of the ring and making contact with the base end of its paired stanchion. The paired stanchions are arranged so that they meet in a third plane between the planes of the two ring members. The junctions of the base ends of the stanchion pairs describe an approximate circle (maximum haptic circle) whose diameter is greater than either of the two ring members. The length, angle and flexibility of the stanchions is configured so that the maximum haptic circle matches the perimeter of the ocular anatomy to which the haptic carrier is to attach: anterior chamber angle, ciliary sulcus or capsular bag.

In a coiled state or packed state, the planes of the ring members are closely positioned to each other along the visual axis. In this state, the flexible stanchions are coiled and sequestered between the two ring members whose edges can be shaped so that they approximate a protected circular enclosure when the ring members are drawn closer by rotation. The purpose of the enclosure is to protect the coiled stanchions so that they will not cause damage to or be damaged by ocular structures during insertion and placement. The coiled state is achieved by the ring members being rotated relative to one another in an axis passing through their centers. The rotation has the effect of drawing in and straightening out the base stanchion junctions so that the diameter of the Maximum haptic circle is decreased. The ring member having a smaller diameter can serve as a bobbin around which the stanchions are wound.

The elastic and mechanical properties of the stanchion materials can be of a certain nature so that they coil and uncoil without slipping out of alignment, and a cylindrical frame may need to be placed within the stanchions to guide their coiling in the same manner that drums are used to wind cable. For optimal function a third ring may be used intermediate in size between the ring member having a larger diameter and the ring member having a smaller diameter, placed adjacent to the ring member having a smaller diameter. The third ring can serve as a frame with apertures through which the stanchions pass. Its function is to facilitate coiling or winding of the stanchions by laying and guiding them into proper position in an enclosed space between the third ring and the ring member having a smaller diameter.

In the coiled state, spontaneous uncoiling is prevented by one or both of two mechanisms can be prevented by the planes of the two ring members being in close alignment so that the uncoiling forces are contained by the rigidity of the ring member having a larger diameter until equilibrium is disrupted by the mechanical separation between the planes of the ring members, such as with the use of using a lever instrument of the type commonly used in ocular surgery. Uncoiling can also be prevented by a mechanical stopper such as a pin, knob or wedge that prevents relative movement between the ring members until it is removed.

In the third state, a transition state or insertion state, the coiled ring members can be grasped with an insertion instrument or placed within an injector cartridge so that their dimensions are suitable for passage through a small incision and placement within the eye. This state occurs after the coiled state and before the in vivo state. In this state, the ring members are either flattened if hollow in their center, or folded if not hollow in their center, such temporary deformation being necessary to maximize the ring diameters that may fit within the smallest desirable incision. If a mechanical stopper has been used to maintain the coiled state it is removed once the ring members have been deformed because spontaneous uncoiling is prevented by the deformation and the stopper is no longer necessary. Once the haptic carrier is placed in the desired location it is released and the deformed ring members return slowly to their "coiled state" shape. Once the haptic carrier is close to its coiled state, it will begin to spontaneously uncoil because of the absence of any mechanical stopper or because a lever instrument is then used to separate the ring members. As the planes of the ring members separate, the spontaneous uncoiling of the ring members will cause the stanchions to expand outwards in a plane between the ring member members until the proper anatomical location is reached.

Coiled ring embodiments could feasibly be packaged in the transition state after manufacture and such a "pre-loaded cartridge" has desirable features but has the drawback of placing high demands on the elastic memory of the material requiring relatively precise return to its original shape after having been stored in a stressed state for several months. A compromise solution could be to place and store the IOL inside a sealed cartridge in the unfolded state. The cartridge can be designed so that one side is attached to a syringe or plunger mechanism while the other side has a tapering fluted tube through which the IOL is pushed by the plunger once the tip of the tube has been placed into the incision. The design of the tube folds the IOL so that it fits through the narrow opening and then unfolds once in place.

Coiled-ring embodiments can provide several benefits. The stanchions can be protected by a sleeve during insertion and placement thus preventing crimping and breakage. Ocular structures can be protected by a sleeve so that a smooth profile is presented at sites of friction such as incision, iris and capsule thus preventing damage to these structures. A reduced arc of space is occupied during unfolding, which protects ocular structures. Because the haptic passenger only occupies one plane (in the empty center versions), abrasion against intra-ocular structures is minimized as the IOL unfolds. In prior art, unfolding of the IOL typically occurs in a sweeping arcuate fashion like the movements of wings, which requires a considerable amount of unobstructed volume within the eye if the IOL is not to touch ocular structures other than those it is designed to rest against. It is particularly important to minimize touch or abrasion against the inner lining of the cornea (endothelial layer) and the iris. The coiled ring design with empty center minimizes risk of endothelial cell damage due to uncoiling in one plane rather than arcuate sweep unfolding of prior art. In the case of a solid disc design, even though the IOL will occupy more than one plane when it is folded into a semicircle or taco, the fact that the stanchions will not expand outwards until the IOL has resumed an approximately flat discoid shape means that the volume of excursion within the eye will still be considerable less than in the prior art. Another benefit is that the coiled-ring arrangement can allow for multiple stanchion support (8 or more) rather than conventional two spring haptics or four point plate haptic resulting in better centration and greater stability and reduced risk of dislocation. Further, the coiled-ring arrangement minimizes the volume of material required for the IOL by use of a compact design that allows expansion after insertion, which is ideal for dual optic IOL (accommodating or even non-accommodating) and for modular IOL.

It is noted that one or more embodiments of the present disclosure can be formed from materials that can be modified after the lens assembly is implanted in the eye. For example, at least one mechanical property of at least one of the plurality of stanchions can be modified after the implanting. A mechanical property can at least partially define how the stanchion behaves under loading. In one or more embodiment, the modification can be carried out by applying electromagnetic energy to a portion of the at least one of the plurality of stanchions and thereby modifying an elasticity of the at least one of the plurality of stanchions.

Figure 33:
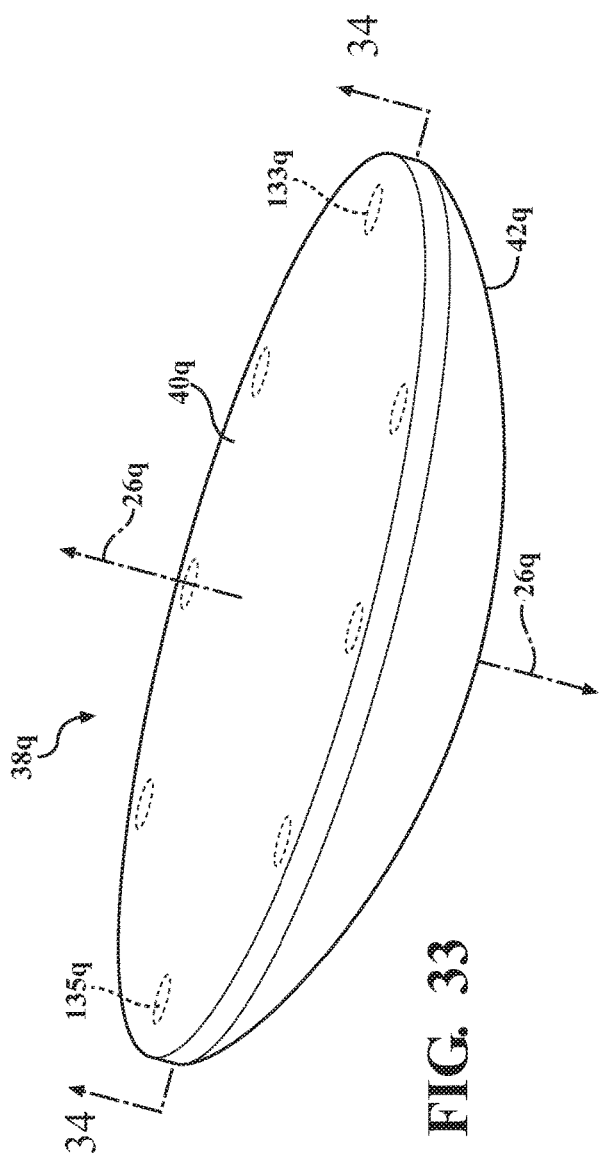
FIG. 33 is a perspective view of a lens that can be included in one or more embodiments of the present disclosure.

For example, FIGS. 33-35 are views of a lens that can be included as a haptic passenger in one or more embodiments of the present disclosure. The lens 38q has a first anterior side 40q and a first posterior side 42q and a first center 44q disposed between the first anterior side 40q and the first posterior side 42q. A central optic axis 26q extends through the first center 44q.

The circles in dash line, such as referenced at 133q and 135q, represent potential areas to target with electromagnetic energy, such as with a femtosecond laser. FIG. 34 is a cross-sectional view taken through section lines 34-34 in FIG. 33 and shows the lens 38q prior to the application of the laser at areas 133q and 135q. FIG. 35 is a cross-sectional view analogous to the view of FIG. 34, but after the application of energy with the laser at areas 133q and 135q. The application of the laser has changed the shape of the lens 38q to permanently contract at areas 133q and 135q. FIGS. 36A-36D are various patterns for the application of energy to portions of a lens to change the shape of the lens.

The selective application of energy to various points in the periphery of the IOL (after pupillary dilation ion postoperative follow up) makes it is possible to alter the shape of the gradient of the graph shown in FIG. 23. The selective application of energy to various points along the periphery of the IOL also makes it is possible to alter the overall power of the AIOL in the non-accommodated state to adjust for errors in lens power calculations. For example, the entire lens could be made more convex (increased positive power) by laser energy contraction at 4 or more points at the periphery spaced 90 degrees from each other. The selective application of energy at various points in the periphery of a lens of an AIOL can also make it is possible to alter the toric power of the AIOL for residual astigmatic refractive errors, such as by applying laser energy at two or more points 180 degrees from each other to alter the cylindrical power of AIOL by steepening its curvature in the desired meridian. The selective application of energy at various points in the periphery of a lens of an AIOL can also be desirable to correct asymmetric astigmatism by applying laser energy asymmetrically to one or more spots at the desired axis. The selective application of energy at various points in the periphery of a lens of an AIOL can also be desirable to correct Higher Order Aberrations (HOAs), irregular astigmatism, and/or other complex refractive errors that can be measured by wavefront analysis, such as Shack-Hartmann aberrometry. In another example, a complex pattern of applications can be applied at the points determined by Zernike polynomials measured by wavefront analysis. See, for example, https://en.wikipedia.org/wiki/Aberrations_of_the_eye.

Figure 37:
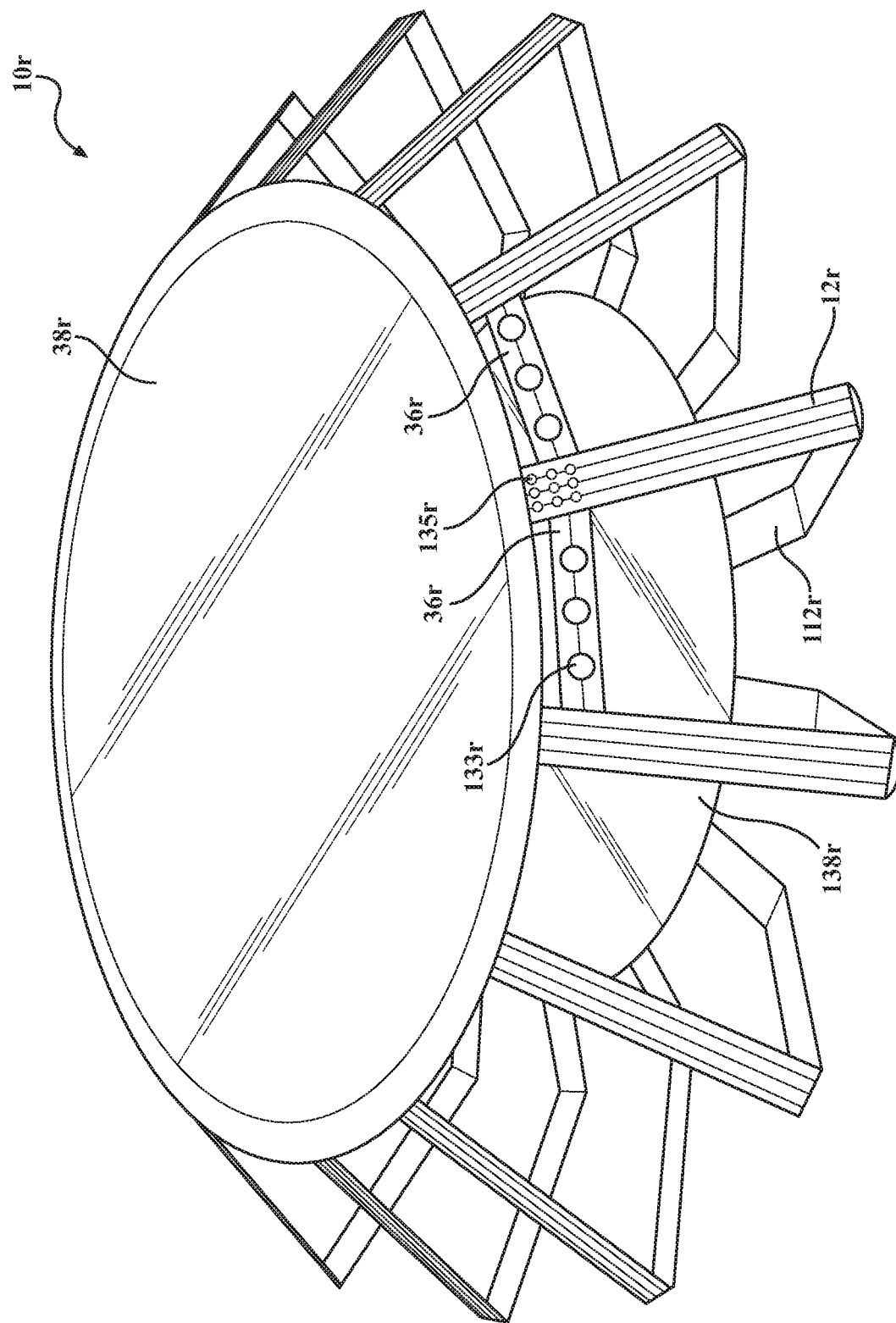
FIG. 37 is a perspective view of another exemplary embodiment of the present disclosure.

FIG. 37 is a perspective view of another exemplary embodiment of the present disclosure in which a laser can be applied to modify the optical characteristics of an implanted IOL. An assembly 10r includes lenses 38r and 138r. The assembly 10r also includes first and second stanchions 12r, 112r interconnecting the lenses 38r, 138r. The assembly 10r also includes linking members, such as linking members 36r, interconnecting adjacent stanchions 12r. The stanchions 12r and the linking members 36r can include areas formed of material that can modified, such as referenced at areas 133r and 135r. These areas are represented by circles visible on the stanchions 12r and the linking members 36r. Contraction at these areas can modify the positioning and relative biasing of the lenses 38r, 138r and thereby adjust optical properties of the assembly 10r for the user. In other embodiments of the present disclosure, the application of energy can have the opposite effect on the material in order to the alter optical properties of the lens or the AIOL or the IOL, such as causing the material to expand or become less rigid.

One or more embodiments of the present disclosure can provide a Haptic design that maintains stability of its Haptic Passenger in the ciliary sulcus during ocular movement due to its shape and size. The haptic can be composed of stanchions which attach to the circumference of a fixed ring member at one end, and whose other ends describe a circular oval that forms a variable "virtual ring." The planar separation of the fixed ring member and the virtual ring can be dependent on the angles formed by the stanchions relative to the rings, while their lengths can remain essentially constant.

One or more embodiments of the present disclosure can prevent dislocation by gravity, inertia and flow of intraocular fluids, and mechanical forces exerted by adjacent intraocular structures both static and dynamic. The stability can be achieved by the size, shape, and/or composition of the haptic arrangement with the size being selected on the basis of pre-operative measurements made on each patient. The components that define the virtual ring (delineated by base end of stanchions) can be arranged so that they form a an oval circle of a variable diameter whose maximum extent corresponds to that of the ciliary sulcus (SSD) when CBA is relaxed and whose minimum extent corresponds to the diameter of the ciliary sulcus (SSD) when CBA is maximally activated. The said diameter can be oval shaped rather than strictly circular, to conform to the shape of the human ciliary sulcus.

The virtual ring of contact elements (base end of stanchions) can be made of a size and shape that fit securely into the ends of the ciliary sulcus without slippage or biological damage. The material can be bio-compatible and deformable but have sufficient structural memory to be folded prior to insertion into the eye through a small corneal incision and then unfolded into position within the ciliary sulcus of the eye.

The haptic design can thus be suited by dimensions and material of composition for stable and accurate surgical placement in the ciliary sulcus of the human eye between the anterior face of the lens capsule and zonules, and the posterior surface of the iris. A first anatomical change caused by CBA can be utilized by one or more embodiments of the present disclosure as shape-changing mechanisms is the decrease in diameter of the ciliary sulcus (perpendicular to the visual axis) due to annular contraction. This is measured as a decrease in the sulcus to sulcus diameter (SSD) which causes the virtual ring to contract, increasing separation of between fixed and virtual rings and so moving the fixed ring member and haptic passenger forward towards the cornea relative to the plane of the SSD circle. A second anatomical change can be anterior movement of the ciliary sulcus due to CB contraction. This causes forward movement of the plane of the SSD circle relative to the fixed points of the ocular globe caused by ciliary muscle contraction, resulting in forward movement of the virtual ring towards the cornea, which is additive in effect to the forward movement of the fixed ring member caused by reduction in SSD. A third anatomical change can be anterio-posterior pressure or compression at the ciliary sulcus between the zonules and the posterior surface of the iris due to forward movement of the ciliary body. Anterio-posterior pinching occurring in the ciliary sulcus due to annular contraction of the ciliary muscle results in increased compression at the ciliary sulcus from anatomical "crowding" against the posterior surface of the iris.

Ciliary sulcus placement effectively harnesses the three main functional elements of the ciliary muscle (longitudinal, oblique and annular) which on ciliary muscle contraction generate mechanical force that is matched to movements of single or multiple optic IOLS. Ciliary body contraction forces can be thus used to convert contraction to anterior displacement of the ring member of fixed circumference offset from the plane of the contracting circle. May be single or double (dual optic), convert contraction to move pins or pistons relative to a tangential bar or ring, and squeeze fluid. This allows a single or dual optic design in the configuration whereby equatorial reduction in circumference of an approximately circular anatomical trench associated with the ciliary muscle allows purchase on multiple contact points causing a corresponding reduction in circumference of the circle joining the contact points so that the contact pints contract in relation to each other without the need for sliding relative to the circular anatomical trench. The contact points serving as hinges whose relative movement is translated into variation of optical power to allow for close focusing on objects when accommodation is voluntarily initiated by contraction of the ciliary muscle. The movement described can be either increased separation of multiple optics of the IOL or forward movement of the center of a single optic.

One or more embodiments of the present disclosure can provide a Haptic design that is well suited for safe insertion through a small incision by being composed of multiple spoke like flexible elements arranged in a radial fashion connecting at least one fixed ring member to a virtual ring.

One or more embodiments of the present disclosure can define a star-like structure with individual radii converging at a central *nexus* to support a Haptic Passenger. Intermediate radii can be joined by a circular band of varying width and thickness running tangentially to the radii serving to shield and space out the elements, provide redundant support for safety, and prevent protrusions or deformations that catch against biological structures during injection and unfolding, presenting a planar profile for insertion into ciliary sulcus. The periphery of the radii can serve as contact points against anchoring structures within the eye.

The anterior-posterior hinged struts (stanchions) incorporated into "cogwheel" shaped sheets joined at edges are amenable to work in the ciliary sulcus. The requirement of predictable flexibility and elastic memory retention in response to small variations in mechanical forces needed when the lens is in situ, conflicts with the requirement for extreme deformability needed to fold and unfold the lens. The designs and shapes described above is best suited to overcome these difficulties.

Other benefits include efficient mechanical linkage with ciliary body contraction whether placed in capsular bag or ciliary sulcus. Multiple, flexible interconnected struts provide error correction for asymmetry and minor mis-positioning as well as some redundancy in case of damage during insertion. Small bulk allows for easy folding for insertion. Further, the performance does not depend on integrity of capsular bag (or zonules when placed in sulcus).

One or more embodiments of the present disclosure can provide a Haptic design that moves in harmony with internal ocular structures. The haptic flexes, contracts, expands and changes shape in a reversible manner in response to, and while in apposition with dynamic intraocular structures such as annular muscles, elastic capsules, supporting fibers and ocular connective tissue without presenting mechanical resistance that may damage ocular structures during such repeated and reversible mechanical changes.

A desirable aspect of one or more embodiments of the present disclosure can be point-to-point contraction linking (PPCL) in which the contact points are multiple enough to distribute force and support, spaced horizontally, vertically and all other important intermediate meridians, and large enough to provide support and make contact without damage but small enough and/or curved to offer minimal resistance to and friction against elastic dynamically contracting intra-ocular structures such as annular muscles or elastic capsules.

One or more embodiments of the present disclosure can provide a Haptic design whose cyclic movements in response to internal ocular structures can be used to predictably alter the force, tension and spatial separation between its constituent elements.

One or more embodiments of the present disclosure can provide a Haptic design composed of elements that are rigid and connected at certain points but flexible and elastically jointed at others so that may move in relation to one another and the eye but maintain stable fixation overall once implanted in the eye.

One or more embodiments of the present disclosure can provide a Haptic design that compresses in response to CB contraction in a predictable manner without significantly impeding CB contraction by virtue of point-to-point deformability. By thus compressing in response to CB contraction, one or more embodiments of the present disclosure can provide a Haptic design that links anatomical changes occurring during CBA, to variations in mechanical forces between the elements of the haptic. By virtue of the variation of force, tension and spacing between the elements of the rigid but elastically jointed haptics applies forces on the Haptic Passenger.

One or more embodiments of the present disclosure can provide a Haptic design in which the cyclic variations of force, tension and separation between its constituent elements can be linked to predictable variations in the properties of the Haptic Passenger. In the specific case where the Haptic Passenger is an optical lens system or "optic," the power of the optic can be reversibly and predictably varied through various mechanisms depending on the design of the lens system.

An approach for predictably and reversibly varying optical power in an IOL that is focused for distance in the non-accommodative state in order to achieve IOLA (beyond pseudo-accommodation) in various biologically feasible IOL systems include a "Simple lens." The power of a simple lens can be reversibly varied by changing its location relative to the optical center of the eye by vaulting or moving forward during CBA. This is achieved in the Jester's collar design (ring member with stanchions having decreasing width away from the ring member) by forward movement of the optic caused by point-to-point contraction.

An approach for predictably and reversibly varying optical power in an IOL that is focused for distance in the non-accommodative state in order to achieve IOLA (beyond pseudo-accommodation) in various biologically feasible IOL systems also includes a "Compound lens." The power of a dual optic IOL can be reversibly varied by changing the separation of the optics. This can be achieved through the double Jester's collar design or in the single Jester's collar design by any other means whereby one optic is fixed closer to the haptics at their contact points and the other optic further away so that CB contraction results in separation of the two optics.

An approach for predictably and reversibly varying optical power in an IOL that is focused for distance in the non-accommodative state in order to achieve IOLA (beyond pseudo-accommodation) in various biologically feasible IOL systems also includes a "Flexible lens." The power of a flexible lens can be reversibly varied by pinching, squeezing or compressing the flexible periphery of the lens to cause increased power by increasing the relative curvatures or relative separation of the anterior and posterior surfaces. In the Jester's Collar design this effect can be achieved by giving the optic element a flexible periphery and mounting it between the flaps of the collar (the stanchions extending away from the ring member) so that points on the flexible periphery are attached to the inner surface of the haptic elements and become compressed during CBA, in turn compressing the periphery and achieving the desired power change.

An approach for predictably and reversibly varying optical power in an IOL that is focused for distance in the non-accommodative state in order to achieve IOLA (beyond pseudo-accommodation) in various biologically feasible IOL systems also includes a "Biological lens." A biological lens as described for the purposes of the present disclosure is that which most closely approximates the natural, youthful crystalline lens of the human eye. Technological constraints have hitherto prevented the manufacture of such a lens for prosthetic use. If such prosthesis could be manufactured and assembled within the eye, it could be fixed in place between the haptic elements in the same fashion as that described for the flexible lens above and could have its power reversible varied in the same fashion by compression of its periphery between the haptics.

An approach for predictably and reversibly varying optical power in an IOL that is focused for distance in the non-accommodative state in order to achieve IOLA (beyond pseudo-accommodation) in various biologically feasible IOL systems also includes a "Neo-biological lens." A neo-biological lens as described for the purposes of the present disclosure would be an IOL whose power can be varied by electronic or photo-chemical means either across the entire material of the lens, or selectively in certain regions. Practical application of this type of lens is limited by the available technology, but should it be manufactured, its power could be controlled in many ways by the haptic linked to CBA as described above.

One or more embodiments of the present disclosure can provide a Haptic design which when manufactured to the appropriate dimensions is well suited for placement within the capsular bag of the eye. One or more embodiments of the present disclosure can provide a Haptic design allowing for attachment of the Haptic Passenger after the Haptic has been implanted in the eye so that the Haptic can be placed within the eye before the insertion of the Haptic Passenger. One or more embodiments of the present disclosure can provide a Haptic design that when placed prior to capsule rhexis provides stability and support of the lens capsule, which facilitates the performance of surgery. One or more embodiments of the present disclosure can provide a Haptic design that when placed prior to capsule rhexis can be adapted to improve pupillary dilation and thus facilitates the performance of surgery.

For desirable placement and harnessing of the ciliary body power, it may be desirable to have a two component IOL system in which the haptic passenger (a single or dual optic IOL) is attached within the eye to a ring-shaped haptic. The haptic itself is circular flat disc open in the center which can be implanted in the ciliary sulcus after an incision is made but before the anterior capsule is opened (capsulorhexis, or simply rhexis). This ring would confer some additional benefits in performance of the surgery such as maintaining AC depth and preventing rapid fluctuations to protect zonules, holding anterior capsule taught to improve capsulorhexis, providing a potential platform for (detachable) iris hooks or iris lip to improve pupillary dilation, providing secure anchor linked to ciliary sulcus to against which optic/haptic complex can be placed to transmit kinetic force of ciliary muscle contraction and convert it to optical changes in IOL power, and providing a ring member for potential post-operative mechanical/optical property modification by selective application of laser energy.

One or more embodiments of the present disclosure can provide a haptic that can be implanted separately from the haptic passenger, which has the advantage that it can be placed within the eye without the optic (or other haptic passenger). If the haptic passenger does not present an obstruction to surgery (such as that presented by a centrally located optic), it may be implanted at an earlier stage of surgery and thus facilitate subsequent steps of the surgical procedure. The modular IOL allows a two stage implantation. A first benefit of the two stage implantation are that it allows the haptic to be securely placed and seated in the ciliary sulcus before further surgical steps distort the anatomy around the ciliary sulcus. A haptic unfolded behind the iris is almost certain to become located in the ciliary sulcus because its posterior migration is limited by the anterior surface of a lens. It cannot pass beyond the anterior capsule, as the anterior capsule of the lens is still intact at this stage of the surgery. A second benefit is that the haptic can incorporated benefits of other surgical devices without the separate need for these devices, such as pupil expanders and anterior chamber stabilizing rings.

Design considerations for haptic in modular (two stage) IOL system include the area of touch wherein the slant of ring member and curve of the stanchions can be optimized by mathematical modeling to enhance refractive change per unit of ciliary muscle contraction, optic configurations such as can use single, dual or multiple optic configurations to simulate accommodation, allowing the ring member to have a gap (open or horseshoe shape) to allow for easier introduction past iris and assist with iris displacement or be a continuous circle, the inside edge can have a groove to accommodate optic, and the optic can have lip to fix against ring member at one end and two other lips or snaps to fix into place.

One or more embodiments of the present disclosure can provide a Haptic design that occupies and stretches the area adjacent to the ciliary body of the eye in a manner that may increase aqueous humor outflow and treat glaucoma following surgery. This is a novel concept and does not rely on a modular, two stage IOL (or any of the other elements of the ring member design other than ciliary sulcus placement) but on the design of the stanchion elements and interconnecting bands/rings so that they cause stretching and tension at a specific point near the base of the iris to open the aqueous humor drainage channels of the eye. The goal is to mimic an effect of certain glaucoma medicines that achieve the same result by causing contraction of the ciliary muscle. Perfection of this embodiment will require description of the optimum design of the base end of the haptics that sit in the sulcus, and perhaps other embellishments so it may best to allude to it in case details distract from the AIOL functioning.

One or more embodiments of the present disclosure can provide a Haptic design that allows for post-operative adjustment of amplitude of IOLA by selective application of energy to its elements to alter their elasticity, tension, relative separation placement within the eye.

One or more embodiments of the present disclosure can provide a Haptic design that allows for post-operative adjustment of lens spherical and or toric power by selective application of energy to its elements to alter their elasticity, tension, relative separation placement within the eye. Embellishments made possible by selective application of energy to the haptics through dilated pupils include the ability to modify spherical power, the ability to modify toric power, and the ability to modify asphericity.

An optic design (either as a single optic design or one or both of a dual optic design) which can be incorporated into a single stage or modular IOL system and which can be part of an AIOL or conventional IOL in which the Haptic Passenger is an optic in the form of a flexible lens system having a periphery containing components that can expand or contract in response to selective application of energy, whose expansion and contraction alters the central curvature and thickness of the lens. Embellishments made possible by selective application of energy at the periphery of at least one of the optics through dilated pupils include the selective application of energy at the optic periphery can alter the optical properties of the lens optic by increasing the pinching action of rivet type supports connecting the anterior and posterior surfaces of an optic, separated by a viscolelastic fluid. This arrangement allowing post-operative treatment that allows modification of the following lens optical properties: spherical power, cylindrical (Toric) power and axis to correct astigmatism, and correction of irregular astigmatism and higher order optical aberrations.

There are a number of stanchion contact designs used to translate the mechanical forces generated by CBA into IOLA by enhancing optic movement contemplated by the present disclosure including various contact designs, rigidity changes and curvatures.

One or more embodiments of the present disclosure can provide a Haptic design that by virtue of allowing later attachment of the Haptic Passenger also allows for its own injection into the eye in the form of a helical strip. The flexible strip may be inserted into the eye using an instrument or injector and once injected into the eye forms a closed circular ring, forms a "C" shaped ring, or forms a 'C'" shaped ring whose ends can be joined to form a closed circular ring.

One or more embodiments of the present disclosure can provide a Haptic design that by virtue of allowing later attachment of the Haptic Passenger also allows for its own insertion into the eye through a small incision in the form of a circle with at least four points of elastic articulation. This method of articulating the relatively rigid segments of the circle allows the Haptic to fit through a narrow incision whilst maintaining enough rigidity to be guided behind the iris and preventing excessive disruption of the space between the iris and the lens capsule.

Because of the anatomy of the ocular globe, a small corneal incision, if constructed in a step like fashion at the correct location with a special instrument, can be self-sealing so that the pressure of fluid within the eye will keep it closed until it heals. The upper limit to the length of such an incision is generally considered to be no more than about three millimeters. It can be desirable that an IOL optic be at least about five millimeters in diameter to focus light on the retina. A smaller optic could cause glare, reflections, and other troublesome symptoms. To span the diameter of the capsular bag or ciliary sulcus and desirably be suspend the optic in place, the distance between opposite ends of the haptics can be about nine millimeters (in the case of the sulcus) and about twelve millimeters (in the case of capsular bag placement). Any device that requires stable placement in the sulcus or capsular bag will likely be subject to these constraints. Therefore, any IOL, however complex or elegant in design, will have extremely limited utility unless it can be placed within the eye through a small incision and also meet the minimum size requirements of the optic and haptic diameters. Several other anatomical and physiological factors place practical constraints on intraocular device design. Embodiments of the present disclosure can meet these practical constraints and provide patentable utility.

In some embodiments, the intended haptic passenger can be a single optic IOL. The embodiment can be one piece. The embodiment can include a single ring member. The single ring member can be continuous. The mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The nature of the optics (the optical properties) can be adjustable after surgery.

In some embodiments, the intended haptic passenger can be a single optic IOL. The embodiment can be one piece. The embodiment can include more than one ring member. Each of the ring members can be continuous. The mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge. The enhanced mechanism for accurate stanchion placement once the embodiment is inside the eye can be an uncoiling motion, such as could occur with the embodiment shown in FIG. 13. The nature of the optics can be adjustable after surgery. Optic rotation during CBA would defeat some of the modification utility (especially astigmatism adjustment) unless the embodiment when uncoiled was configured to allow movement of the optics without rotation.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include a single ring member that is continuous. The mechanism of morphological change allowing for entry of the single ring member and stanchions through small corneal incision can be uniform flexibility, where the ring member and stanchions are deformable and placed behind iris with forceps or injector and released to unfold into position. Alternatively, the mechanism of morphological change can be rigid arcs separated by hinges, defining a collapsible ring member. The nature of the optics can be adjustable after surgery.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include a single ring member and the single ring member can each be discontinuous. The mechanism of morphological change allowing for entry of the single ring member through small corneal incision can be the ring member being a horse shoe shape. The ring member can be at least partially elastic and flexible. One end of the ring member can be placed into the anterior chamber through the incision, guided behind dilated iris, and the trailing end can then be guided through incision in a horizontal "Fosbury flop" manner so that ring member only has to flex partially. Alternatively, the embodiment can be implanted with an injector cartridge. The at least partially-flexible ring member can be placed into a curved syringe-type injector. A plunger can be used to push the embodiment into the eye, which reforms its curve as its leading end is guided under the iris. The curve and rotation of the injector assists in laying down the embodiment into place. The injector tip can be rotated to allow placement with minimal trauma. The nature of the optics can be adjustable after surgery.

In some embodiments, the intended haptic passenger can be a single optic IOL that is modular. The ring member and stanchions can be one component and the haptic passenger can be mounted on the ring member and stanchions after the ring member and stanchions have been positioned in the eye. The embodiment can include more than one ring member and the ring members can each be continuous. The mechanism of morphological change allowing for entry of the ring members through a small corneal incision can be can be uniform flexibility, where the ring member and stanchions are deformable and placed behind iris with forceps or injector and released to unfold into position. The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The enhanced mechanism for accurate stanchion placement once the embodiment is inside the eye can be an uncoiling motion, such as could occur with the embodiment shown in FIG. 13. Alternatively, the mechanism of morphological change can be rigid arcs separated by hinges, defining a collapsible ring member. The nature of the optics (the optical properties) can be adjustable after surgery. The nature of the optics can be adjustable after surgery.

In some embodiments, the intended haptic passenger can be a multi-optic IOL that is one-piece or modular. Such embodiments can include a single ring member or more than one ring members. The rings of a one-piece or modular embodiment can be continuous. For one-piece embodiments, the mechanism of morphological change allowing for entry of the single ring member through small corneal incision can be limited by the incorporated IOL optic, which should be in the shape of a disc, plate or star that is folded. Fold configurations may be like a taco, roll, or concertina. Each fold method can use forceps or an injector cartridge.

The enhanced mechanism for accurate stanchion placement once the embodiment is inside the eye can be a star-shaped profile of the haptic (a result of the ring member and stanchions), distinct rounded contact points defined by the base ends of the stanchions, with connections between the base ends presenting a rounded planar profile with intervening fenestrations to allow flexing of the haptic and the flow of intraocular fluids. The enhanced mechanism for accurate stanchion placement once the embodiment is inside eye can also be an uncoiling motion, such as could occur with the embodiment shown in FIG. 13. The nature of the optics can be adjustable after surgery. Optic rotation during CBA would defeat some of the modification utility (especially astigmatism adjustment) unless the embodiment when uncoiled was configured to allow movement of the optics without rotation. The nature of the optics can be can be adjustable after surgery.

In some embodiments of the present disclosure, a plurality of stanchions can be interconnected with a ring member and the embodiment can omit a lens. Such an embodiment can be implanted in a patient's eye without a lens. Such an embodiment can be placed in the ciliary sulcus and thereby increase aqueous humor outflow by stretching open the trabecular meshwork. Such an embodiment, when placed in the ciliary sulcus, can also decrease aqueous humor production by ciliary body. Any of the structural embodiments of the present disclosure can be placed in the ciliary sulcus without a lens.

Figure 16:
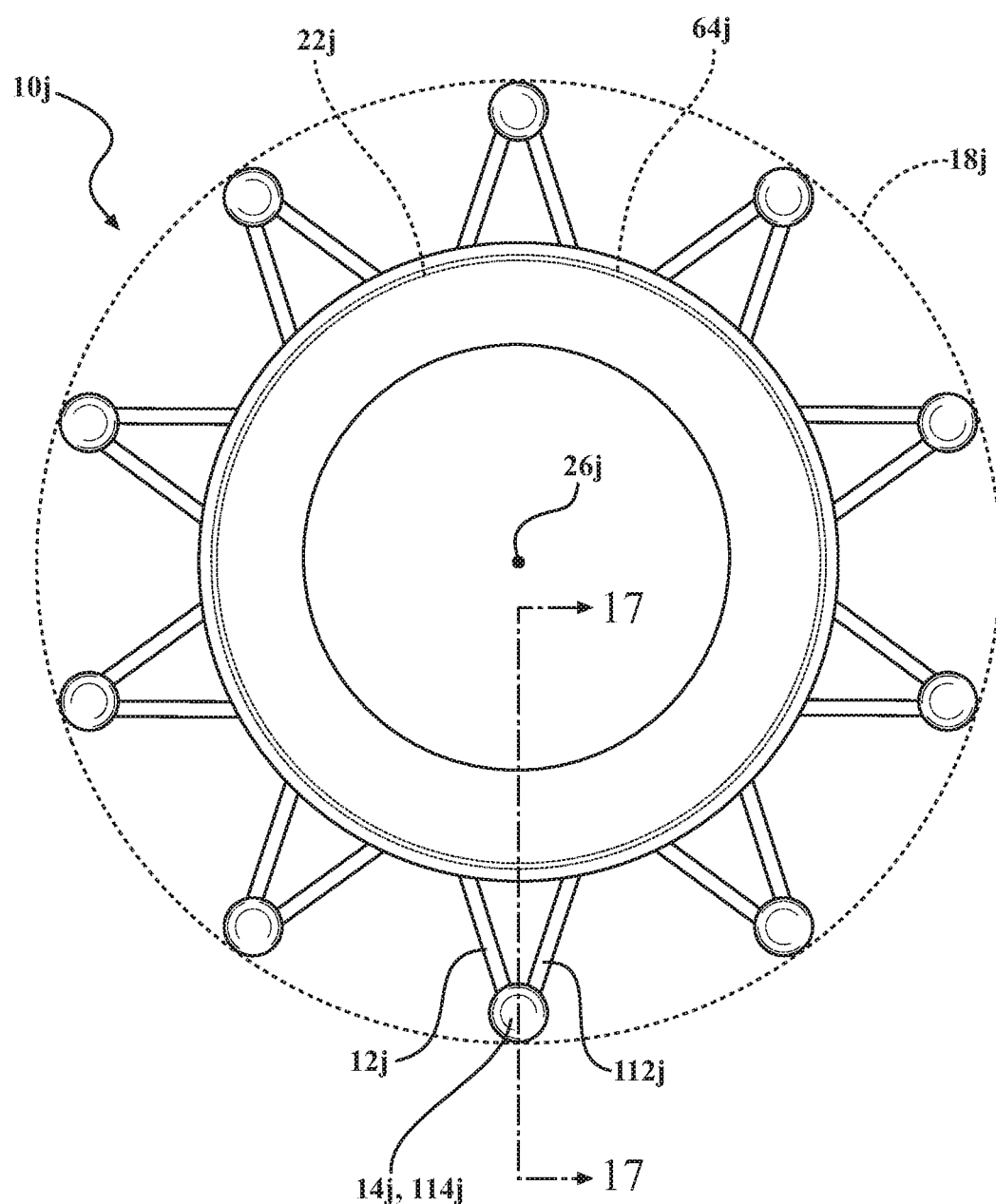
FIG. 16 is a top view of another exemplary embodiment of the present disclosure in an uncoiled configuration.
Figure 17:
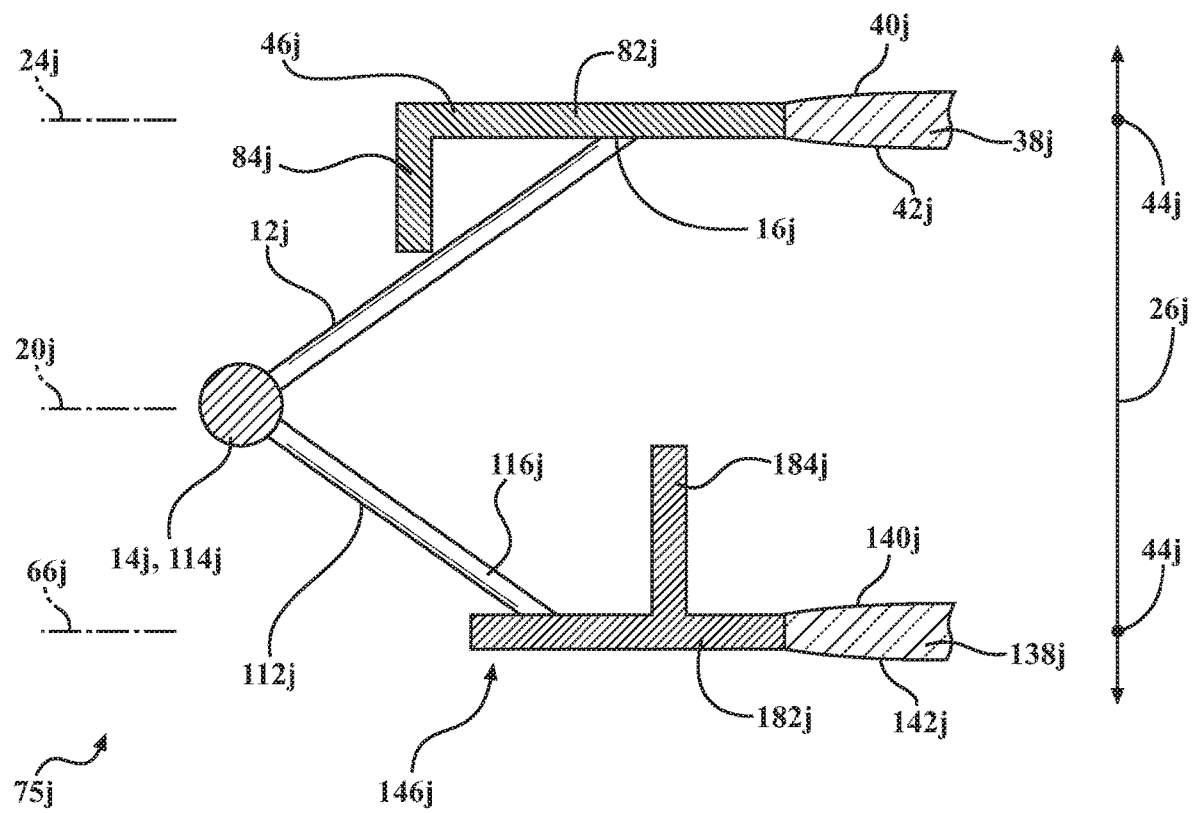
FIG. 17 is a cross-section taken at section lines 17-17 in FIG. 16.

In another alternative embodiment, as shown in FIGS. 16-19, an AIOL 10j can include a first plurality of stanchions each extending a first distance between a base end and a distal end, such as stanchion 12j with base end 14j and distal end 16j. The embodiment of the present disclosure illustrated in FIGS. 16-19 can be viewed as a double ring embodiment capable of being coiled. The base ends 14j can be disposed in spaced relation to one another about a first arcuate periphery 18j extending in a first plane 20j. The distal ends 16j can be disposed about a second arcuate periphery 22j extending in a second plane 24j. The first plane 20j can be spaced from the second plane 24j in a posterior direction along a central optic axis 26j. The first arcuate periphery 18j can have a greater radius than the second arcuate periphery 22j. Each of the first plurality of stanchions 12j can be straight over at least most of the first distance. Each of the exemplary first plurality of stanchions 12j is straight over the first distance, as shown by FIGS. 16 and 17.

The AIOL 10j can also include a ring member 46j. The ring member 46j can be interconnected with each of the plurality of distal ends 16j. The ring member 46j can include a disc portion 82j and a flange portion 84j. A haptic passenger such as lens 38j can be mounted on the ring member 46j after the ring member 46j and the stanchions 12j have been implanted in the eye, or before. The exemplary first lens 38j has a first anterior side 40j and a first posterior side 42j and a first center 44j disposed between the first anterior side 40j and the first posterior side 42j. The central optic axis 26j extends through the first center 44j. The exemplary first lens 38j is connected with each of the plurality of first distal ends 16j through the ring 46j.

The AIOL 10j can also include a second plurality of stanchions each respectively extending a second distance between a second base end and a second distal end, such as stanchion 112j having base end 114j and distal end 116j. Each of the second plurality of stanchions 112j can be straight over at least most of the second distance. Each of the exemplary second plurality of stanchions 112j is straight over the first distance, as shown by FIGS. 16 and 17. Each of the base ends 114*j* of the second plurality of stanchions 112*j* can be interconnected with one of the base ends 14*j* of the first plurality of stanchions 12*j* at intersections and thus be spaced from one another about the first arcuate periphery 18*j*. The second distal ends can be disposed about an arcuate periphery 64*j* extending in a plane 66*j* that is spaced from the plane 20*j* of the second base ends 114*j* along the central optic axis 26*j*. The first arcuate periphery 18*j* can have a greater radius than the arcuate periphery 64*j* of the second distal ends 116*j*.

The AIOL 10*j* can also include a ring member 146*j*. The ring member 146*j* can be interconnected with each of the plurality of distal ends 116*j*. The ring member 146*j* can include a disc portion 182*j* and a flange portion 184*j*. The flange portion 184*j* can be positioned radially inward of the flange portion 84*j*. A haptic passenger such as lens 138*j* can be mounted on the ring member 146*j* after the ring member 146*j* and the stanchions 112*j* have been implanted in the eye, or before. The exemplary second lens 138*j* has a second anterior side 140*j* and a second posterior side 142*j* and a second center 144*j* disposed between the second anterior side 140*j* and the second posterior side 142*j*. The central optic axis 26*j* extends through the second center 144*j*. The exemplary second anterior side 140*j* confronts the first posterior side 42*j* of the first lens 38*j*. The exemplary second lens 138*j* is connected with each of the plurality of second distal ends 116*j* through the ring 146*j*. In other embodiments, the second lens 138*i* can be directly connected with the plurality of second distal ends 116*j*.

Each of the exemplary first plurality of stanchions 12*j* is fixed with one of the second plurality of stanchions 112*j* at the respective first base end 14*j* and the respective second base end 114*j* to define a plurality of stanchion pairs, such as stanchion pair 75*j*. Exemplary stanchion pair 75*j* is thus defined by exemplary first stanchion 12*j* and exemplary second stanchion 112*j*. The exemplary stanchions 12*j*, 112*j* are interconnected at the common base ends 14*j*, 114*j*. Compression at the first arcuate periphery 18*j*, through the common base ends 14*j*, 114*j*, induces movement of the first lens 38*j* and the second lens 138*j* apart from one other. The compression is transmitted through the first plurality of stanchions 12*j* and the second plurality of stanchions 112*j*. By forming the stanchions 12*j*, 112*j* to be mostly straight, unpredictable buckling of the stanchions 12*j*, 112*j* is inhibited.

The exemplary intersection defined by the common base ends 14*j*, 114*j* is bulbous and spherical, as shown in FIGS. 16-19. Thus, a thickness of the exemplary intersection is greater than a combination of the thickness of the straight portion of the first stanchion 12*j* and the thickness of the straight portion of the second stanchion 112*j*. The thickness of each exemplary stanchion 12*j*, 112*j* is defined in a plane that is normal to a central longitudinal axis of each stanchion 12*j*, 112*j*.

The stanchions 12*j* each extend along a first path transverse to and spaced from the central optic axis 26*j* in a first plane transverse the central optic axis 26*j*. FIG. 16 is a view of such a plane. Each of the second plurality of stanchions 112*j* extends along a second path that is transverse to and spaced from the central optic axis 26*j* in the first plane. The first path and the second path are mirrored with respect one another in a second plane containing the central optic axis 26*j*. This second plane is shown in FIG. 17.

Figure 18:
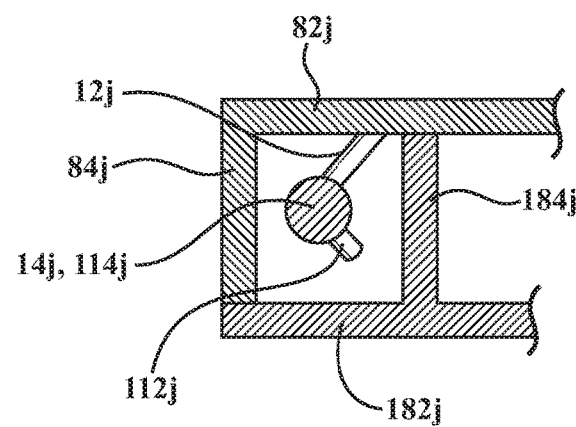
FIG. 18 is a cross-section analogous to FIG. 17 but of the embodiment in a coiled configuration.
Figure 19:
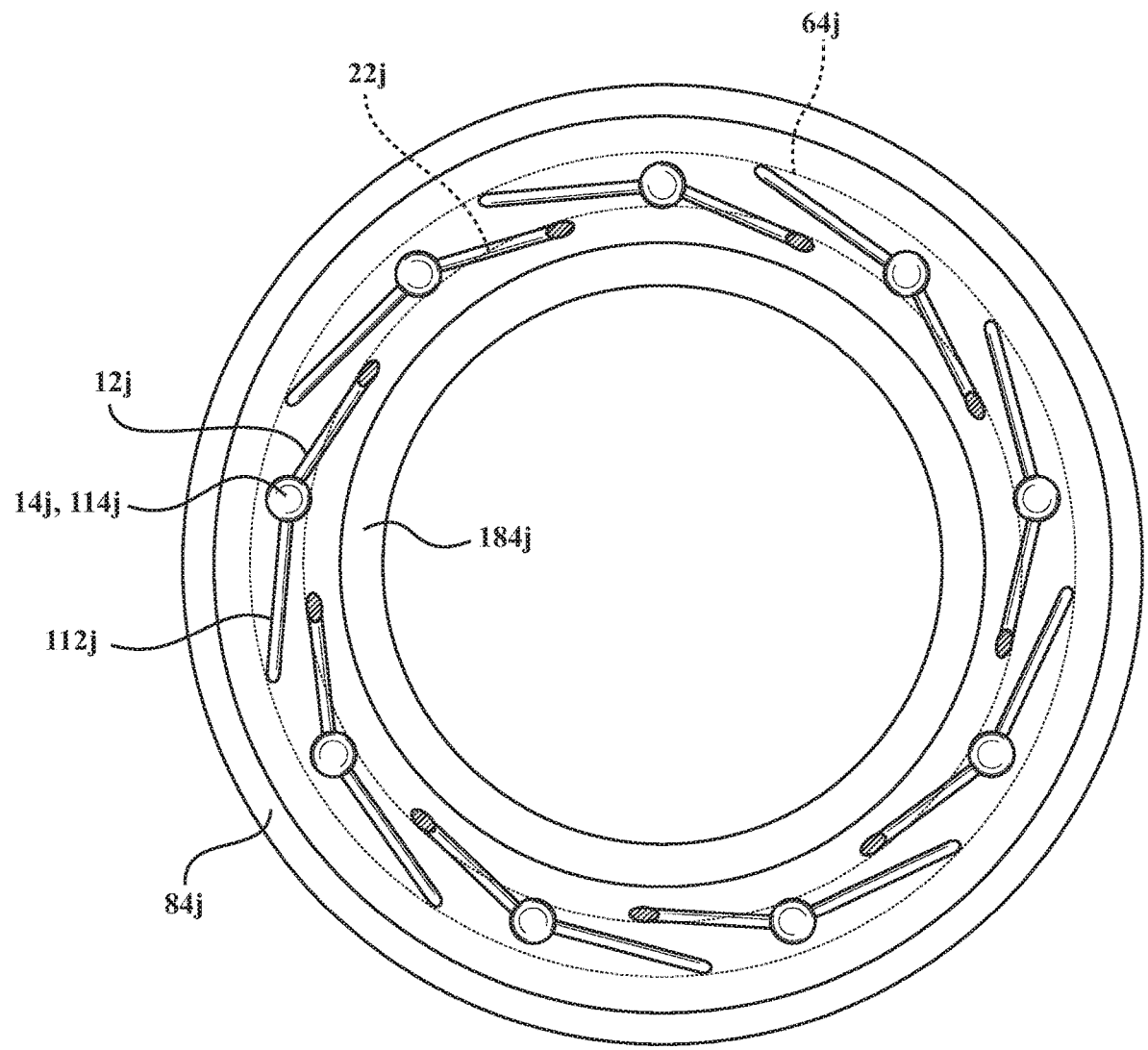
FIG. 19 is a top view of the embodiment shown in FIGS. 16-18, but of a top portion removed and in the coiled configuration.

A method of elastically deforming the AIOL 10*j*, prior to insertion of the AIOL 10*j* in an eye, can include rotating the first lens 38*j* and the second lens 138*j* relative to one another about the central optic axis 26*j* and thereby drawing the first plurality of stanchions 12*j* and the second plurality of stanchions 112*j* in between the first lens 38*j* and the second lens 138*j*. For the stanchion pair 75*j* and other stanchion pairs of the assembly 10*j*, a length between the first distal end 16*j* of the stanchion 12*j* and the second distal end 116*j* of the stanchion 112*j* is not greater than outside diameters of both of the first lens 38*j* and the second lens 138*j*, so the stanchion pair 75*j* will extend around a portion of the peripheries of the rings 46*j*, 146*j*, rather than fully around the peripheries of the rings 46*j*, 146*j*. As best shown in FIG. 19, the stanchions 12*j*, 112*j* are elastically deformed into a substantially straight line when the assembly 10*j* is coiled. As best shown in FIG. 18, the stanchions 12*j*, 112*j* are enclosed in a cavity that is defined along the central optic axis 26*j* by the rings 46*j*, 146*j* and is defined radially relative to the central optic axis 26*j* by the flange portions 84*j*, 184*j*. After rotating, the AIOL 10*j* can be folded in half, such as in a taco shell shape, while retaining the first plurality of stanchions 12*j* and the second plurality of stanchions 112*j* positioned between the lenses 38*i*, 138*i*.

FIGS. 16 and 17 thus show the embodiment in an uncoiled configuration and FIGS. 18 and 19 show the embodiment in a coiled configuration. The embodiment can further be folded. The ring members 46*j* and 146*j* can be rotated relative to one another about the axis 26*j* to draw the stanchions 12*j*, 112*j* into the annular cavity defined by the ring members 46*j* and 146*j*. A radially inner boundary of the annular cavity can be defined by the flange portion 184*j*. A radially outer boundary of the annular cavity can be defined by the flange portion 84*j*. A posterior boundary of the annular cavity can be defined by the disc portion 82*j*. An anterior boundary of the annular cavity can be defined by the disc portion 182*j*. FIGS. 17 and 18 show the same cross-section; the embodiment 10*j* is shown in the uncoiled configuration in FIG. 17 and in the coiled configuration in FIG. 18. FIG. 19 is a view looking into the annular cavity with the disc portion 82*j* removed.

Figure 20:
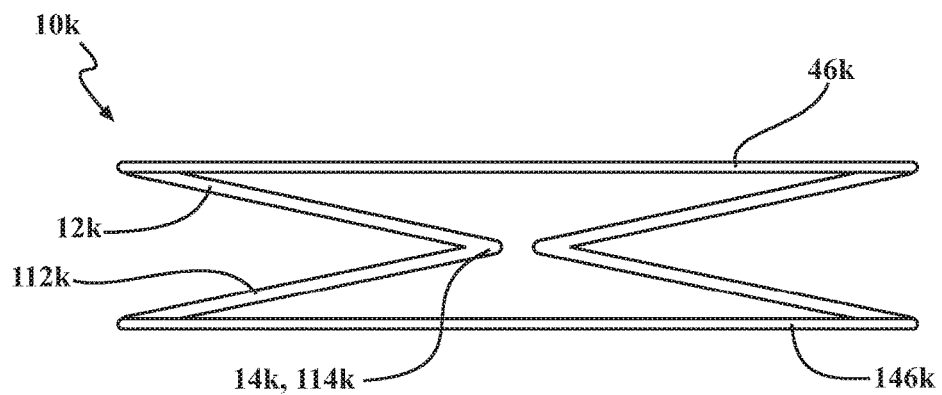
FIG. 20 is a side view of an embodiment in a pre-folded configuration.
Figure 21:
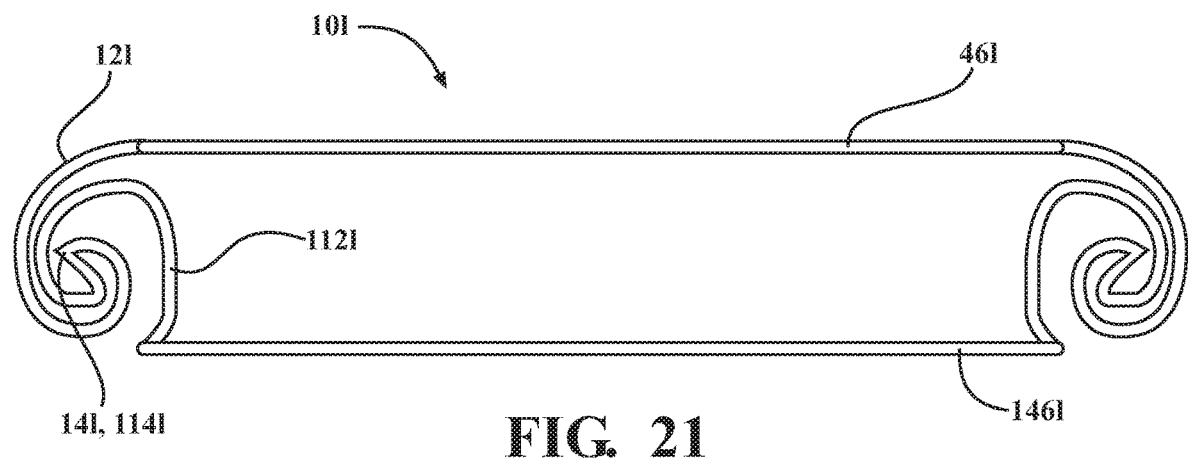
FIG. 21 is a side view of another embodiment in a pre-folded configuration.
Figure 22:
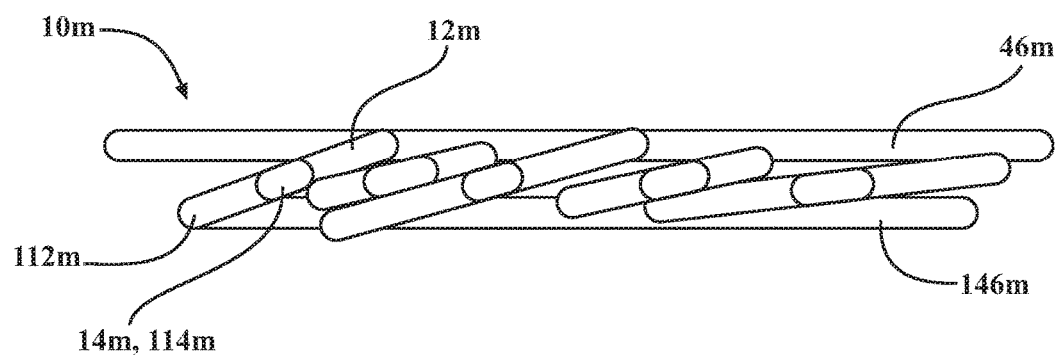
FIG. 22 is a side view of another embodiment in a pre-folded configuration.

FIGS. 20-22 are schematic views of various configurations in which an embodiment can be placed prior to folding and insertion in the eye of a patient. FIG. 20 shows an embodiment 10*k* with first and second ring members 46*k*, 146*k* and first and second sets of stanchions 12*k*, 112*k*. The stanchions 12*k*, 112*k* can be interconnected at a common base end 14*k*, 114*k*. Prior to folding, the stanchions 12*k*, 112*k* can be inverted, with the common base end 14*k*, 114*k* moved in between the first and second ring members 46*k*, 146*k*. The first and second ring members 46*k*, 146*k* can then be moved together, to the extent possible, and the entire structure can then be folded into a taco shell shape.

FIG. 21 is a schematic view of another embodiment in a pre-folded configuration. FIG. 21 shows an embodiment 10*l* with first and second ring members 46*l*, 146*l* and first and second sets of stanchions 12*l*, 112*l*. The stanchions 12*l*, 112*l* can be interconnected at a common base end 14*l*, 114*l*. Prior to folding, the stanchions 12*l*, 112*l* can be "rolled" together, with the common base end 14*k*, 114*k* at the center of the roll. The first and second ring members 46*k*, 146*k* can be rolled as well or can be moved together to the extent possible. The entire structure can then be folded into a taco shell shape.

FIG. 22 is a schematic view of another embodiment in a pre-folded configuration. FIG. 22 shows an embodiment 10*m* with first and second ring members 46*m*, 146*m* and first and second sets of stanchions 12*m*, 112*m*. The stanchions 12*m*, 112*m* can be interconnected at a common base end 14*m*, 114*m*. Prior to folding, the first and second ring members 46*m*, 146*m* can be rotated relative to one another and thereby drawing the first and second sets of stanchions 12*m*, 112*m* in between the first and second ring members 46*m*, 146*m*. The first and second ring members 46*m*, 146*m* can then be folded into a taco shell shape.

The term "coiling" has been used herein for the process of retracting stanchions relative to lenses, prior to insertion in the eye. The terms "folding" and "rolling" has been used for processes applied to an AIOL after the stanchions have been coiled. An AIOL can be elastically deformed by folding or by rolling in order to place the AIOL in a tool for subsequent insertion in the capsular bag or in the ciliary sulcus. As shown in the Figures of the present disclosure, the tool can be introduced through a small incision. One benefit enjoyed by various embodiments of the present disclosure is the completion of unfolding when the AIOL is in situ, which can serve as the mechanical trigger that unlocks the uncoiling of the stanchions since only discs that are roughly flat and parallel can spin relative to each other for the purposes of uncoiling. The temperature change and/or hydration experienced by the AIOL, once it is in the eye, can also be utilized to make the unfolding and uncoiling more controlled and atraumatic to the intraocular structures, by selecting material with appropriate biochemical properties.

It is noted that additional claims that can asserted in a divisional patent application include:

A method of positioning an AIOL in an eye comprising:

implanting an AIOL having a positive power lens in the eye wherein the AIOL also includes a plurality of stanchions each extending between the respective base end and a distal end, the plurality of base ends disposed in spaced relation to one another about a first arcuate periphery extending in a first plane wherein the first arcuate periphery is positioned in a ciliary sulcus of the eye, the distal ends disposed about a second arcuate periphery extending in a second plane positioned forward and outside of a capsular bag of the eye, the first plane spaced from the second plane in a posterior direction along a central optic axis, the first arcuate periphery having a greater radius than said second arcuate periphery and wherein the positive-power lens has an anterior side and a posterior side and a center disposed between the anterior side and the posterior side, the positive-power lens connected with each of the plurality of distal ends whereby a center of the positive power lens is moved along the central optic axis in response to contraction of the first arcuate periphery by contraction of the ciliary sulcus.

The method recited in paragraph [00246] wherein said implanting is further defined as:

implanting the AIOL having the positive power lens in the eye wherein the AIOL also includes a second plurality of stanchions each respectively extending between a second base end and a second distal end, each of the plurality of second base ends disposed in spaced relation to one another about said first arcuate periphery and are interconnected to one of said plurality of base ends at respective intersections positioned along said first arcuate periphery, the second distal ends disposed about a third arcuate periphery extending in a third plane, the third plane spaced from the first plane and the second plane along the central optic axis, the first arcuate periphery having a greater radius than the third arcuate periphery, and the AIOL also including a secondary lens having a second anterior side and a second posterior side and a second center disposed between the second anterior side and the second posterior side, said anterior side confronting the posterior side, the secondary lens connected with each of the plurality of second ends whereby the second center of the secondary lens is moved along the central optic axis in response to contraction of the first arcuate periphery by contraction of the ciliary sulcus.

The method recited in paragraph [00248] wherein said implanting is further comprising:

implanting a second plurality of stanchions the AIOL in the ciliary sulcus, each of the second plurality of stanchions respectively extending between a second base end and a second distal end, each of the plurality of second base ends disposed in spaced relation to one another about a third arcuate periphery in a third plane spaced from the first plane along the central optic axis, the second distal ends disposed about a fourth arcuate periphery extending in a fourth plane, the fourth plane spaced from the third plane along the central optic axis, the third arcuate periphery having a greater radius than the fourth arcuate periphery, and the AIOL also including a secondary lens having a second anterior side and a second posterior side and a second center disposed between the second anterior side and the second posterior side, said second anterior side confronting the posterior side, the secondary lens connected with each of the plurality of second ends whereby the second center of the secondary lens is moved along the central optic axis in response to contraction of the first arcuate periphery by contraction of the ciliary sulcus.

The method recited in paragraph [00248] further comprising:

filling at least one of the plurality of stanchions with fluid after said implanting.

The method recited in paragraph [00248] further comprising:

folding the AIOL prior to said implanting.

The method recited in paragraph [00248] further comprising:

modifying at least one mechanical property of at least one of the plurality of stanchions after said implanting.

The method recited in paragraph [00256] wherein said modifying further comprises:

applying electromagnetic energy to a portion of the at least one of the plurality of stanchions and thereby modifying an elasticity of the at least one of the plurality of stanchions.

Figure 24:
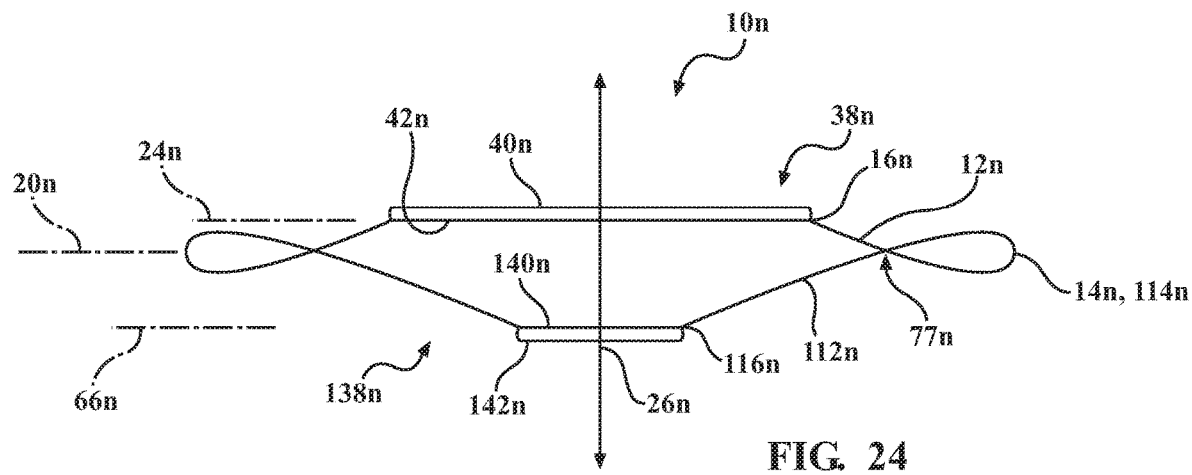
FIG. 24 is a front view of another exemplary embodiment of the present disclosure.
Figure 25:
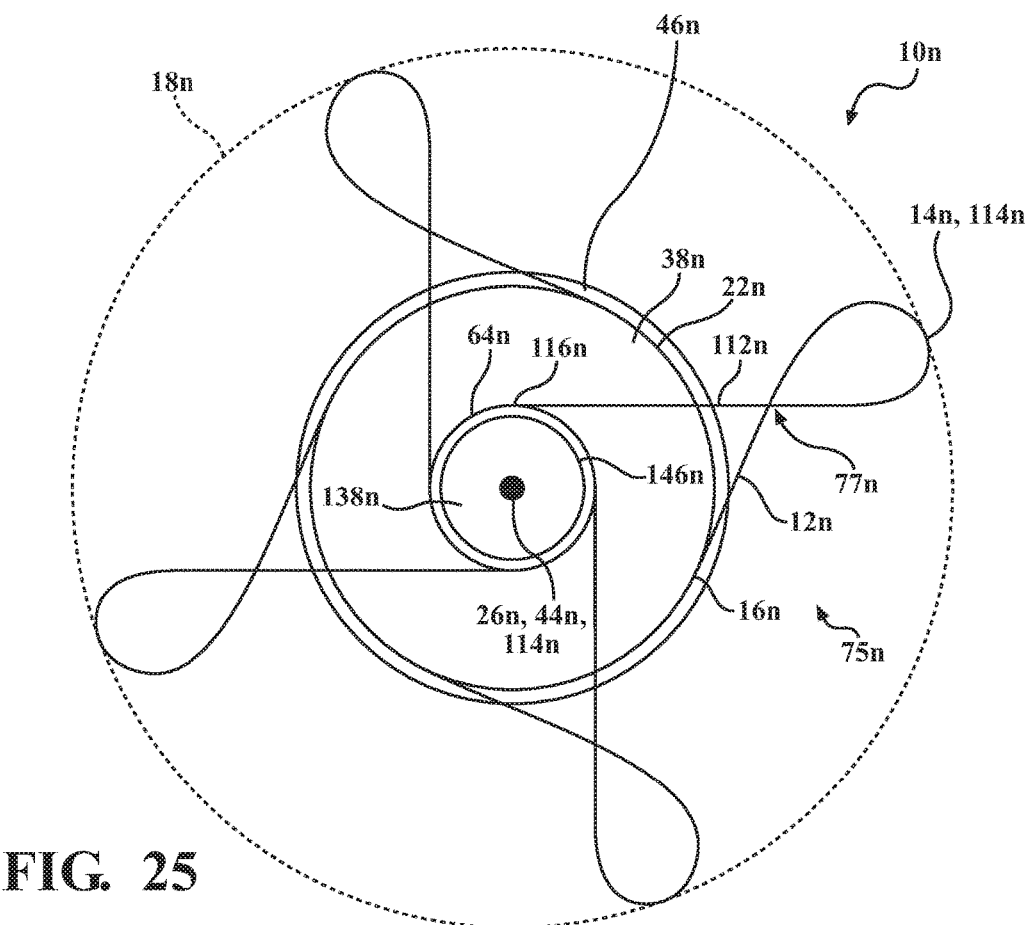
FIG. 25 is a bottom view of the exemplary embodiment shown in FIG. 24.
Figure 26:
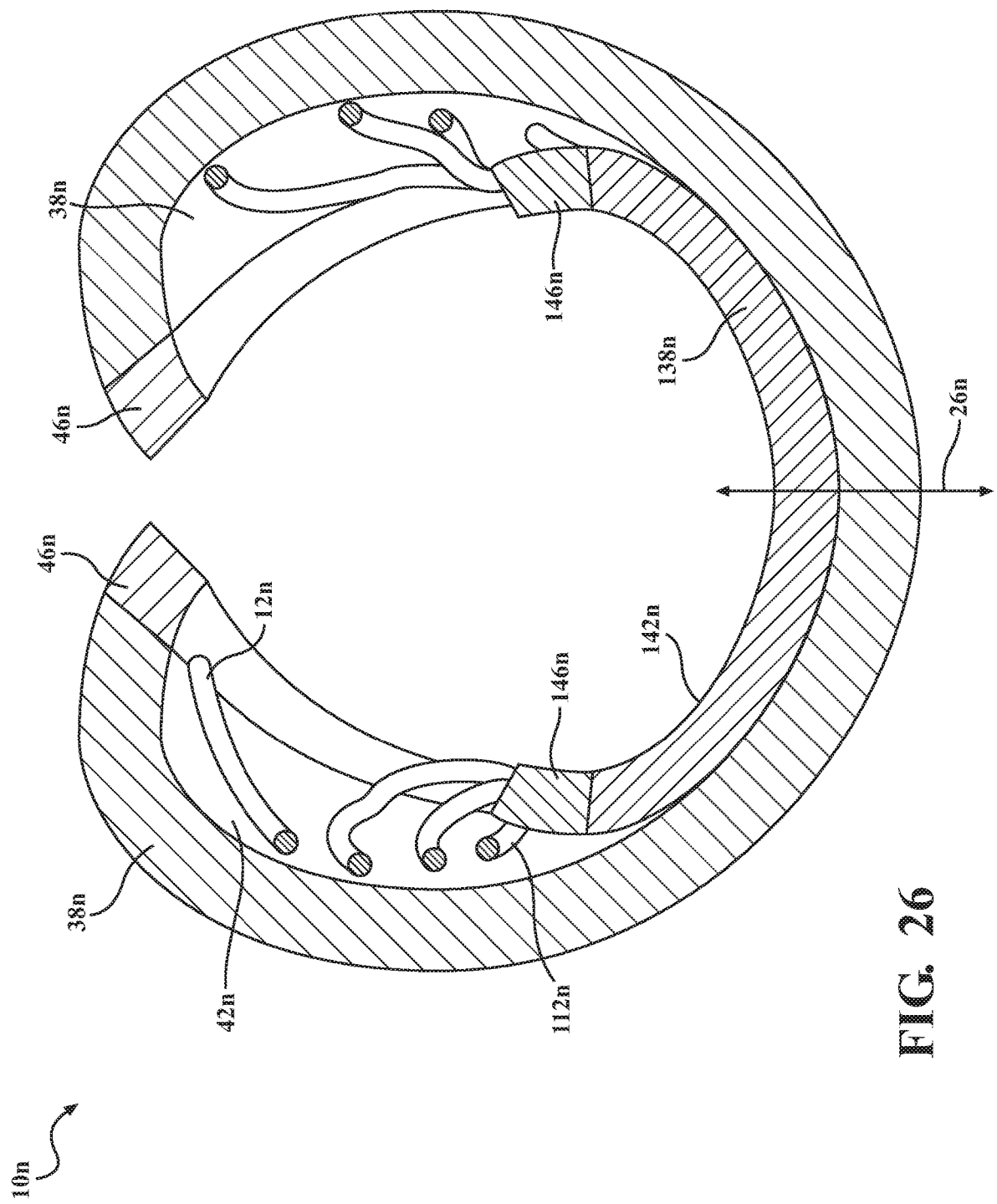
FIG. 26 is front view of the exemplary embodiment shown in FIGS. 24 and 25 after stanchions of the embodiment have been coiled and the embodiment has been elastically bent.
Figure 27:
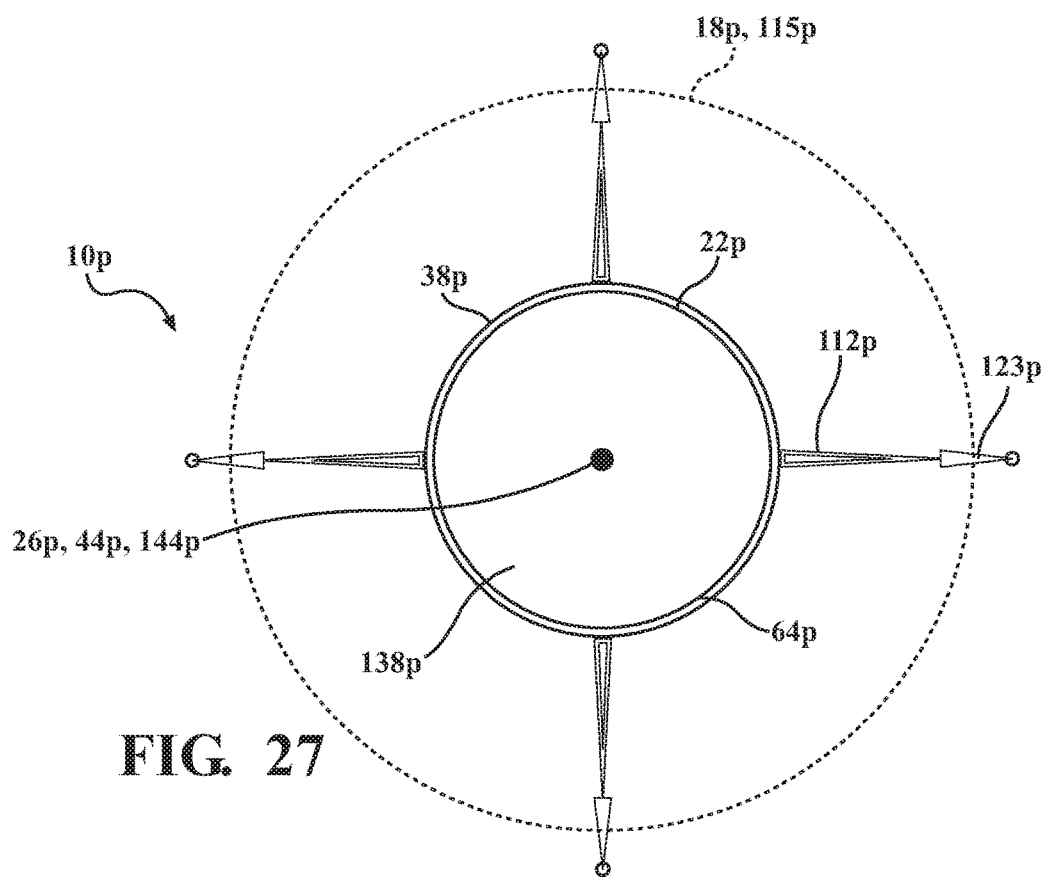
FIG. 27 is a top view of another exemplary embodiment of the present disclosure.

Another embodiment of the present disclosure is shown in FIGS. 24-26. An AIOL 10*n* includes a first lens 38*n* having a first anterior side 40*n* and a first posterior side 42*n* and a first center 44*n* disposed between the first anterior side 40*n* and the first posterior side 42*n*. A central optic axis 26*n* extends through the first center 44*n*. The AIOL 10*n* also includes a ring member 46*n* supporting the first lens 38*n*.

The AIOL 10*n* also includes a first plurality of stanchions 12*n* each extending a first distance between a first base end 14*n* and a first distal end 16*n*. The plurality of exemplary first base ends 14*n* are disposed in spaced relation to one another about a first arcuate periphery 18*n* extending in a first plane 20*n*. The exemplary first distal ends 16*n* are disposed about a second arcuate periphery 22*n* extending in a second plane 24*n*. The first plane 20*n* can be spaced from the second plane 24*n* in a posterior direction along the central optic axis 26*n*. The first arcuate periphery 18*n* can have a greater radius than the second arcuate periphery 22*n*. The exemplary first lens 38*n* is connected with each of the plurality of first distal ends 16*n*.

The AIOL 10*n* also includes a second lens 138*n* having a second anterior side 140*n* and a second posterior side 142*n* and a second center 144*n* disposed between the second anterior side 140*n* and the second posterior side 142*n*. The exemplary second anterior side 140*n* confronts the first posterior side 42*n* of the first lens 38*n*. The central optic axis 26n passes through the second center 144n. The AIOL 10n also includes a ring member 146n supporting the second lens 138n.

The AIOL 10n also includes a second plurality of stanchions 112n each respectively extending a second distance between a second base end 114n and a second distal end 116n. Each of the plurality of second base ends 114n can be disposed in spaced relation to one another about a third arcuate periphery extending in a third plane. In this exemplary embodiment, the third arcuate periphery is the same as the first arcuate periphery 18n and the third plane is the same as the first plane 20n. The second distal ends 116n can be disposed about a fourth arcuate periphery 64n extending in a fourth plane 66n. The third plane can be spaced from the fourth plane 66n along the central optic axis 26n. The exemplary third arcuate periphery has a greater radius than the fourth arcuate periphery 64n. The exemplary second lens 138n is connected with each of the plurality of second distal ends 116n.

Each of the first plurality of stanchions 12n is fixed with one of the second plurality of stanchions 112n at the respective first base end 14n and the second base end 114n to define a plurality of stanchion pairs 75n. A length is defined between the first distal end 16n of the stanchion 12n and the second distal end 116n of the stanchion 112n and a cross-sectional area of the stanchion pairs 75n is substantially constant along the length. The exemplary stanchions 12n, 112n have the same cross-sectional shape. As shown in FIG. 25, the exemplary stanchions 12n, 112n cross-over one another in a plane normal to the central optic axis 26n. FIG. 25 shows a plane normal to the central optic axis 26n. The cross-over point is referenced at 77n. As shown by FIG. 24, the exemplary stanchions 12n, 112n cross-over one another in a plane containing the central optic axis 26n. The exemplary cross-over point 77n is radially further from the central optic axis 26n than respective outside radii of both of the first lens 38n and the second lens 138n. It is noted that clinicians may refer to FIG. 24, as well as FIGS. 26, 28, 30, as a side or sagittal view.

Compression at the first arcuate periphery 18n (and thus the third arcuate periphery in this embodiment) induces movement of the first lens 38n and the second lens 138n apart from one other. The compression is transmitted through the stanchions 12n, 112n.

The first lens 38n has a first outside diameter and the second lens 138n has a second outside diameter. The first outside diameter is greater than the second outside diameter. A length between the first distal end 16n of the stanchion of the first plurality of stanchions 12n and the second distal end 116n of the stanchion of the second plurality of stanchions 112n is greater than an outside diameter of the second lens 138n and greater than a perimeter of the second lens 138n. The first plurality of stanchions 12n and the second plurality of stanchions 112n are thus elastically wrappable around the second outside diameter prior to insertion of the AIOL 10n in an eye.

A method of elastically deforming the AIOL 10n, prior to insertion of the AIOL 10n in an eye, can include rotating the first lens 38n and the second lens 138n relative to one another about the central optic axis 26n and thereby wrapping the first plurality of stanchions 12n and the second plurality of stanchions 112n around the second lens 138n. After the rotating, the AIOL 10n can be folded in half and further, with the edges of the ring member 46n folded over, while retaining the first plurality of stanchions 12n and the second plurality of stanchions 112n wrapped around the second lens 138n, as shown in FIG. 26.

Figure 31:
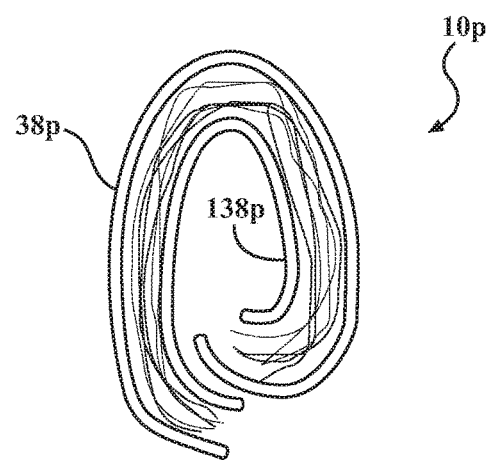
FIG. 31 is front view of the exemplary embodiment shown in FIGS. 27-30 after the stanchions of the embodiment have been coiled and the embodiment has been elastically bent.

AIOLs and IOLs of the prior art limit the folding of the IOL into half because of the thickness of the lens but embodiments of the present disclosure can be made thinner due to the combination of multiple thin optical elements which become spaced apart in-situ. Various embodiments of the present disclosure, such as shown in FIG. 31 for example, can be rolled (elastically deformed beyond folding). Although not shown in FIG. 26, the assembly 10n can be rolled as well. Further, embodiments of the present disclosure accommodate a large number of slender stanchions within the optical elements by coiling, whereas the prior art IOLs utilizes a pair of thick haptics (or haptic plates) that have to protrude from the edge of the optics and are thus exposed to damage during insertion/injection. The mechanical forces experienced by these haptics makes it necessary for them to be thicker and also limits their length. Increasing the size (and hence weight) of these haptics also tends to make the optic decenter through gravity.

Another embodiment of the present disclosure is shown in FIGS. 27-31. An AIOL 10p can include a first lens 38p having a first anterior side 40p, a first posterior side 42p, and a first center 44p disposed between the first anterior side 40p and the first posterior side 42p. A central optic axis 26p extends through the first center 44p.

A first plurality of stanchions 12p each extend a first distance between a first base end 14p and a first distal end 16p. The exemplary plurality of first base ends 14p are disposed in spaced relation to one another about a first arcuate periphery 18p extending in a first plane 20p. The first distal ends 16p can be disposed about a second arcuate periphery 22p extending in a second plane 24p. The first plane 20p can be spaced from the second plane 24p in a posterior direction along the central optic axis 26p. The first arcuate periphery 18p can have a greater radius than the second arcuate periphery 22p. The first lens 38p can be connected with each of the plurality of first distal ends 16p.

A second lens 138p has a second anterior side 140p and a second posterior side 142p and a second center 144p disposed between the second anterior side 140p and the second posterior side 142p. The exemplary second anterior side 140p confronts the first posterior side 42p of the first lens 38p. The central optic axis 26p passes through the second center 144p.

A second plurality of stanchions 112p each respectively extend a second distance between a respective second base end 114p and a respective second distal end 116p. Each of the plurality of second base ends 114p can be disposed in spaced relation to one another about a third arcuate periphery 115p extending in a third plane 117p. The exemplary first and third arcuate peripheries 18p, 115p are similarly-sized, but disposed in parallel, spaced planes that are normal to the central optic axis 26p. The second distal ends 116p can be disposed about a fourth arcuate periphery 64p extending in a fourth plane 66p. The third plane 117p is spaced from the fourth plane 66p along the central optic axis 26p. The third arcuate periphery 115p has a greater radius than the fourth arcuate periphery 64p. The second lens 138p can be connected with each of the plurality of second distal ends 116p.

Each of the first plurality of stanchions 12p can be fixed with one of the second plurality of stanchions 112p at the respective first base end 14p and the second base end 114p through an anchor member 123p, to define a plurality of stanchion pairs 75p. The anchor member 123p defines a bulbous and spherical tip. Compression at the first arcuate periphery 18p and the third arcuate periphery 115p, through the application of force on the anchor members, induces movement of the first lens 38p and the second lens 138p apart from one other. The compression is transmitted through the first plurality of stanchions 12p and the second plurality of stanchions 112p. Each of the first plurality of stanchions 12p is straight over at least most of the first distance and each of the second plurality of stanchions 112p is straight over at least most of the second distance.

Figure 29:
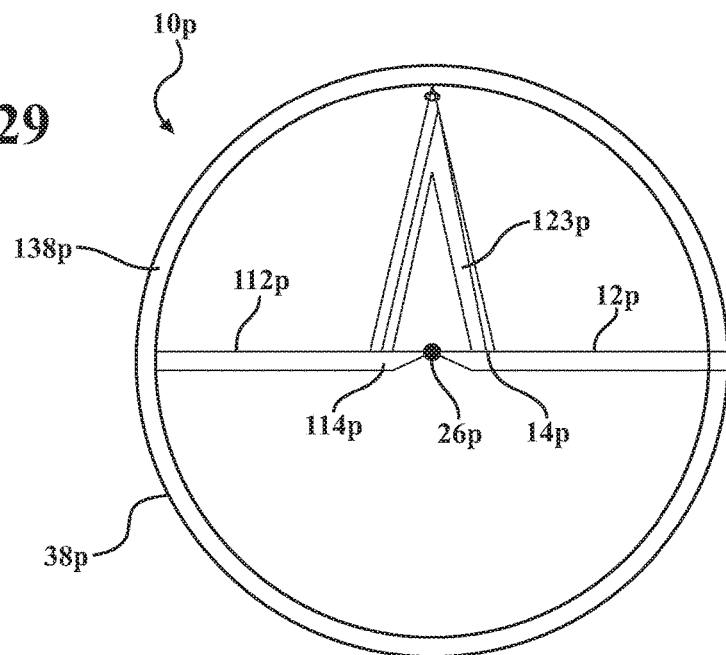
FIG. 29 is top view of the exemplary embodiment shown in FIGS. 27 and 28 after stanchions of the embodiment have been coiled.
Figure 30:
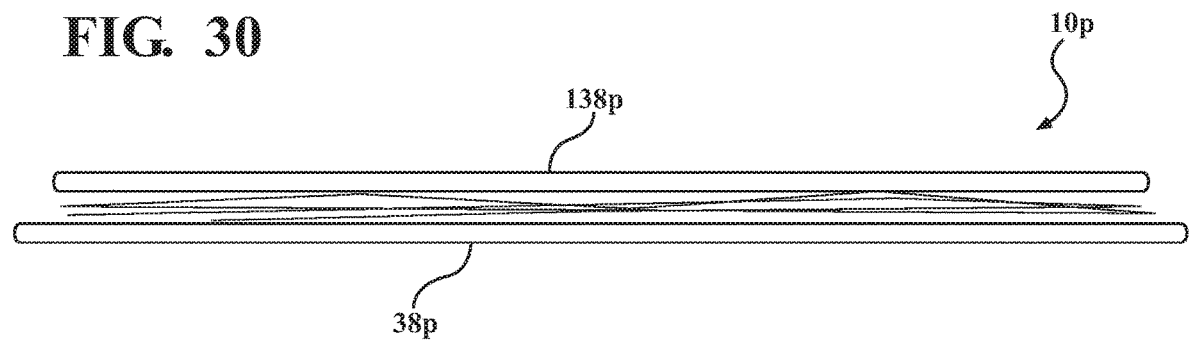
FIG. 30 is front view of the exemplary embodiment shown in FIGS. 27-29 after the stanchions of the embodiment have been coiled.

A method of elastically deforming the AIOL 10p, prior to insertion of the AIOL 10p in an eye, can include rotating the first lens 38p and the second lens 138p relative to one another about the central optic axis 26p and thereby drawing the first plurality of stanchions 12p and the second plurality of stanchions 112p in between the first lens 38p and the second lens 138p. This result is shown in FIGS. 29 and 30. A length is defined between the first distal end 16p of the stanchion of the first plurality of stanchions 12p and the second distal end 116p of the stanchion of the second plurality of stanchions 112p. This length is not greater than an outside diameter either the first lens 38p or the second lens 138p in this exemplary embodiment.

Figure 28:
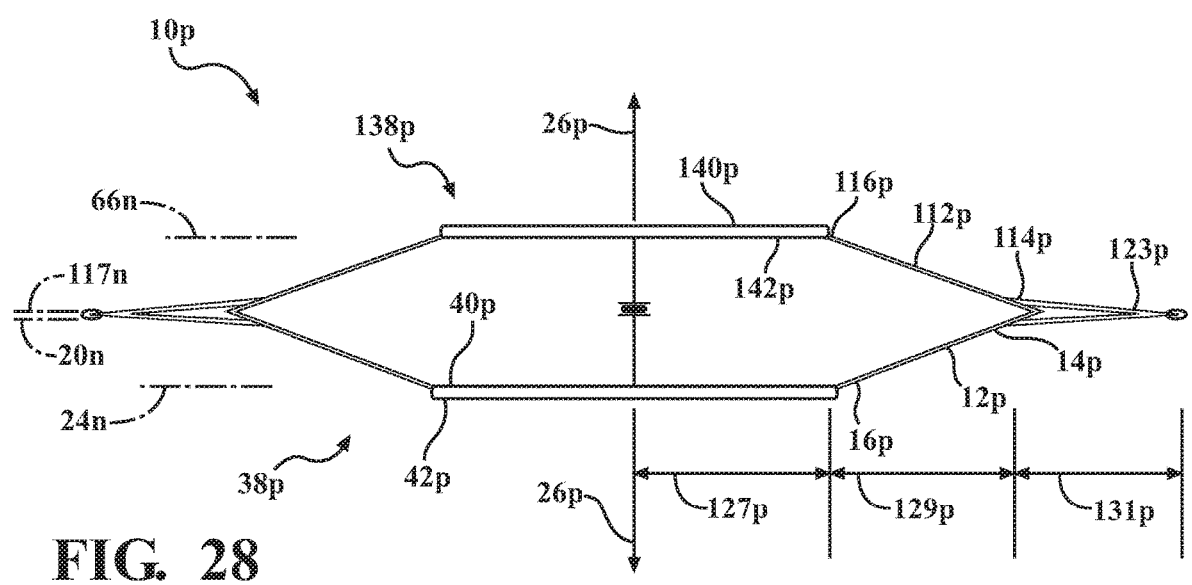
FIG. 28 is a front view of the exemplary embodiment shown in FIG. 27.

FIG. 28 is a side view of the assembly 10p in a static or unloaded state. The radius of the lens 38p (referenced at 12'7p) and the lengths of the stanchions 12p, 112p (referenced at 129p) are similar so that the stanchions 12p, 112p cooperate to define a substantially straight line across the lenses 38p, 138p when the lenses 38p, 138p have been rotated one hundred and eighty degrees relative to one another, as shown in FIG. 29. Further, the length of the stanchions 12p, 112p can be selected so that the lenses 38p, 138p are drawn together along the central optic axis 26p by relative rotation. Further, the radial length of the anchor member 125p (referenced at 131p) can be chosen so that anchor member 125p does not extend past the outside diameter of either lens 38p, 138p when the lenses 38p, 138p have been rotated relative to one another, as shown in FIG. 29.

After the rotating, the AIOL 10p can be folded in half while retaining the first plurality of stanchions 12p and the second plurality of stanchions 112p in between the first lens 38p and the second lens 138p. This is shown in FIG. 31. The anchor members 125p are also retained between the lens 38p, 138p.

The present disclosure also provides a method of modifying a capsular bag of an eye, which can be one part of a course of treatment for the eye. Generally, it can be desirable to replace a patient's original lens in the capsular bag in order to improve the vision of a patient. The contents of the capsular bag can be broken down and removal of the contents can be accomplished with a phacoemulsification system. The capsular bag can be subjected to two incisions, wherein a phacoemulsification tip of the phacoemulsification system is received in one of the incisions and a drainage tip of the collection system is received in the other incision. FIG. 9 of US 20140194859 discloses such an arrangement in operation.

Figure 38A:
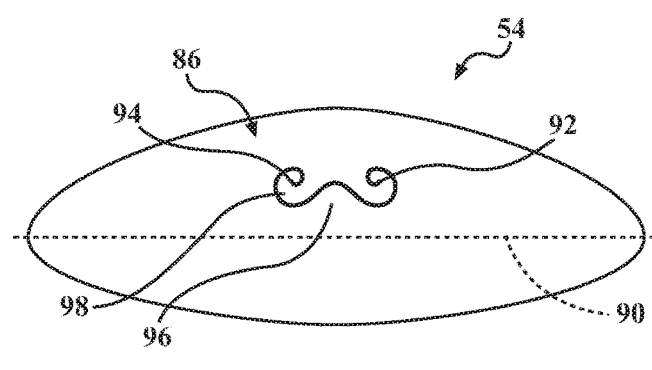
FIGS. 38A-38J are various patterns of curvilinear incisions or rhexes in the capsular bag.
Figure 38B:
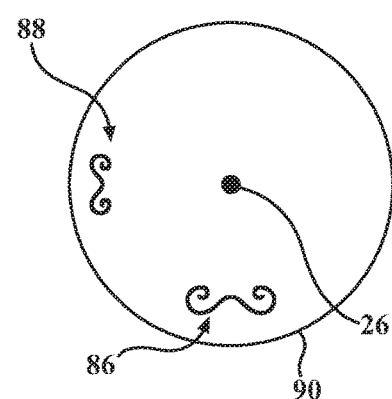
Figure 38C:
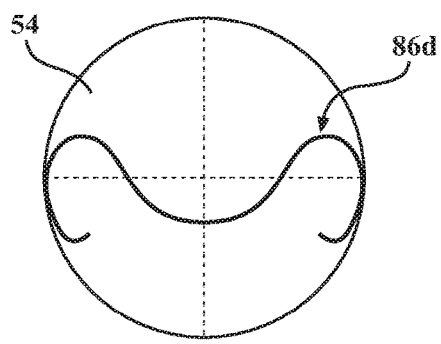
Figure 38D:
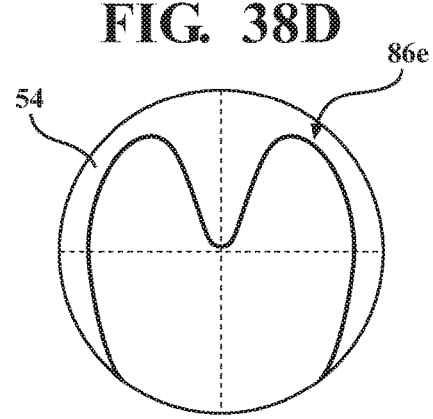

FIGS. 38A and 38B show exemplary rhexis or incision patterns provided by the present disclosure. The incisions are referenced at 86 and 88. The incisions 86, 88 have been made in the anterior side of the capsular bag 54. It is noted that while the capsular bag 54 is referenced, the AIOL 10, shown in FIG. 4, is not necessarily relevant to the incisions 86, 88. From the remainder of the disclosure, the capsular bag 54 will be referenced as a general capsular bag 54.

The incisions 86, 88 are spaced from the central optic axis 26 and from an equator 90 of the capsular bag 54. The exemplary incisions 86, 88 are of the same pattern, but the exemplary incision 86 is larger than the exemplary incision 88. The incision 86 can receive a portion of a phacoemulsification system or an IOL and the incision 88 can receive a second instrument, such as portion of a debris collection or drainage system.

The incisions 86, 88 are formed similarly and the creation of incision 86 is now described in greater detail. The continuous, meandering incision 86 can be initiated in the capsular bag 54 at a starting point. An exemplary starting point is referenced at 92. The continuous, meandering incision 86 can be formed with a femtosecond laser. The incision 86 is completed from the starting point 92, as the focus of the laser is moved over a tortuous path, to an end point referenced at 94. The "tortuous path" and the "incision" 86 are thus used synonymously. A "tortuous path" is a path marked by a plurality of twists, turns, or bends in a single direction along the path. A circle does not define a tortuous path since it does not twist; a circular path can be defined in a single plane. Also, a circle is not a tortuous path since no turns are defined along a circle; a turn is defined by a change in direction defined by an appreciable angle. Also, a circle is not a tortuous path since it extends along a single, continuous and constant bend. In the clockwise direction a circle extends along a right-hand bend and in the counter-clockwise direction a circle extends along a left-hand bend.

The exemplary incision 86 is sigmoid. The curves or flourishes at opposite the starting and ending points 92, 94 can be desirable to reduce the likelihood that tearing will occur at the ends of the incision 86 when the incision is at maximal stretch. Maximal stretch can occur during insertion of instruments, IOLs, or AIOLs.

After the exemplary incision 86 has been completed, no material is removed from the capsular bag 54 and at least one flap is retained in the capsular bag 54. Exemplary flaps are referenced at 96 and 98. Edges of the flaps 96, 98 mirror one another and are defined by the continuous meandering incision 86. During an exemplary operation on the capsular bag 54, a portion of a phacoemulsification system can be received in the incision 86 and a portion of a collection/drainage system can be received in the incision 88. The flaps 96, 98 can be folded into the bag as the portion of the phacoemulsification system is received. When the portion of the phacoemulsification system is drawn out, the flaps 96, 98 can unfold and generally abut one another again.

Referring now to FIGS. 40A-40D, the present disclosure provides a seal that can be utilized to seal the incision 86 and incisions having other shapes. An incision 86a in the capsular bag 54 has an S-shape with hooks at the ends. Flaps 96a, 98a are formed as a result of the incision 86a. A seal 100 is mounted in the capsular bag 54 to seal the incision 86a. The seal 100 inhibits leakage from the capsular bag 54 through the incision 86a. The seal 100 can include a first sealing panel 102 and a second sealing panel 104. Both sealing panels 102, 104 can be mounted on an insertion tool 106 having an outer tool portion 108 and an inner tool portion 110. The second sealing panel 104 can be releasably affixed to a tip 118 of the inner tool portion 110. For example, the bulbous tip 118 is releasably received in a similarly-shaped cavity 120 defined by the second sealing panel 104.

In operation, the second sealing panel 104 can be folded prior to insertion in the capsular bag 54 and unfolded after insertion in the capsular bag 54. After the second sealing panel 104 has been unfolded in the capsular bag 54, the tool portions 108, 110 can be moved relative to one another to draw the sealing panels 102, 104 together. As best shown in FIG. 40B, the exemplary second sealing panel 104 includes a flange collar 122 and the first sealing panel 102 includes a similarly-shaped cavity 124. The tool portions 108, 110 can be moved relative to one another to draw the sealing panels 102, 104 together until the flange collar 122 is received in the cavity 124 and, further, until the tip 118 is drawn out of the cavity 120. When the flange collar 122 is received in the cavity 124, the sealing panels 102, 104 pinch and hold adjacent edges of the incision 86a together.

As best shown in FIG. 40A, the exemplary sealing panels 102, 104 are bowed. Thus, when the flange collar 122 is received in the cavity 124, a perimeter of the seal 100 extends around the incision 86a, as best shown in FIG. 40D. The overlapping, perimeter portion of the sealing panels 102, 104 is referenced at 126. The exemplary, bowed sealing panels 102, 104 extert a biasing force on one another, with the capsular bag 54 disposed between the sealing panels 102, 104. This "sandwiching" of the capsular bag 54 between perimeters of the sealing panels 102, 104 occurs over the elliptically-shaped overlapping portion 126.

The cavity 120 can serve as a convenient port through which the sealed capsule could be inflated. The central channel that is shown in FIG. 40C would not be completely open but be part of a valve that allows one-way entry of fluid. This could be achieved by introducing a small needle or cannula through the membrane opening for injection. After removal of the needle or cannula, the central channel would seal either through an elastic membrane action or with the addition of supplemental valve mechanisms. Simultaneously, a second port, defined with a second seal similar to seal 100 and position on another rhexis such as incision 88a in FIG. 38G, could be used to remove the original capsular contents after cataract extraction (balanced salt solution or viscoelastic fluid) through vacuum via a cannula or needle so that the capsular bag could be reliably filled by a refractive medium. Since there is likely to be a difference in density between the refractive medium and of the original bag contents, the placement of the mini capsulorhexis 86a, 88a can be combined with positioning of the globe through head or neck rotation to allow proper filling so that the light turned medium is removed from the higher opening more easily through the assistance of gravity.

Figure 38E:
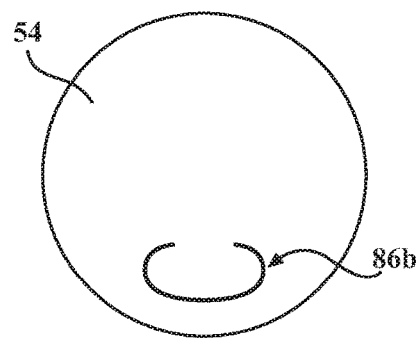
Figure 38F:
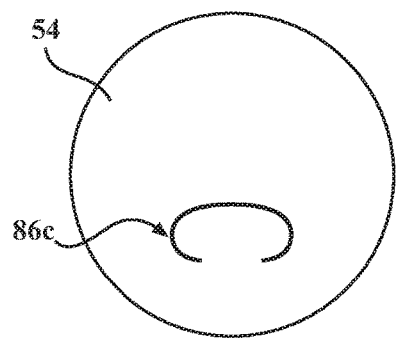

Other useful rhexis patterns are contemplated by the present disclosure. FIG. 38E shows a continuous, meandering incision 86b in the capsular bag 54. The incision 86b has a C-shape that is concave when considered from the center of the capsular bag 54. FIG. 38F shows a continuous, meandering incision 86c in the capsular bag 54 that has a C-shape that is convex when considered from the center of the capsular bag 54.

Figure 39:
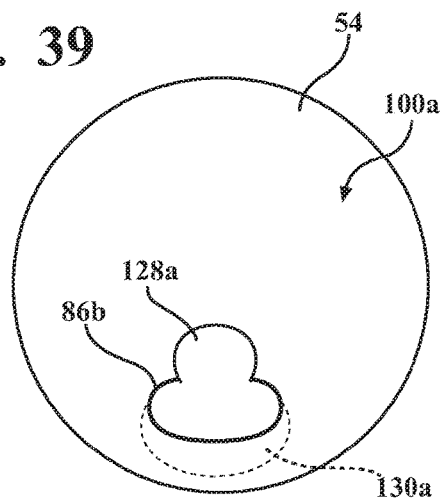
FIG. 39 is front view of capsular bag having a C-shaped curvilinear incision and a sealing plate positioned partially within the C-shaped curvilinear incision.

Referring now to FIG. 39, the present disclosure also provides a seal 100a that can be utilized to seal the incision 86b. The exemplary seal 100a is a unitary plate having, generally, the shape of a figure eight. The seal 100a includes a top portion 128a of the figure eight shape that is smaller than a bottom portion 130a of the figure eight shape. In operation, the incision 86b can be formed and the bottom portion 130a can be inserted in the capsular bag 54. The flap resulting from the incision 86b will be urged inside of the capsular bag 54 as the bottom portion 130a is inserted in the capsular bag 54. The bottom portion 130a and incision 86b are sized so that the opening in the capsular bag 54 resulting from the incision 86b will be stretched during insertion of the bottom portion 130a. The top portion 128a will remain outside of the capsular bag 54. The opening in the capsular bag 54 resulting from the incision 86b will be stretched around the neck of the seal 100a that is between the portions 128a, 130a.

When the seal 100a is mounted in the capsular bag 54, the flap resulting from the incision 86b will be remain inside of the capsular bag 54 and be pressed against the bottom portion 130a by pressure inside of the capsular bag 54. An outwardly facing surface of the bottom portion 130a will press and seal against an inwardly-facing surface of the capsular bag 54.

Figure 41:
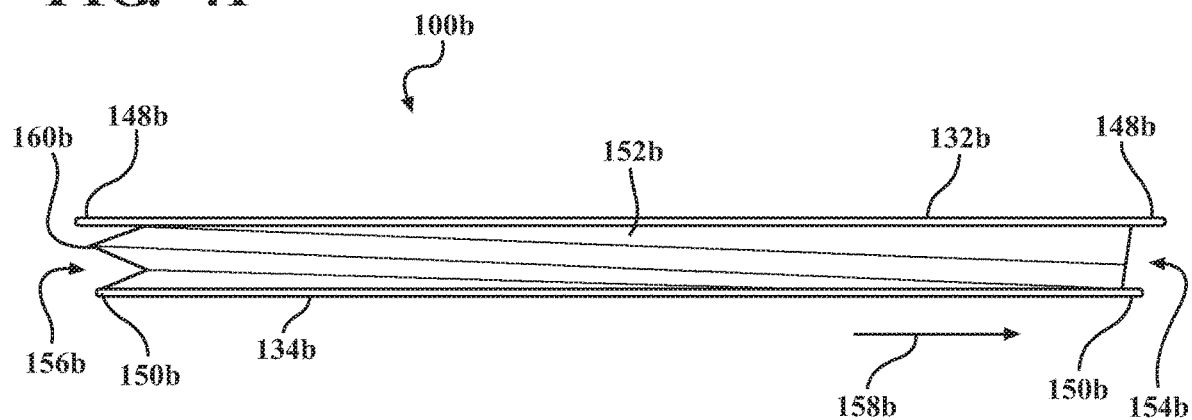
FIG. 41 is a front view of an exemplary seal for an incision.
Figure 42:
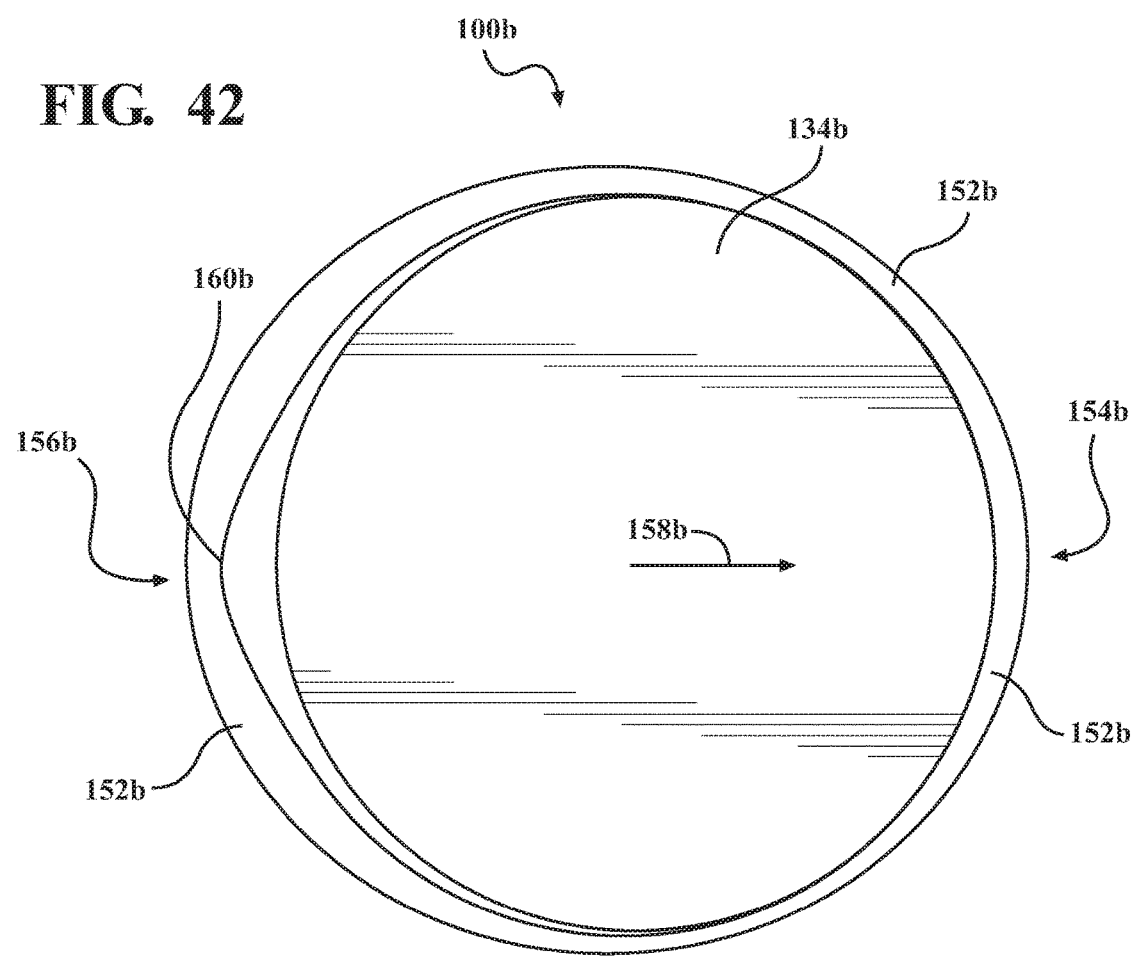
FIG. 42 is a bottom view of the exemplary seal shown in FIG. 41.

Referring now to FIGS. 41 and 42, the present disclosure also provides a seal 100b that can be utilized to seal various incisions. The exemplary seal 100b is a unitary structure extending between a top 132b and a bottom 134b. The seal 100b includes an annular flange 148b at the top 132b and an annular flange 150b at the bottom 134b. The seal 100b also includes a side surface 152b that extends vertically between the flanges 148b, 150b. The side surface 152b is generally frustoconical on a first side 154b. As the side surface 152b extends about a central axis of the seal 100b, from the first side 154b to a second side 156b, the side surface 152b continuously and progressively morphs from frustoconical on the first side 154b to a saw-tooth profile on the second side 156b. The exemplary side surface 152b includes a single tooth 160b on the second side 156b. During insertion in a capsular bag, the portion of the flange 150b on the first side 154b can be inserted in the opening in the capsular bag that is the result of an incision. The seal 100b can then be moved in a direction referenced by arrow 158b to stretch the opening until the portion of the flange 150b on the second side 156b can also be received in the opening. The seal 100b can then be inserted as far into the capsular bag as desired. The portion of the opening that is adjacent to the second side 156b of the side surface 152b can be captured between the tooth 160b and the flange 148b or between the tooth 160b and the flange 150b.

The present disclosure provides several alternative patterns for a continuous meandering incision extending over the tortuous path. The exemplary incisions 86, 88 disclosed in FIGS. 38A and 38B, the exemplary incisions 86a, 88a disclosed in FIG. 38G, and the exemplary incisions 86b and 86c respectively disclosed in FIGS. 38E and 38F are examples of an incision with spaced starting and end points. In other words, these incisions are not endless. Also, these incisions are spaced from the center of the capsular bag and can therefore be useful as entry points for a portion of a phacoemulsification system, an AIOL or IOL to be positioned in the capsular bag, or a portion of a collection/drainage system.

Figure 38G:
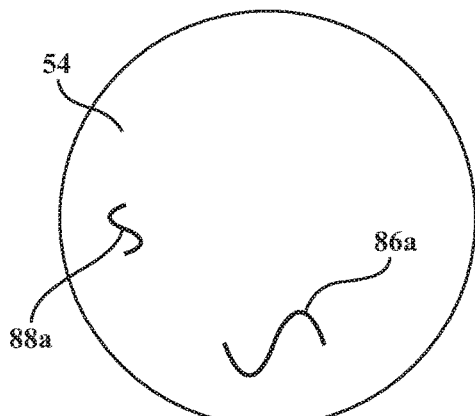
Figure 38H:
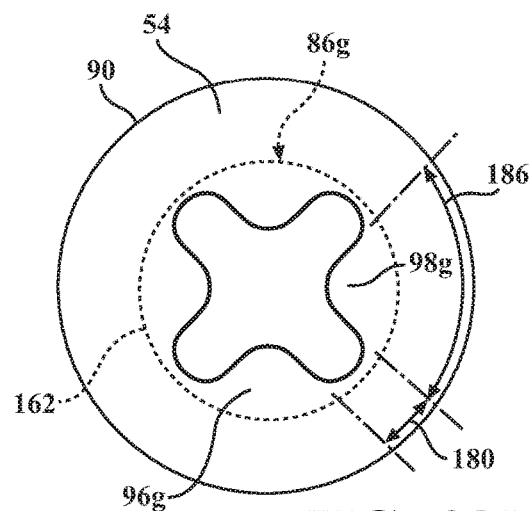
Figure 38I:
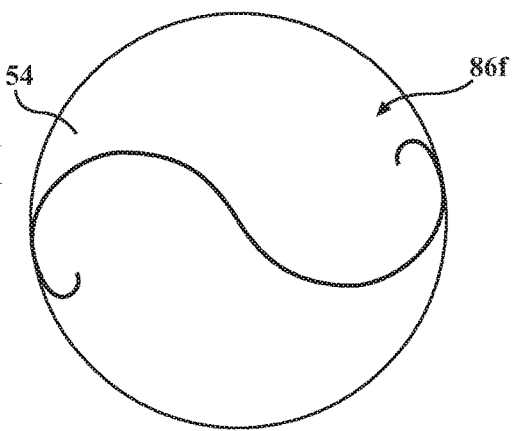
Figure 38J:
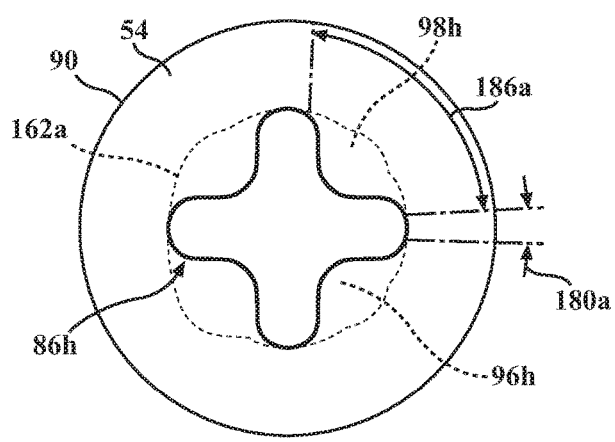

FIGS. 38C, 38D, 38H, 38I, and 38J disclose exemplary embodiments of incisions that are generally centered on the capsular bag. These incisions can be useful for forming openings in the capsular bag to receive an IOL. The exemplary incision 86d disclosed in FIG. 38C, the exemplary incision 86e disclosed in FIG. 38D, and the exemplary incision 86f disclosed in FIG. 38I are examples of incisions with spaced starting and end points. The exemplary incision 86g disclosed in FIG. 38H and the exemplary incision 86h disclosed in FIG. 38J are examples of incisions wherein starting point and end point are the same point, whereby the continuous meandering incision is endless. Both incisions 86g, 86h include bends in opposite directions as the path of respective incision is followed from any desired starting point, fully around and back to that starting point.

FIG. 38H is a front view of the capsular bag 54 and shows the anterior surface of the capsular bag 54. An equator of capsular bag 54 is referenced at 90. The exemplary incision 86g is "butterfly" shaped and can be utilized to mount an IOL in the capsular bag 54. The portion of the capsular bag 54 inside of the butterfly pattern is removed. Flaps, such as flaps 96g and 98g, can be folded back to form an opening in the capsular bag 54. A perimeter of an exemplary opening that can be formed in the capsular bag 54 as a result of the incision 86g is referenced at 162. The exemplary flaps 96g, 98g can be folded inside or outside of the capsular bag 54, although folding outside of the capsular bag 54 may be more desirable.

The larger, central rhexis shape shown in FIG. 38H can prevent redundant flaps of the capsular bag 54 from impeding the removal of nuclear fragments created when the nucleus of original lens is disintegrated with a femtosecond laser. Further, benefits pertaining to strength and elasticity of the capsular bag 54 will be maintained and there will still be the availability of folding of flaps to support a capsule-fixated interocular lens.

In one or more embodiments of the present disclosure, the incision 86a shown in FIG. 38G could be applied in the center of the capsular bag 54 and made larger, instead of the position shown in FIG. 38G. The incision is a sigmoid rhexis. As the cross-section of an opening resulting from the rhexis is expanded by the introduction of an instrument, the active circumference is formed by the natural capsular bag 54, which can recruit elastic ability in a plane perpendicular to each radius at the edge of the opening. The only "weak spots" would be at the very end of each incision and these may be fashioned so that stretching of the capsule will not be predisposed to radial tears, or the tips themselves may be included in the sleeve of capsular tissue that is not in direct contact with the instrument and its stretching forces.

An incision or rhexis will be able to expand while opening, increasing to a circumference that is a coefficient directly related to its initial, upstretched circumference. A central incision or capsulorhexis, such as incision 86d in FIG. 38C for example, can have a diameter of about 5.25 mm which can be considered optimal for current-art IOLs. The reason for this is that, if the edge of the capsulorhexis overlaps the optics of the IOL, the risk of lens epithelial cells proliferating into the capsule and creating posterior capsular opacification is reduced. It can generally be considered that a smaller capsulorhexis with the current art lenses would make access to the lens nucleus difficult without stretching the edge of the capsulorhexis and causing a radial tear. Another disadvantage of a smaller capsulorhexis is the difficulty of implanting a foldable IOL into the capsular bag through the small opening. A further difficulty may be access to the cortical remnants of the cataract which are stuck to the capsular bag and are especially difficult to reach under the area of the corneal incision because of the requirement of a looped instrument. This cortex is known as a sub incisional cortex and is particularly troublesome in femtosecond laser assisted cataract surgery (FLACS).

Figure 32:
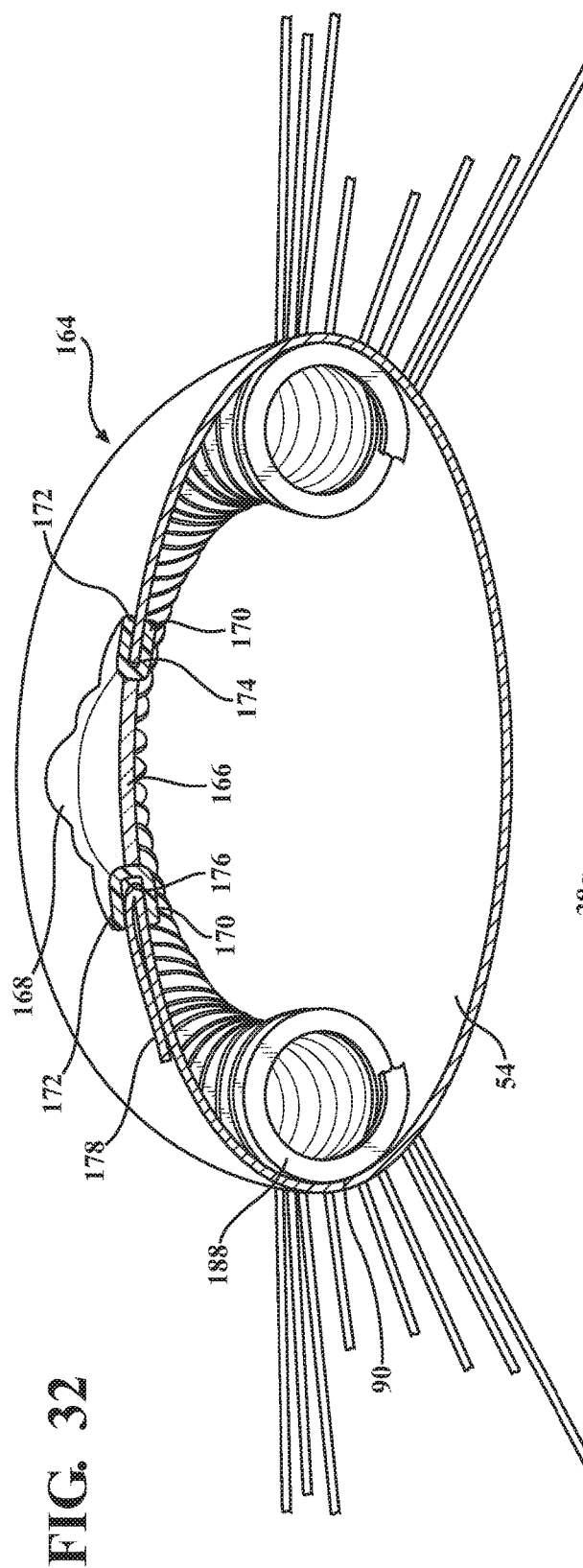
FIG. 32 is a perspective and cross-sectional view of another exemplary embodiment of the present disclosure.

However, in the case of an anterior capsule supported IOL, such as shown in FIG. 32, the issue of cell migration into the capsule is mitigated if the IOL is tightly sealed at its edges into the rim of the capsulorhexis. Therefore a larger capsulorhexis can be more safely performed and a maximal stretched diameter as much as seven or 8 mm is feasible provided such a large optic can be introduced through a small corneal incision. Multi-optic lenses can be compressed, rolled or folded into a taco shape, and inserted within a small corneal incision even though their optic diameter could be larger than the current typical maximum of 6 mm because two or more thin positive power lenses whose optical centers are separated in situ have optical power as great as a single convex lens whose total volume is greater. Thus, if a pair of thin positive power lenses could be rolled into a tube-like cylinder, they could be implanted through a narrow incision and achieve a substantially larger optical diameter once the connecting stanchions had unfolded to position the lenses in the intended location.

There is currently some debate as to which technique of capsulorhexis results in greater strength of the capsulorhexis edge and whether each technique increases or decreases stretch elasticity of the capsule. Various papers appear to have contradictory results. At present, in addition to femtosecond laser and a manual capsulorhexis, there are other technologies being developed to perform capsulorhexis. The present disclosure is not limited to any particular technology. Many technologies now offer more precise means of performing automated capsulorhexes in pre-programmed patterns. Generally, a technology that coagulates the proteins at the edge of the capsulorhexis tend to create a stronger edge diameter, but is also likely to reduce the elasticity at the edge. Therefore, the sigmoid pattern and others disclosed herein which do not simply the result in the excision of a central circular portion have the advantage of maintaining or increasing elasticity whilst maintaining or increasing capsule edge strength, because of the fold over over portion of the edge when the capsulorhexis is stretched either to introduce an instrument or to support a capsular fixated IOL.

FIG. 32 is a perspective view of a cross-section of the capsular bag 54. An intraocular lens assembly 164 is mounted in an opening formed in the capsular bag 54. The intraocular lens assembly 164 can be generally similar to the intraocular lens disclosed in U.S. Pat. No. 6,027,531, having a lens part 166 and a sealing, circumferential haptic part 168. A first sealing lip 170 of the haptic part 168 can be positioned on the inside of the capsular bag 54 and a second sealing lip 172 of the haptic part 168 can be positioned on the outside of the capsular bag 54.

As shown in FIG. 32, the haptic part 168 can seal directly against the opening along a portion 174 of the perimeter of the haptic portion 168 between the sealing lips 170, 172. At other portions of the perimeter, the haptic portion 168 can seal against a flap formed by the incision that resulted in the opening. For example, the haptic part 168 can seal directly against a folded edge along a portion 176 of the perimeter of the haptic portion 168 between the sealing lips 170, 172. The structure referenced at 178 is a flap analogous to the flaps 96g and 98g.

A benefit of rhexis patterns that extend along tortuous paths and form one or more flaps is that flaps can allow the capsular bag to be stretched in zones that are not altered by the formation of the incision. If the incision is formed by a femtosecond laser, for example, the edges of the incision may have been modified by the energy of the laser such that the edges are less elastic or the range of elasticity is diminished. The edge may undergo plastic deformation or unpredictable tearing in response to smaller amounts of stretching. Folded-over flaps allow for stretching along zones that will have retained the original elasticity of the capsular bag and are continuous.

Referring again to FIG. 38H, a portion of the exemplary opening 162 referenced at 180 will be defined by a stretched edge of the incision 86g. A portion of the exemplary opening 162 referenced at 186 will be defined by a stretched portion of the capsular bag 54. The portion 186 of the opening 162 will be defined by a "fold line" between the flap 98g and the portion of the capsular bag 54 that on the opposite side of the opening 162 from the flap 98g.

FIG. 38J is a front view of the capsular bag 54 and shows the anterior surface of the capsular bag 54. The equator of capsular bag 54 is referenced at 90. The exemplary incision 86h is generally shaped as a four-pointed star. The opening resulting from the incision 86h can be utilized to mount an IOL in the capsular bag 54. Flaps, such as flaps 96h and 98h, can be folded back to form an opening in the capsular bag 54. A perimeter of the exemplary opening is referenced at 162a. The exemplary flaps 96h, 98h can be folded inside or outside of the capsular bag 54. A portion of the exemplary opening 162a referenced at 180a will be defined by a stretched edge of the incision 86h. A portion of the exemplary opening 162a referenced at 186a will be defined by a stretched portion of the capsular bag 54. The portion 186a of the opening 162a will be defined by a "fold line" between the flap 98h and the portion of the capsular bag 54 that is on the opposite side of the opening 162a from the flap 98h. An IOL that could be mounted in the opening 162a could be in the shape of a rounded square rather than a circle, making it more stable for the purposes of unfolding into position and aligning any cylindrical (toric) lens element to treat astigmatism.

The present disclosure also provides a space-occupying element to support a capsular bag that receives an IOL. A space-occupying element can support a capsular bag that receives an IOL within the bag or mounted on the bag. Referring again to FIG. 32, a body 188 has been implanted in the capsular bag 54. The exemplary body 188 is positioned against the equator 90 of the capsular bag 54. The exemplary body 188 is a helical spring that is elastically deformed into a toroid shape within the capsular bag 54 and asserts a radially outward biasing force against the equator 90.

Bodies having a static shape other than a helical spring can be applied in one or more other embodiments of the present disclosure. The assembly 10d shown in FIG. 8, less the lens 38d, can serve as a space-occupying element to support a capsular bag that receives an IOL. In addition, FIG. 43A is a perspective view of an exemplary space-occupying element 188a according to an embodiment of the present disclosure. The exemplary element 188a is generally c-shaped in a static condition. FIG. 43B is a first schematic view of insertion of the exemplary space-occupying element 188a in the capsular bag 54. A circular opening 190 has been formed in the capsular bag 54 to receive an IOL. In FIG. 43B, the element 188a is shown elastically deformed and positioned in an insertion tool 106a. The insertion tool 106a has an outer tool portion 108a and an inner tool portion 110a. A slit 192 has been formed in the capsular bag 54 to receive the insertion tool 106a.

FIG. 43C is a second schematic view of insertion of the exemplary space-occupying element 188a into the capsular bag 54. A tip of the insertion tool 106a has been received in the slit 192. Further, the inner tool portion 110a has been moved within the outer tool portion 108a to push the element 188a out of the outer tool portion 108a and into the capsular bag 54. FIG. 43D is a front view after insertion of the element 188a into the capsular bag 54 and removal of the insertion tool 106a from the slit 192.

Figure 44A:
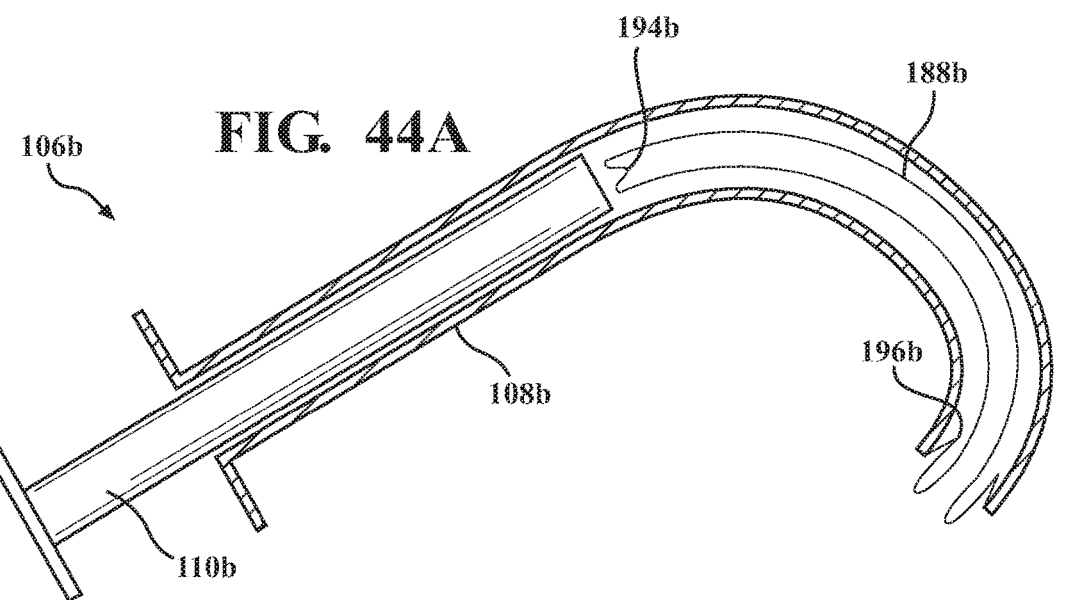
FIG. 44A is a first schematic side view of an exemplary insertion tool and space-occupying element according to another embodiment of the present disclosure.
Figure 44B:
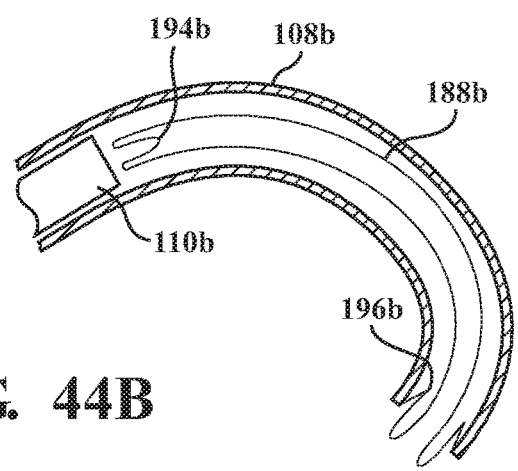
FIG. 44B is a second schematic view of the exemplary insertion tool and space-occupying element shown in FIG. 44A.
Figure 44C:
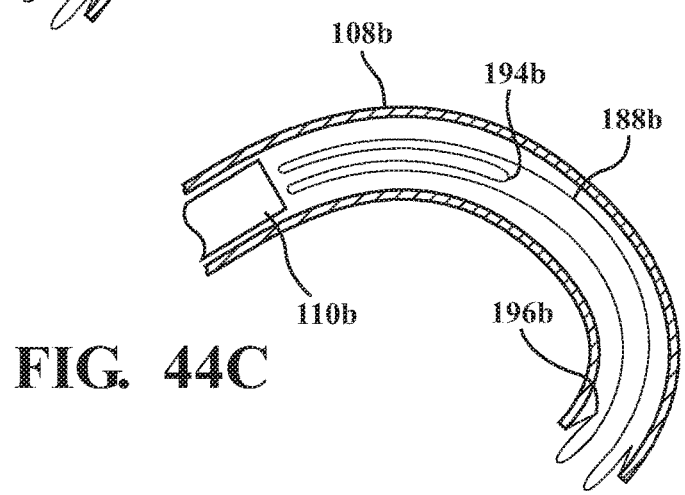
FIG. 44C is a third schematic view of the exemplary insertion tool and space-occupying element shown in FIGS. 44A and 44B.

FIG. 44A is a first schematic side view of another exemplary insertion tool 106b and space-occupying element 188b according to an embodiment of the present disclosure. The element 188b forms the shape of a cylindrical tube with one closed end 194b and one open end 196b when in a static or "unloaded" condition. The element 188b is elastically deformable. The insertion tool 106b has an outer tool portion 108b and an inner tool portion 110b. The open end 196b is releasably attached to the leading tip of the outer tool portion 108b. In operation, the tip of the outer tool portion 108b can be inserted in a slit defined in a capsular bag, as shown in FIG. 43C for another embodiment of the present disclosure. In the embodiment shown in FIGS. 44A-44C, the element 188b can be inside-out when positioned in the insertion tool 106b. Air can be directed through the inner tool portion 110b against the closed end 194b to drive the closed end 194b toward the open end 196b. This is shown progressively in FIGS. 44B and 44C. After the element 188b has been urged outside-out within the capsular bag, the open end 196b can detach from the tip of the outer tool portion 108b.

Figure 45A:
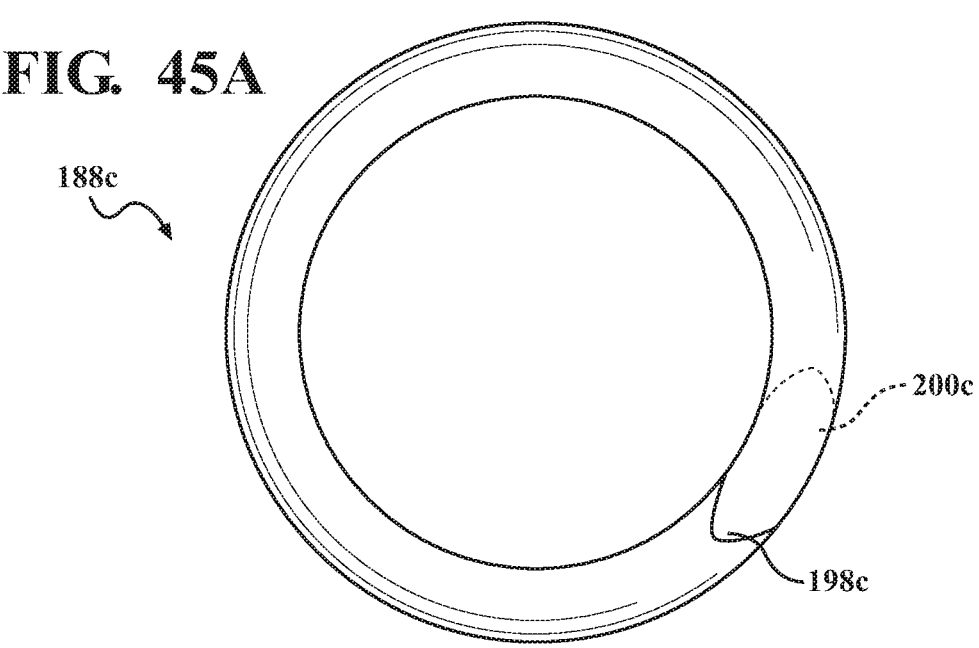
FIG. 45A is a front view of a space-occupying element according to another exemplary embodiment of the present disclosure.
Figure 45B:
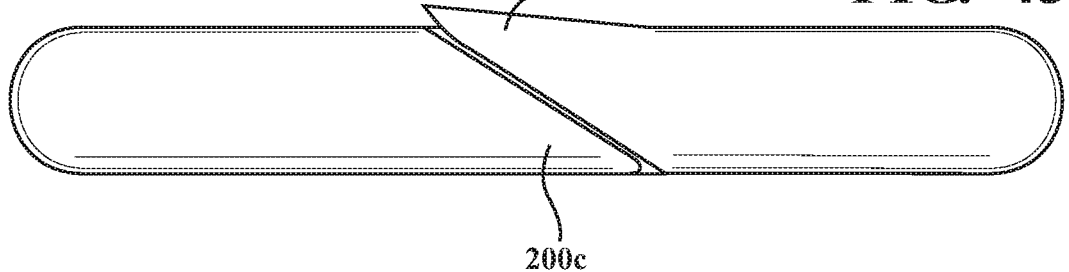
FIG. 45B is a right-hand view of the space-occupying element shown in FIG. 45A.
Figure 45C:
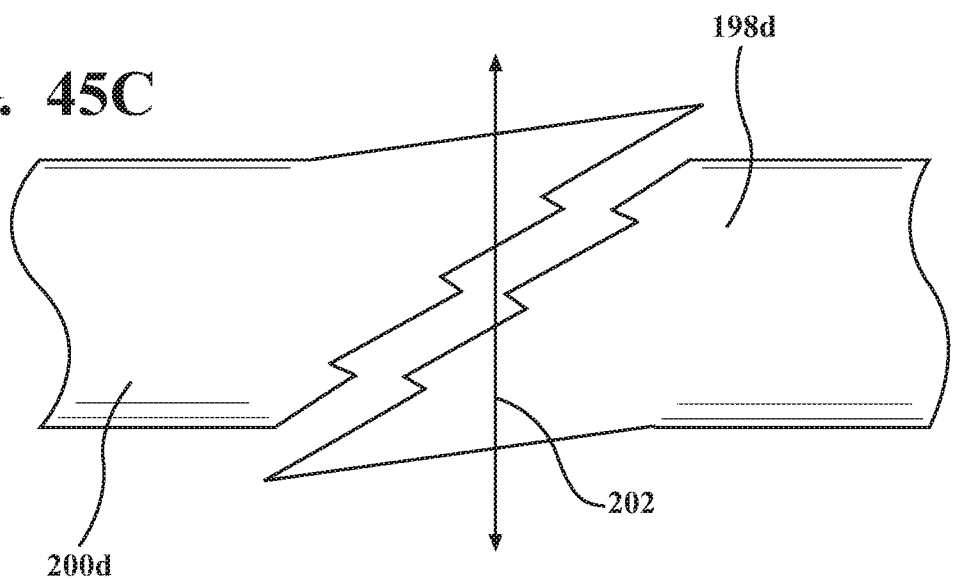
FIG. 45C is a right-hand view of a portion of a space-occupying element according to another exemplary embodiment of the present disclosure.

In one or more embodiments of the present disclosure, it may be desirable to engage opposite ends of a space-occupying element. FIG. 45A is a front view of a space-occupying element 188c according to another exemplary embodiment of the present disclosure. The element 188c is shown as it would appear when positioned in a capsular bag. The element 188c extends between first and second opposite ends 198c, 200c. The ends 198c, 200c define sloped, mating surfaces as shown in FIG. 45B, which is a right-hand view of the space-occupying element 188c. In one or more other embodiments of the present disclosure, it can be desirable to positively interconnect opposite ends of a space-occupying element to inhibit relative movement. FIG. 45C is a right-hand view of a portion of a space-occupying element according to another exemplary embodiment of the present disclosure. Ends 198d, 200d define mating sawtooth profiles. The respective profiles include teeth that, when mated, preclude either end 198d, 200d from shifting laterally.

It is noted that one or more structures disclosed herein can be formed from ChronoFlex C®, attainable from Advan-Source Biomaterials Corp. of Wilmington, Mass. It is also noted that the display of any particular embodiment is not to be viewed as limiting. Embodiments can be sized to work within an empty capsular bag (after cataract extraction) when placed in the ciliary sulcus, anterior chamber, capsular bag, or a combination of these locations.

While the present disclosure has been described with reference to an exemplary embodiment, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the appended claims. The right to claim elements and/or sub-combinations that are disclosed herein is hereby unconditionally reserved. The use of the word "can" in this document is not an assertion that the subject preceding the word is unimportant or unnecessary or "not critical" relative to anything else in this document. The word "can" is used herein in a positive and affirming sense and no other motive should be presumed. More than one "invention" may be disclosed in the present disclosure; an "invention" is defined by the content of a patent claim and not by the content of a detailed description of an embodiment of an invention.

What is claimed is:

1. An intraocular optic assembly comprising:
   a first lens having a first anterior side and a first posterior side and a first center disposed between said first anterior side and said first posterior side, wherein a central optic axis extends through said first center;
   a first plurality of stanchions each respectively extending a first distance between a first base end and a first distal end, said plurality of first base ends disposed in spaced relation to one another about a first arcuate periphery extending in a first plane, said first distal ends disposed about a second arcuate periphery extending in a second plane, said first plane spaced from said second plane in a posterior direction along said central optic axis, said first arcuate periphery having a greater radius than said second arcuate periphery, and said first lens connected with each of said plurality of first distal ends;

a second lens having a second anterior side and a second posterior side and a second center disposed between said second anterior side and said second posterior side, second anterior side confronting said first posterior side of said first lens, said central optic axis passing through said second center;

a second plurality of stanchions each respectively extending a second distance between a second base end and a second distal end, each of said plurality of second base ends disposed in spaced relation to one another about a third arcuate periphery extending in a third plane, said second distal ends disposed about a fourth arcuate periphery extending in a fourth plane, said third plane spaced from said fourth plane along said central optic axis, said third arcuate periphery having a greater radius than said fourth arcuate periphery, and said second lens connected with each of said plurality of second distal ends;

wherein each of said first plurality of stanchions is fixed with one of said second plurality of stanchions at said respective first base end and said respective second base end to define a plurality of stanchion pairs; and wherein at least one of said plurality of stanchion pairs includes a first stanchion of said first plurality of stanchions and a second stanchion of said second plurality of stanchions and wherein said first stanchion and said second stanchion cross-over one another in a plane normal to said central optic axis.

2. An intraocular optic assembly comprising:

a first lens having a first anterior side and a first posterior side and a first center disposed between said first anterior side and said first posterior side, wherein a central optic axis extends through said first center;

a first plurality of stanchions each respectively extending a first distance between a first base end and a first distal end, said plurality of first base ends disposed in spaced relation to one another about a first arcuate periphery extending in a first plane, said first distal ends disposed about a second arcuate periphery extending in a second plane, said first plane spaced from said second plane in a posterior direction along said central optic axis, said first arcuate periphery having a greater radius than said second arcuate periphery, and said first lens connected with each of said plurality of first distal ends;

a second lens having a second anterior side and a second posterior side and a second center disposed between said second anterior side and said second posterior side, second anterior side confronting said first posterior side of said first lens, said central optic axis passing through said second center;

a second plurality of stanchions each respectively extending a second distance between a second base end and a second distal end, each of said plurality of second base ends disposed in spaced relation to one another about a third arcuate periphery extending in a third plane, said second distal ends disposed about a fourth arcuate periphery extending in a fourth plane, said third plane spaced from said fourth plane along said central optic axis, said third arcuate periphery having a greater radius than said fourth arcuate periphery, and said second lens connected with each of said plurality of second distal ends;

wherein each of said first plurality of stanchions is fixed with one of said second plurality of stanchions at said respective first base end and said respective second base end to define a plurality of stanchion pairs; and wherein at least one of said plurality of stanchion pairs includes a first stanchion of said first plurality of stanchions and a second stanchion of said second plurality of stanchions and wherein said first stanchion and said second stanchion cross-over one another in a plane containing said central optic axis.

3. An intraocular optic assembly comprising:

a first lens having a first anterior side and a first posterior side and a first center disposed between said first anterior side and said first posterior side, wherein a central optic axis extends through said first center;

a first plurality of stanchions each respectively extending a first distance between a first base end and a first distal end, said plurality of first base ends disposed in spaced relation to one another about a first arcuate periphery extending in a first plane, said first distal ends disposed about a second arcuate periphery extending in a second plane, said first plane spaced from said second plane in a posterior direction along said central optic axis, said first arcuate periphery having a greater radius than said second arcuate periphery, and said first lens connected with each of said plurality of first distal ends;

a second lens having a second anterior side and a second posterior side and a second center disposed between said second anterior side and said second posterior side, second anterior side confronting said first posterior side of said first lens, said central optic axis passing through said second center;

a second plurality of stanchions each respectively extending a second distance between a second base end and a second distal end, each of said plurality of second base ends disposed in spaced relation to one another about a third arcuate periphery extending in a third plane, said second distal ends disposed about a fourth arcuate periphery extending in a fourth plane, said third plane spaced from said fourth plane along said central optic axis, said third arcuate periphery having a greater radius than said fourth arcuate periphery, and said second lens connected with each of said plurality of second distal ends;

wherein each of said first plurality of stanchions is fixed with one of said second plurality of stanchions at said respective first base end and said respective second base end to define a plurality of stanchion pairs; and wherein at least one of said plurality of stanchion pairs includes a first stanchion of said first plurality of stanchions and a second stanchion of said second plurality of stanchions and wherein said first stanchion and said second stanchion cross-over one another in a first plane normal to said central optic axis and also in a second plane containing said central optic axis.

4. An intraocular optic assembly comprising:

a first lens having a first anterior side and a first posterior side and a first center disposed between said first anterior side and said first posterior side, wherein a central optic axis extends through said first center;

a first plurality of stanchions each respectively extending a first distance between a first base end and a first distal end, said plurality of first base ends disposed in spaced relation to one another about a first arcuate periphery extending in a first plane, said first distal ends disposed about a second arcuate periphery extending in a second plane, said first plane spaced from said second plane in a posterior direction along said central optic axis, said first arcuate periphery having a greater radius than said second arcuate periphery, and said first lens connected with each of said plurality of first distal ends;

a second lens having a second anterior side and a second posterior side and a second center disposed between said second anterior side and said second posterior side, second anterior side confronting said first posterior side of said first lens, said central optic axis passing through said second center;

a second plurality of stanchions each respectively extending a second distance between a second base end and a second distal end, each of said plurality of second base ends disposed in spaced relation to one another about a third arcuate periphery extending in a third plane, said second distal ends disposed about a fourth arcuate periphery extending in a fourth plane, said third plane spaced from said fourth plane along said central optic axis, said third arcuate periphery having a greater radius than said fourth arcuate periphery, and said second lens connected with each of said plurality of second distal ends;

wherein each of said first plurality of stanchions is fixed with one of said second plurality of stanchions at said respective first base end and said respective second base end to define a plurality of stanchion pairs; and wherein at least one of said plurality of stanchion pairs includes a first stanchion of said first plurality of stanchions and a second stanchion of said second plurality of stanchions and wherein at least one of said first stanchion and said second stanchion extends away from the respective lens to which it is connected in a direction tangential to the respective lens.

5. The intraocular optic assembly of claim 4 wherein, for at least one of said stanchion pairs, a length between said first distal end of said stanchion of said first plurality of stanchions and said second distal end of said stanchion of said second plurality of stanchions is greater than an outside diameter of at least one of said first lens and said second lens.

6. The intraocular optic assembly of claim 5 wherein, said length is greater than a perimeter of said at least one of said first lens and said second lens.

7. The intraocular optic assembly of claim 4 wherein, for at least one of said stanchion pairs, a length is defined between said first distal end of said stanchion of said first plurality of stanchions and said second distal end of said stanchion of said second plurality of stanchions and wherein a cross-sectional area of said at least one of said stanchion pairs is substantially constant along said length.

8. The intraocular optic assembly of claim 7 wherein said stanchion of said first plurality of stanchions and said stanchion of said second plurality of stanchions cross-over one another in a plane normal to said central optic axis.

9. The intraocular optic assembly of claim 8 wherein said stanchion of said first plurality of stanchions and said stanchion of said second plurality of stanchions cross-over one another at a point and the point is radially further from said central optic axis than respective outside radii of both of said first lens and said second lens.

10. The intraocular optic assembly of claim 4 wherein said first lens has a first outside diameter and said second lens has a second outside diameter, said first outside diameter is greater than said second outside diameter, and said first plurality of stanchions and said second plurality of stanchions are elastically wrappable around said second outside diameter prior to insertion of said accommodating intraocular lens assembly in an eye.

11. The intraocular optic assembly of claim 4 wherein compression at said first arcuate periphery and said third arcuate periphery induces movement of said first lens and said second lens apart from one other, the compression transmitted through said first plurality of stanchions and said second plurality of stanchions.

12. The intraocular optic assembly of claim 4 wherein said first stanchion extends away from said first lens in a direction tangential to said first lens and said second stanchion extends away from said second lens in a direction tangential to said second lens.

13. The intraocular optic assembly of claim 4 wherein said at least one of said first stanchion and said second stanchion extends away from the respective lens to which it is connected in a direction tangential to the respective lens in a plane normal to said central optic axis.

14. The intraocular optic assembly of claim 13 wherein said at least one of said first stanchion and said second stanchion extends away from the respective lens to which it is connected in a direction non-tangential to the respective lens in a plane containing said central optic axis.

15. The intraocular optic assembly of claim 14 wherein said first plane is closer to said second plane along said central optic axis than to said fourth plane.

* * * * *